(12) United States Patent
Pau et al.

(10) Patent No.: US 7,553,937 B2
(45) Date of Patent: Jun. 30, 2009

(54) SPECIFIC ANTIBODIES FOR DIAGNOSING HEART FAILURE

(75) Inventors: Bernard Pau, Montpellier (FR); Isabelle Giuliani, Montpellier (FR); François Rieunier, Bois d' Arcy (FR)

(73) Assignees: Bio-Rad Pasteur, Marnes La Coquette (FR); Centre National de la Recherche Scientifique, Paris (FR); Universite Montpellier, Montpellier Cedex 1 (FR)

( * ) Notice: Subject to any disclaimer, the term of this patent is extended or adjusted under 35 U.S.C. 154(b) by 421 days.

(21) Appl. No.: 10/523,400

(22) PCT Filed: Aug. 7, 2003

(86) PCT No.: PCT/FR03/02483

§ 371 (c)(1),
(2), (4) Date: Nov. 14, 2005

(87) PCT Pub. No.: WO2004/014952

PCT Pub. Date: Feb. 19, 2004

(65) Prior Publication Data

US 2007/0299016 A1    Dec. 27, 2007

(30) Foreign Application Priority Data

Aug. 7, 2002    (FR) .................................. 02 10063

(51) Int. Cl.
*C12P 21/08*    (2006.01)
*C07K 16/00*    (2006.01)
*C07K 16/18*    (2006.01)

(52) U.S. Cl. ............ 530/387.9; 530/388.1; 530/388.24; 530/389.1; 530/389.2; 435/70.21

(58) Field of Classification Search ....................... None
See application file for complete search history.

(56) References Cited

U.S. PATENT DOCUMENTS

| 5,786,163 | A  | * | 7/1998 | Hall ........................ 435/7.92 |
| 6,117,644 | A  |   | 9/2000 | DeBold |
| 6,162,902 | A  |   | 12/2000 | Mischak et al. |
| 6,828,107 | B2 | * | 12/2004 | Asada et al. ................ 435/7.1 |
| 7,341,838 | B2 | * | 3/2008 | Buechler et al. ............. 435/7.1 |
| 2005/0118662 | A1 | * | 6/2005 | Spinke et al. ............... 435/7.92 |
| 2005/0244902 | A1 | * | 11/2005 | Gotze et al. ................ 435/7.92 |
| 2006/0110775 | A1 | * | 5/2006 | Borgya et al. ................ 435/7.1 |

FOREIGN PATENT DOCUMENTS

| WO | WO 9732900 A1 * | 9/1997 |
| WO | WO 00 35951    | 6/2000 |
| WO | WO 00 45176    | 8/2000 |

OTHER PUBLICATIONS

Goetze, et al., "Quantification of pro-B-type natriuretic peptide and its products in human plasma by use of an analysis independent of precursor processing", Clinical Chemistry, vol. 48, No. 7, p. 1035-1042, Jul. 2002, [XP001149219].

* cited by examiner

*Primary Examiner*—David S Romeo
*Assistant Examiner*—Daniel C Gamett
(74) *Attorney, Agent, or Firm*—Jacobson Holman PLLC

(57) ABSTRACT

The invention relates to an in vitro diagnosis of heart failure. More specifically, the invention relates to specific antibodies of a peptide domain which is situated on either side of hinge region R76S77 of proBNP(1-108). In particular, the invention relates to a method of obtaining the aforementioned antibodies and to the use thereof in detecting blood proBNP(1-108) with the exception of BNP(1-76) and BNP(77-108). The invention also relates to a method of detecting blood proBNP (1-108), reagents and a kit for same.

33 Claims, 16 Drawing Sheets

Reactivity (in relative intensity units):

| | | |
|---|---|---|
| 21 | IRGHRKMVLYTLRAP | 32.8 |
| 22 | HRKMVLYTLRAPRSP | 104.8 |
| 23 | MVLYTLRAPRSPKMV | 99.2 |
| 24 | YTLRAPRSPKMVQGS | 117.5 |
| 25 | RAPRSPKMVQGSGCF | 119.0 |
| 26 | RSPKMVQGSGCFGRK | 84.5 |
| 27 | KMVQGSGCFGRKMDR | 33.0 |

Spots detected: 22–26

Reactivity (in relative intensity units):

| | | |
|---|---|---|
| 21 | IRGHRKMVLYTLRAP | 32.0 |
| 22 | HRKMVLYTL RAPRSP | 125.9 |
| 23 | MVLYTL RAPRSPKMV | 104.2 |
| 24 | YTL RAPRSP KMVQGS | 121.1 |
| 25 | RAPRSP KMVQGSGCF | 113.7 |
| 26 | RSPKMVQGSGCFGRK | 35.0 |

Spots detected: 22–25

SEQUENCE LISTING

<160> NUMBER OF SEQ ID NOS: 124

<210> SEQ ID NO 1
<211> LENGTH: 108
<212> TYPE: PRT
<213> ORGANISM: Homo sapiens : proBNP(1-108)

<400> SEQUENCE: 1

His Pro Leu Gly Ser Pro Gly Ser Ala Ser Asp Leu Glu Thr Ser Gly
1               5                   10                  15

Leu Gln Glu Gln Arg Asn His Leu Gln Gly Lys Leu Ser Glu Leu Gln
                20                  25                  30

Val Glu Gln Thr Ser Leu Glu Pro Leu Gln Glu Ser Pro Arg Pro Thr
            35                  40                  45

Gly Val Trp Lys Ser Arg Glu Val Ala Thr Glu Gly Ile Arg Gly His
        50                  55                  60

Arg Lys Met Val Leu Tyr Thr Leu Arg Ala Pro Arg Ser Pro Lys Met
65                  70                  75                  80

Val Gln Gly Ser Gly Cys Phe Gly Arg Lys Met Asp Arg Ile Ser Ser
                85                  90                  95

Ser Ser Gly Leu Gly Cys Lys Val Leu Arg Arg His
                100                 105

<210> SEQ ID NO 2
<211> LENGTH: 32
<212> TYPE: PRT
<213> ORGANISM: Homo sapiens : proBNP(77-108)

<400> SEQUENCE: 2

Ser Pro Lys Met Val Gln Gly Ser Gly Cys Phe Gly Arg Lys Met Asp
1               5                   10                  15

```
Arg Ile Ser Ser Ser Gly Leu Gly Cys Lys Val Leu Arg Arg His
            20                  25                  30

<210> SEQ ID NO 3
<211> LENGTH: 76
<212> TYPE: PRT
<213> ORGANISM: Homo sapiens : proBNP(1-76)

<400> SEQUENCE: 3

His Pro Leu Gly Ser Pro Gly Ser Ala Ser Asp Leu Glu Thr Ser Gly
1               5                   10                  15

Leu Gln Glu Gln Arg Asn His Leu Gln Gly Lys Leu Ser Glu Leu Gln
            20                  25                  30

Val Glu Gln Thr Ser Leu Glu Pro Leu Gln Glu Ser Pro Arg Pro Thr
        35                  40                  45

Gly Val Trp Lys Ser Arg Glu Val Ala Thr Glu Gly Ile Arg Gly His
    50                  55                  60

Arg Lys Met Val Leu Tyr Thr Leu Arg Ala Pro Arg
65                  70                  75

<210> SEQ ID NO 4
<211> LENGTH: 16
<212> TYPE: PRT
<213> ORGANISM: Artificial Sequence
<220> FEATURE:
<221> NAME/KEY: MOD_RES
<222> LOCATION: (1)..(1)
<223> OTHER INFORMATION: chemically synthesized

<400> SEQUENCE: 4

Tyr Thr Leu Arg Ala Pro Arg Ser Pro Lys Met Val Gln Gly Ser Gly
1               5                   10                  15

<210> SEQ ID NO 5
<211> LENGTH: 6
<212> TYPE: PRT
<213> ORGANISM: Artificial Sequence
<220> FEATURE:
<221> NAME/KEY: MOD_RES
<222> LOCATION: (1)..(1)
<223> OTHER INFORMATION: chemically synthesized

<400> SEQUENCE: 5

Arg Ala Pro Arg Ser Pro
1               5

<210> SEQ ID NO 6
<211> LENGTH: 8
<212> TYPE: PRT
<213> ORGANISM: Artificial Sequence
<220> FEATURE:
<221> NAME/KEY: MOD_RES
<222> LOCATION: (1)..(1)
<223> OTHER INFORMATION: chemically synthesized

<400> SEQUENCE: 6

Cys Gly Arg Ala Pro Arg Ser Pro
1               5

<210> SEQ ID NO 7
<211> LENGTH: 8
<212> TYPE: PRT
<213> ORGANISM: Artificial Sequence
<220> FEATURE:
<221> NAME/KEY: MOD_RES
```

```
<222> LOCATION: (1)..(1)
<223> OTHER INFORMATION: chemically synthesized

<400> SEQUENCE: 7

Cys Gly Arg Ala Pro Arg Ser Pro
1               5

<210> SEQ ID NO 8
<211> LENGTH: 9
<212> TYPE: PRT
<213> ORGANISM: Artificial Sequence
<220> FEATURE:
<221> NAME/KEY: MOD_RES
<222> LOCATION: (1)..(1)
<223> OTHER INFORMATION: chemically synthesized

<400> SEQUENCE: 8

Cys Gly Arg Ala Pro Arg Ser Pro Lys
1               5

<210> SEQ ID NO 9
<211> LENGTH: 9
<212> TYPE: PRT
<213> ORGANISM: Artificial Sequence
<220> FEATURE:
<221> NAME/KEY: MOD_RES
<222> LOCATION: (1)..(1)
<223> OTHER INFORMATION: chemically synthesized

<400> SEQUENCE: 9

Cys Gly Arg Ala Pro Arg Ser Pro Lys
1               5

<210> SEQ ID NO 10
<211> LENGTH: 11
<212> TYPE: PRT
<213> ORGANISM: Artificial Sequence
<220> FEATURE:
<221> NAME/KEY: MOD_RES
<222> LOCATION: (1)..(1)
<223> OTHER INFORMATION: chemically synthesized

<400> SEQUENCE: 10

Cys Gly Arg Ala Pro Arg Ser Pro Lys Met Val
1               5                   10

<210> SEQ ID NO 11
<211> LENGTH: 15
<212> TYPE: PRT
<213> ORGANISM: Artificial Sequence
<220> FEATURE:
<221> NAME/KEY: MOD_RES
<222> LOCATION: (1)..(1)
<223> OTHER INFORMATION: chemically synthesized

<400> SEQUENCE: 11

Cys Gly Arg Ala Pro Arg Ser Pro Lys Met Val Gln Gly Ser Gly
1               5                   10                  15

<210> SEQ ID NO 12
<211> LENGTH: 8
<212> TYPE: PRT
<213> ORGANISM: Artificial Sequence
<220> FEATURE:
<221> NAME/KEY: MOD_RES
<222> LOCATION: (1)..(1)
<223> OTHER INFORMATION: chemically synthesized

<400> SEQUENCE: 12
```

```
Arg Ala Pro Arg Ser Pro Gly Cys
1               5

<210> SEQ ID NO 13
<211> LENGTH: 8
<212> TYPE: PRT
<213> ORGANISM: Artificial Sequence
<220> FEATURE:
<221> NAME/KEY: MOD_RES
<222> LOCATION: (1)..(1)
<223> OTHER INFORMATION: chemically synthesized

<400> SEQUENCE: 13

Arg Ala Pro Arg Ser Pro Gly Cys
1               5

<210> SEQ ID NO 14
<211> LENGTH: 11
<212> TYPE: PRT
<213> ORGANISM: Artificial Sequence
<220> FEATURE:
<221> NAME/KEY: MOD_RES
<222> LOCATION: (1)..(1)
<223> OTHER INFORMATION: chemically synthesized

<400> SEQUENCE: 14

Cys Tyr Thr Leu Arg Ala Pro Arg Ser Pro Lys
1               5                   10

<210> SEQ ID NO 15
<211> LENGTH: 17
<212> TYPE: PRT
<213> ORGANISM: Artificial Sequence
<220> FEATURE:
<221> NAME/KEY: MOD_RES
<222> LOCATION: (1)..(1)
<223> OTHER INFORMATION: chemically synthesized

<400> SEQUENCE: 15

Cys His Arg Lys Met Val Leu Tyr Thr Leu Arg Ala Pro Arg Ser Pro
1               5                   10                  15

Lys

<210> SEQ ID NO 16
<211> LENGTH: 17
<212> TYPE: PRT
<213> ORGANISM: Artificial Sequence
<220> FEATURE:
<221> NAME/KEY: MOD_RES
<222> LOCATION: (1)..(1)
<223> OTHER INFORMATION: chemically synthesized

<400> SEQUENCE: 16

Cys Tyr Thr Leu Arg Ala Pro Arg Ser Pro Lys Met Val Gln Gly Ser
1               5                   10                  15

Gly

<210> SEQ ID NO 17
<211> LENGTH: 17
<212> TYPE: PRT
<213> ORGANISM: Artificial Sequence
<220> FEATURE:
<221> NAME/KEY: MOD_RES
<222> LOCATION: (1)..(1)
<223> OTHER INFORMATION: chemically synthesized

<400> SEQUENCE: 17
```

```
Cys Phe Thr Leu Arg Ala Pro Arg Ser Pro Lys Met Val Gln Gly Ser
1               5                   10                  15

Gly

<210> SEQ ID NO 18
<211> LENGTH: 17
<212> TYPE: PRT
<213> ORGANISM: Artificial Sequence
<220> FEATURE:
<221> NAME/KEY: MOD_RES
<222> LOCATION: (1)..(1)
<223> OTHER INFORMATION: chemically synthesized

<400> SEQUENCE: 18

Cys Phe Ser Ile Arg Ala Pro Arg Ser Pro Lys Met Val Gln Gly Ser
1               5                   10                  15

Gly

<210> SEQ ID NO 19
<211> LENGTH: 17
<212> TYPE: PRT
<213> ORGANISM: Artificial Sequence
<220> FEATURE:
<221> NAME/KEY: MOD_RES
<222> LOCATION: (17)..(17)
<223> OTHER INFORMATION: chemically synthesized

<400> SEQUENCE: 19

Cys Tyr Thr Leu Arg Ala Pro Arg Ser Pro Lys Met Val Gln Gly Ser
1               5                   10                  15

Ala

<210> SEQ ID NO 20
<211> LENGTH: 17
<212> TYPE: PRT
<213> ORGANISM: Artificial Sequence
<220> FEATURE:
<221> NAME/KEY: MOD_RES
<222> LOCATION: (17)..(17)
<223> OTHER INFORMATION: chemically synthesized

<400> SEQUENCE: 20

Cys Tyr Thr Leu Arg Ala Pro Arg Ser Pro Lys Met Val Gln Ala Thr
1               5                   10                  15

Ala

<210> SEQ ID NO 21
<211> LENGTH: 17
<212> TYPE: PRT
<213> ORGANISM: Artificial Sequence
<220> FEATURE:
<221> NAME/KEY: MOD_RES
<222> LOCATION: (17)..(17)
<223> OTHER INFORMATION: chemically synthesized

<400> SEQUENCE: 21

Cys Phe Ser Ile Arg Ala Pro Arg Ser Pro Lys Met Val Gln Ala Thr
1               5                   10                  15

Ala

<210> SEQ ID NO 22
<211> LENGTH: 17
<212> TYPE: PRT
<213> ORGANISM: Artificial Sequence
```

```
<220> FEATURE:
<221> NAME/KEY: MOD_RES
<222> LOCATION: (1)..(1)
<223> OTHER INFORMATION: chemically synthesized

<400> SEQUENCE: 22

Cys Phe Ser Ile Arg Ala Pro Arg Ser Pro Ala Leu Ala Ser Gly Thr
1               5                   10                  15
Ala

<210> SEQ ID NO 23
<211> LENGTH: 15
<212> TYPE: PRT
<213> ORGANISM: Artificial Sequence
<220> FEATURE:
<221> NAME/KEY: MOD_RES
<222> LOCATION: (1)..(1)
<223> OTHER INFORMATION: chemically synthesized

<400> SEQUENCE: 23

His Pro Leu Gly Ser Pro Gly Ser Ala Ser Asp Leu Glu Thr Ser
1               5                   10                  15

<210> SEQ ID NO 24
<211> LENGTH: 15
<212> TYPE: PRT
<213> ORGANISM: Artificial Sequence
<220> FEATURE:
<221> NAME/KEY: MOD_RES
<222> LOCATION: (1)..(1)
<223> OTHER INFORMATION: chemically synthesized

<400> SEQUENCE: 24

Gly Ser Pro Gly Ser Ala Ser Asp Leu Glu Thr Ser Gly Leu Gln
1               5                   10                  15

<210> SEQ ID NO 25
<211> LENGTH: 15
<212> TYPE: PRT
<213> ORGANISM: Artificial Sequence
<220> FEATURE:
<221> NAME/KEY: MOD_RES
<222> LOCATION: (1)..(1)
<223> OTHER INFORMATION: chemically synthesized

<400> SEQUENCE: 25

Gly Ser Ala Ser Asp Leu Glu Thr Ser Gly Leu Gln Glu Gln Arg
1               5                   10                  15

<210> SEQ ID NO 26
<211> LENGTH: 15
<212> TYPE: PRT
<213> ORGANISM: Artificial Sequence
<220> FEATURE:
<221> NAME/KEY: MOD_RES
<222> LOCATION: (1)..(1)
<223> OTHER INFORMATION: chemically synthesized

<400> SEQUENCE: 26

Ser Asp Leu Glu Thr Ser Gly Leu Gln Glu Gln Arg Asn His Leu
1               5                   10                  15

<210> SEQ ID NO 27
<211> LENGTH: 15
<212> TYPE: PRT
<213> ORGANISM: Artificial Sequence
<220> FEATURE:
<221> NAME/KEY: MOD_RES
```

```
<222> LOCATION: (1)..(1)
<223> OTHER INFORMATION: chemically synthesized

<400> SEQUENCE: 27

Glu Thr Ser Gly Leu Gln Glu Gln Arg Asn His Leu Gln Gly Lys
1               5                   10                  15

<210> SEQ ID NO 28
<211> LENGTH: 15
<212> TYPE: PRT
<213> ORGANISM: Artificial Sequence
<220> FEATURE:
<221> NAME/KEY: MOD_RES
<222> LOCATION: (1)..(1)
<223> OTHER INFORMATION: chemically synthesized

<400> SEQUENCE: 28

Gly Leu Gln Glu Gln Arg Asn His Leu Gln Gly Lys Leu Ser Glu
1               5                   10                  15

<210> SEQ ID NO 29
<211> LENGTH: 15
<212> TYPE: PRT
<213> ORGANISM: Artificial Sequence
<220> FEATURE:
<221> NAME/KEY: MOD_RES
<222> LOCATION: (1)..(1)
<223> OTHER INFORMATION: chemically synthesized

<400> SEQUENCE: 29

Glu Gln Arg Asn His Leu Gln Gly Lys Leu Ser Glu Leu Gln Val
1               5                   10                  15

<210> SEQ ID NO 30
<211> LENGTH: 15
<212> TYPE: PRT
<213> ORGANISM: Artificial Sequence
<220> FEATURE:
<221> NAME/KEY: MOD_RES
<222> LOCATION: (1)..(1)
<223> OTHER INFORMATION: chemically synthesized

<400> SEQUENCE: 30

Asn His Leu Gln Gly Lys Leu Ser Glu Leu Gln Val Glu Gln Thr
1               5                   10                  15

<210> SEQ ID NO 31
<211> LENGTH: 15
<212> TYPE: PRT
<213> ORGANISM: Artificial Sequence
<220> FEATURE:
<221> NAME/KEY: MOD_RES
<222> LOCATION: (1)..(1)
<223> OTHER INFORMATION: chemically synthesized

<400> SEQUENCE: 31

Gln Gly Lys Leu Ser Glu Leu Gln Val Glu Gln Thr Ser Leu Glu
1               5                   10                  15

<210> SEQ ID NO 32
<211> LENGTH: 15
<212> TYPE: PRT
<213> ORGANISM: Artificial Sequence
<220> FEATURE:
<221> NAME/KEY: MOD_RES
<222> LOCATION: (1)..(1)
<223> OTHER INFORMATION: chemically synthesized

<400> SEQUENCE: 32
```

Leu Ser Glu Leu Gln Val Glu Gln Thr Ser Leu Glu Pro Leu Gln
1               5                   10                  15

<210> SEQ ID NO 33
<211> LENGTH: 15
<212> TYPE: PRT
<213> ORGANISM: Artificial Sequence
<220> FEATURE:
<221> NAME/KEY: MOD_RES
<222> LOCATION: (1)..(1)
<223> OTHER INFORMATION: chemically synthesized

<400> SEQUENCE: 33

Leu Gln Val Glu Gln Thr Ser Leu Glu Pro Leu Gln Glu Ser Pro
1               5                   10                  15

<210> SEQ ID NO 34
<211> LENGTH: 15
<212> TYPE: PRT
<213> ORGANISM: Artificial Sequence
<220> FEATURE:
<221> NAME/KEY: MOD_RES
<222> LOCATION: (1)..(1)
<223> OTHER INFORMATION: chemically synthesized

<400> SEQUENCE: 34

Glu Gln Thr Ser Leu Glu Pro Leu Gln Glu Ser Pro Arg Pro Thr
1               5                   10                  15

<210> SEQ ID NO 35
<211> LENGTH: 15
<212> TYPE: PRT
<213> ORGANISM: Artificial Sequence
<220> FEATURE:
<221> NAME/KEY: MOD_RES
<222> LOCATION: (1)..(1)
<223> OTHER INFORMATION: chemically synthesized

<400> SEQUENCE: 35

Ser Leu Glu Pro Leu Gln Glu Ser Pro Arg Pro Thr Gly Val Trp
1               5                   10                  15

<210> SEQ ID NO 36
<211> LENGTH: 15
<212> TYPE: PRT
<213> ORGANISM: Artificial Sequence
<220> FEATURE:
<221> NAME/KEY: MOD_RES
<222> LOCATION: (1)..(1)
<223> OTHER INFORMATION: chemically synthesized

<400> SEQUENCE: 36

Pro Leu Gln Glu Ser Pro Arg Pro Thr Gly Val Trp Lys Ser Arg
1               5                   10                  15

<210> SEQ ID NO 37
<211> LENGTH: 15
<212> TYPE: PRT
<213> ORGANISM: Artificial Sequence
<220> FEATURE:
<221> NAME/KEY: MOD_RES
<222> LOCATION: (1)..(1)
<223> OTHER INFORMATION: chemically synthesized

<400> SEQUENCE: 37

Glu Ser Pro Arg Pro Thr Gly Val Trp Lys Ser Arg Glu Val Ala
1               5                   10                  15

```
<210> SEQ ID NO 38
<211> LENGTH: 15
<212> TYPE: PRT
<213> ORGANISM: Artificial Sequence
<220> FEATURE:
<221> NAME/KEY: MOD_RES
<222> LOCATION: (1)..(1)
<223> OTHER INFORMATION: chemically synthesized

<400> SEQUENCE: 38

Arg Pro Thr Gly Val Trp Lys Ser Arg Glu Val Ala Thr Glu Gly
1               5                   10                  15

<210> SEQ ID NO 39
<211> LENGTH: 15
<212> TYPE: PRT
<213> ORGANISM: Artificial Sequence
<220> FEATURE:
<221> NAME/KEY: MOD_RES
<222> LOCATION: (1)..(1)
<223> OTHER INFORMATION: chemically synthesized

<400> SEQUENCE: 39

Gly Val Trp Lys Ser Arg Glu Val Ala Thr Glu Gly Ile Arg Gly
1               5                   10                  15

<210> SEQ ID NO 40
<211> LENGTH: 15
<212> TYPE: PRT
<213> ORGANISM: Artificial Sequence
<220> FEATURE:
<221> NAME/KEY: MOD_RES
<222> LOCATION: (1)..(1)
<223> OTHER INFORMATION: chemically synthesized

<400> SEQUENCE: 40

Lys Ser Arg Glu Val Ala Thr Glu Gly Ile Arg Gly His Arg Lys
1               5                   10                  15

<210> SEQ ID NO 41
<211> LENGTH: 15
<212> TYPE: PRT
<213> ORGANISM: Artificial Sequence
<220> FEATURE:
<221> NAME/KEY: MOD_RES
<222> LOCATION: (1)..(1)
<223> OTHER INFORMATION: chemically synthesized

<400> SEQUENCE: 41

Glu Val Ala Thr Glu Gly Ile Arg Gly His Arg Lys Met Val Leu
1               5                   10                  15

<210> SEQ ID NO 42
<211> LENGTH: 15
<212> TYPE: PRT
<213> ORGANISM: Artificial Sequence
<220> FEATURE:
<221> NAME/KEY: MOD_RES
<222> LOCATION: (1)..(1)
<223> OTHER INFORMATION: chemically synthesized

<400> SEQUENCE: 42

Thr Glu Gly Ile Arg Gly His Arg Lys Met Val Leu Tyr Thr Leu
1               5                   10                  15

<210> SEQ ID NO 43
<211> LENGTH: 15
<212> TYPE: PRT
```

```
<213> ORGANISM: Artificial Sequence
<220> FEATURE:
<221> NAME/KEY: MOD_RES
<222> LOCATION: (1)..(1)
<223> OTHER INFORMATION: chemically synthesized

<400> SEQUENCE: 43

Ile Arg Gly His Arg Lys Met Val Leu Tyr Thr Leu Arg Ala Pro
1               5                   10                  15

<210> SEQ ID NO 44
<211> LENGTH: 15
<212> TYPE: PRT
<213> ORGANISM: Artificial Sequence
<220> FEATURE:
<221> NAME/KEY: MOD_RES
<222> LOCATION: (1)..(1)
<223> OTHER INFORMATION: chemically synthesized

<400> SEQUENCE: 44

His Arg Lys Met Val Leu Tyr Thr Leu Arg Ala Pro Arg Ser Pro
1               5                   10                  15

<210> SEQ ID NO 45
<211> LENGTH: 15
<212> TYPE: PRT
<213> ORGANISM: Artificial Sequence
<220> FEATURE:
<221> NAME/KEY: MOD_RES
<222> LOCATION: (1)..(1)
<223> OTHER INFORMATION: chemically synthesized

<400> SEQUENCE: 45

Met Val Leu Tyr Thr Leu Arg Ala Pro Arg Ser Pro Lys Met Val
1               5                   10                  15

<210> SEQ ID NO 46
<211> LENGTH: 15
<212> TYPE: PRT
<213> ORGANISM: Artificial Sequence
<220> FEATURE:
<221> NAME/KEY: MOD_RES
<222> LOCATION: (1)..(1)
<223> OTHER INFORMATION: chemically synthesized

<400> SEQUENCE: 46

Tyr Thr Leu Arg Ala Pro Arg Ser Pro Lys Met Val Gln Gly Ser
1               5                   10                  15

<210> SEQ ID NO 47
<211> LENGTH: 15
<212> TYPE: PRT
<213> ORGANISM: Artificial Sequence
<220> FEATURE:
<221> NAME/KEY: MOD_RES
<222> LOCATION: (1)..(1)
<223> OTHER INFORMATION: chemically synthesized

<400> SEQUENCE: 47

Arg Ala Pro Arg Ser Pro Lys Met Val Gln Gly Ser Gly Cys Phe
1               5                   10                  15

<210> SEQ ID NO 48
<211> LENGTH: 15
<212> TYPE: PRT
<213> ORGANISM: Artificial Sequence
<220> FEATURE:
<221> NAME/KEY: MOD_RES
<222> LOCATION: (1)..(1)
```

-continued

```
<223> OTHER INFORMATION: chemically synthesized

<400> SEQUENCE: 48

Arg Ser Pro Lys Met Val Gln Gly Ser Gly Cys Phe Gly Arg Lys
1               5                   10                  15

<210> SEQ ID NO 49
<211> LENGTH: 15
<212> TYPE: PRT
<213> ORGANISM: Artificial Sequence
<220> FEATURE:
<221> NAME/KEY: MOD_RES
<222> LOCATION: (1)..(1)
<223> OTHER INFORMATION: chemically synthesized

<400> SEQUENCE: 49

Lys Met Val Gln Gly Ser Gly Cys Phe Gly Arg Lys Met Asp Arg
1               5                   10                  15

<210> SEQ ID NO 50
<211> LENGTH: 15
<212> TYPE: PRT
<213> ORGANISM: Artificial Sequence
<220> FEATURE:
<221> NAME/KEY: MOD_RES
<222> LOCATION: (1)..(1)
<223> OTHER INFORMATION: chemically synthesized

<400> SEQUENCE: 50

Gln Gly Ser Gly Cys Phe Gly Arg Lys Met Asp Arg Ile Ser Ser
1               5                   10                  15

<210> SEQ ID NO 51
<211> LENGTH: 15
<212> TYPE: PRT
<213> ORGANISM: Artificial Sequence
<220> FEATURE:
<221> NAME/KEY: MOD_RES
<222> LOCATION: (1)..(1)
<223> OTHER INFORMATION: chemically synthesized

<400> SEQUENCE: 51

Gly Cys Phe Gly Arg Lys Met Asp Arg Ile Ser Ser Ser Ser Gly
1               5                   10                  15

<210> SEQ ID NO 52
<211> LENGTH: 15
<212> TYPE: PRT
<213> ORGANISM: Artificial Sequence
<220> FEATURE:
<221> NAME/KEY: MOD_RES
<222> LOCATION: (1)..(1)
<223> OTHER INFORMATION: chemically synthesized

<400> SEQUENCE: 52

Gly Arg Lys Met Asp Arg Ile Ser Ser Ser Ser Gly Leu Gly Cys
1               5                   10                  15

<210> SEQ ID NO 53
<211> LENGTH: 15
<212> TYPE: PRT
<213> ORGANISM: Artificial Sequence
<220> FEATURE:
<221> NAME/KEY: MOD_RES
<222> LOCATION: (1)..(1)
<223> OTHER INFORMATION: chemically synthesized

<400> SEQUENCE: 53
```

```
Met Asp Arg Ile Ser Ser Ser Gly Leu Gly Cys Lys Val Leu
1               5                   10                  15
```

<210> SEQ ID NO 54
<211> LENGTH: 15
<212> TYPE: PRT
<213> ORGANISM: Artificial Sequence
<220> FEATURE:
<221> NAME/KEY: MOD_RES
<222> LOCATION: (1)..(1)
<223> OTHER INFORMATION: chemically synthesized

<400> SEQUENCE: 54

```
Ile Ser Ser Ser Ser Gly Leu Gly Cys Lys Val Leu Arg Arg His
1               5                   10                  15
```

<210> SEQ ID NO 55
<211> LENGTH: 15
<212> TYPE: PRT
<213> ORGANISM: Artificial Sequence
<220> FEATURE:
<221> NAME/KEY: MOD_RES
<222> LOCATION: (1)..(1)
<223> OTHER INFORMATION: chemically synthesized

<400> SEQUENCE: 55

```
Ala Thr Leu Arg Ala Pro Arg Ser Pro Lys Met Val Gln Gly Ser
1               5                   10                  15
```

<210> SEQ ID NO 56
<211> LENGTH: 15
<212> TYPE: PRT
<213> ORGANISM: Artificial Sequence
<220> FEATURE:
<221> NAME/KEY: MOD_RES
<222> LOCATION: (1)..(1)
<223> OTHER INFORMATION: chemically synthesized

<400> SEQUENCE: 56

```
Tyr Ala Leu Arg Ala Pro Arg Ser Pro Lys Met Val Gln Gly Ser
1               5                   10                  15
```

<210> SEQ ID NO 57
<211> LENGTH: 15
<212> TYPE: PRT
<213> ORGANISM: Artificial Sequence
<220> FEATURE:
<221> NAME/KEY: MOD_RES
<222> LOCATION: (1)..(1)
<223> OTHER INFORMATION: chemically synthesized

<400> SEQUENCE: 57

```
Tyr Thr Ala Arg Ala Pro Arg Ser Pro Lys Met Val Gln Gly Ser
1               5                   10                  15
```

<210> SEQ ID NO 58
<211> LENGTH: 15
<212> TYPE: PRT
<213> ORGANISM: Artificial Sequence
<220> FEATURE:
<221> NAME/KEY: MOD_RES
<222> LOCATION: (1)..(1)
<223> OTHER INFORMATION: chemically synthesized

<400> SEQUENCE: 58

```
Tyr Thr Leu Ala Ala Pro Arg Ser Pro Lys Met Val Gln Gly Ser
1               5                   10                  15
```

```
<210> SEQ ID NO 59
<211> LENGTH: 15
<212> TYPE: PRT
<213> ORGANISM: Artificial Sequence
<220> FEATURE:
<221> NAME/KEY: MOD_RES
<222> LOCATION: (1)..(1)
<223> OTHER INFORMATION: chemically synthesized

<400> SEQUENCE: 59

Tyr Thr Leu Arg Gly Pro Arg Ser Pro Lys Met Val Gln Gly Ser
1               5                   10                  15

<210> SEQ ID NO 60
<211> LENGTH: 15
<212> TYPE: PRT
<213> ORGANISM: Artificial Sequence
<220> FEATURE:
<221> NAME/KEY: MOD_RES
<222> LOCATION: (1)..(1)
<223> OTHER INFORMATION: chemically synthesized

<400> SEQUENCE: 60

Tyr Thr Leu Arg Ala Ala Arg Ser Pro Lys Met Val Gln Gly Ser
1               5                   10                  15

<210> SEQ ID NO 61
<211> LENGTH: 15
<212> TYPE: PRT
<213> ORGANISM: Artificial Sequence
<220> FEATURE:
<221> NAME/KEY: MOD_RES
<222> LOCATION: (1)..(1)
<223> OTHER INFORMATION: chemically synthesized

<400> SEQUENCE: 61

Tyr Thr Leu Arg Ala Pro Ala Ser Pro Lys Met Val Gln Gly Ser
1               5                   10                  15

<210> SEQ ID NO 62
<211> LENGTH: 15
<212> TYPE: PRT
<213> ORGANISM: Artificial Sequence
<220> FEATURE:
<221> NAME/KEY: MOD_RES
<222> LOCATION: (1)..(1)
<223> OTHER INFORMATION: chemically synthesized

<400> SEQUENCE: 62

Tyr Thr Leu Arg Ala Pro Arg Ala Pro Lys Met Val Gln Gly Ser
1               5                   10                  15

<210> SEQ ID NO 63
<211> LENGTH: 15
<212> TYPE: PRT
<213> ORGANISM: Artificial Sequence
<220> FEATURE:
<221> NAME/KEY: MOD_RES
<222> LOCATION: (1)..(1)
<223> OTHER INFORMATION: chemically synthesized

<400> SEQUENCE: 63

Tyr Thr Leu Arg Ala Pro Arg Ser Ala Lys Met Val Gln Gly Ser
1               5                   10                  15

<210> SEQ ID NO 64
<211> LENGTH: 15
<212> TYPE: PRT
<213> ORGANISM: Artificial Sequence
```

```
<220> FEATURE:
<221> NAME/KEY: MOD_RES
<222> LOCATION: (1)..(1)
<223> OTHER INFORMATION: chemically synthesized

<400> SEQUENCE: 64

Tyr Thr Leu Arg Ala Pro Arg Ser Pro Ala Met Val Gln Gly Ser
1               5                   10                  15

<210> SEQ ID NO 65
<211> LENGTH: 15
<212> TYPE: PRT
<213> ORGANISM: Artificial Sequence
<220> FEATURE:
<221> NAME/KEY: MOD_RES
<222> LOCATION: (1)..(1)
<223> OTHER INFORMATION: chemically synthesized

<400> SEQUENCE: 65

Tyr Thr Leu Arg Ala Pro Arg Ser Pro Lys Ala Val Gln Gly Ser
1               5                   10                  15

<210> SEQ ID NO 66
<211> LENGTH: 15
<212> TYPE: PRT
<213> ORGANISM: Artificial Sequence
<220> FEATURE:
<221> NAME/KEY: MOD_RES
<222> LOCATION: (1)..(1)
<223> OTHER INFORMATION: chemically synthesized

<400> SEQUENCE: 66

Tyr Thr Leu Arg Ala Pro Arg Ser Pro Lys Met Ala Gln Gly Ser
1               5                   10                  15

<210> SEQ ID NO 67
<211> LENGTH: 15
<212> TYPE: PRT
<213> ORGANISM: Artificial Sequence
<220> FEATURE:
<221> NAME/KEY: MOD_RES
<222> LOCATION: (1)..(1)
<223> OTHER INFORMATION: chemically synthesized

<400> SEQUENCE: 67

Tyr Thr Leu Arg Ala Pro Arg Ser Pro Lys Met Val Ala Gly Ser
1               5                   10                  15

<210> SEQ ID NO 68
<211> LENGTH: 15
<212> TYPE: PRT
<213> ORGANISM: Artificial Sequence
<220> FEATURE:
<221> NAME/KEY: MOD_RES
<222> LOCATION: (1)..(1)
<223> OTHER INFORMATION: chemically synthesized

<400> SEQUENCE: 68

Tyr Thr Leu Arg Ala Pro Arg Ser Pro Lys Met Val Gln Ala Ser
1               5                   10                  15

<210> SEQ ID NO 69
<211> LENGTH: 15
<212> TYPE: PRT
<213> ORGANISM: Artificial Sequence
<220> FEATURE:
<221> NAME/KEY: MOD_RES
<222> LOCATION: (1)..(1)
<223> OTHER INFORMATION: chemically synthesized
```

```
<400> SEQUENCE: 69

Tyr Thr Leu Arg Ala Pro Arg Ser Pro Lys Met Val Gln Gly Ala
1               5                   10                  15

<210> SEQ ID NO 70
<211> LENGTH: 15
<212> TYPE: PRT
<213> ORGANISM: Artificial Sequence
<220> FEATURE:
<221> NAME/KEY: MOD_RES
<222> LOCATION: (1)..(1)
<223> OTHER INFORMATION: chemically synthesized

<400> SEQUENCE: 70

Pro Leu Gly Ser Pro Gly Ser Ala Ser Asp Leu Glu Thr Ser Gly
1               5                   10                  15

<210> SEQ ID NO 71
<211> LENGTH: 15
<212> TYPE: PRT
<213> ORGANISM: Artificial Sequence
<220> FEATURE:
<221> NAME/KEY: MOD_RES
<222> LOCATION: (1)..(1)
<223> OTHER INFORMATION: chemically synthesized

<400> SEQUENCE: 71

Leu Gly Ser Pro Gly Ser Ala Ser Asp Leu Glu Thr Ser Gly Leu
1               5                   10                  15

<210> SEQ ID NO 72
<211> LENGTH: 15
<212> TYPE: PRT
<213> ORGANISM: Artificial Sequence
<220> FEATURE:
<221> NAME/KEY: MOD_RES
<222> LOCATION: (1)..(1)
<223> OTHER INFORMATION: chemically synthesized

<400> SEQUENCE: 72

Ser Pro Gly Ser Ala Ser Asp Leu Glu Thr Ser Gly Leu Gln Glu
1               5                   10                  15

<210> SEQ ID NO 73
<211> LENGTH: 15
<212> TYPE: PRT
<213> ORGANISM: Artificial Sequence
<220> FEATURE:
<221> NAME/KEY: MOD_RES
<222> LOCATION: (1)..(1)
<223> OTHER INFORMATION: chemically synthesized

<400> SEQUENCE: 73

Pro Gly Ser Ala Ser Asp Leu Glu Thr Ser Gly Leu Gln Glu Gln
1               5                   10                  15

<210> SEQ ID NO 74
<211> LENGTH: 15
<212> TYPE: PRT
<213> ORGANISM: Artificial Sequence
<220> FEATURE:
<221> NAME/KEY: MOD_RES
<222> LOCATION: (1)..(1)
<223> OTHER INFORMATION: chemically synthesized

<400> SEQUENCE: 74

Ser Ala Ser Asp Leu Glu Thr Ser Gly Leu Gln Glu Gln Arg Asn
```

```
1               5                   10                  15
```

<210> SEQ ID NO 75
<211> LENGTH: 15
<212> TYPE: PRT
<213> ORGANISM: Artificial Sequence
<220> FEATURE:
<221> NAME/KEY: MOD_RES
<222> LOCATION: (1)..(1)
<223> OTHER INFORMATION: chemically synthesized

<400> SEQUENCE: 75

```
Ala Ser Asp Leu Glu Thr Ser Gly Leu Gln Glu Gln Arg Asn His
1               5                   10                  15
```

<210> SEQ ID NO 76
<211> LENGTH: 15
<212> TYPE: PRT
<213> ORGANISM: Artificial Sequence
<220> FEATURE:
<221> NAME/KEY: MOD_RES
<222> LOCATION: (1)..(1)
<223> OTHER INFORMATION: chemically synthesized

<400> SEQUENCE: 76

```
Ser Asp Leu Glu Thr Ser Gly Leu Gln Glu Gln Arg Asn His Leu
1               5                   10                  15
```

<210> SEQ ID NO 77
<211> LENGTH: 15
<212> TYPE: PRT
<213> ORGANISM: Artificial Sequence
<220> FEATURE:
<221> NAME/KEY: MOD_RES
<222> LOCATION: (1)..(1)
<223> OTHER INFORMATION: chemically synthesized

<400> SEQUENCE: 77

```
Asp Leu Glu Thr Ser Gly Leu Gln Glu Gln Arg Asn His Leu Gln
1               5                   10                  15
```

<210> SEQ ID NO 78
<211> LENGTH: 15
<212> TYPE: PRT
<213> ORGANISM: Artificial Sequence
<220> FEATURE:
<221> NAME/KEY: MOD_RES
<222> LOCATION: (1)..(1)
<223> OTHER INFORMATION: chemically synthesized

<400> SEQUENCE: 78

```
Leu Glu Thr Ser Gly Leu Gln Glu Gln Arg Asn His Leu Gln Gly
1               5                   10                  15
```

<210> SEQ ID NO 79
<211> LENGTH: 15
<212> TYPE: PRT
<213> ORGANISM: Artificial Sequence
<220> FEATURE:
<221> NAME/KEY: MOD_RES
<222> LOCATION: (1)..(1)
<223> OTHER INFORMATION: chemically synthesized

<400> SEQUENCE: 79

```
Leu Gln Glu Gln Arg Asn His Leu Gln Gly Lys Leu Ser Glu Leu
1               5                   10                  15
```

<210> SEQ ID NO 80

```
<211> LENGTH: 15
<212> TYPE: PRT
<213> ORGANISM: Artificial Sequence
<220> FEATURE:
<221> NAME/KEY: MOD_RES
<222> LOCATION: (1)..(1)
<223> OTHER INFORMATION: chemically synthesized

<400> SEQUENCE: 80

Gln Glu Gln Arg Asn His Leu Gln Gly Lys Leu Ser Glu Leu Gln
1               5                   10                  15

<210> SEQ ID NO 81
<211> LENGTH: 15
<212> TYPE: PRT
<213> ORGANISM: Artificial Sequence
<220> FEATURE:
<221> NAME/KEY: MOD_RES
<222> LOCATION: (1)..(1)
<223> OTHER INFORMATION: chemically synthesized

<400> SEQUENCE: 81

Gln Arg Asn His Leu Gln Gly Lys Leu Ser Glu Leu Gln Val Glu
1               5                   10                  15

<210> SEQ ID NO 82
<211> LENGTH: 15
<212> TYPE: PRT
<213> ORGANISM: Artificial Sequence
<220> FEATURE:
<221> NAME/KEY: MOD_RES
<222> LOCATION: (1)..(1)
<223> OTHER INFORMATION: chemically synthesized

<400> SEQUENCE: 82

Arg Asn His Leu Gln Gly Lys Leu Ser Glu Leu Gln Val Glu Gln
1               5                   10                  15

<210> SEQ ID NO 83
<211> LENGTH: 15
<212> TYPE: PRT
<213> ORGANISM: Artificial Sequence
<220> FEATURE:
<221> NAME/KEY: MOD_RES
<222> LOCATION: (1)..(1)
<223> OTHER INFORMATION: chemically synthesized

<400> SEQUENCE: 83

His Leu Gln Gly Lys Leu Ser Glu Leu Gln Val Glu Gln Thr Ser
1               5                   10                  15

<210> SEQ ID NO 84
<211> LENGTH: 15
<212> TYPE: PRT
<213> ORGANISM: Artificial Sequence
<220> FEATURE:
<221> NAME/KEY: MOD_RES
<222> LOCATION: (1)..(1)
<223> OTHER INFORMATION: chemically synthesized

<400> SEQUENCE: 84

Leu Gln Gly Lys Leu Ser Glu Leu Gln Val Glu Gln Thr Ser Leu
1               5                   10                  15

<210> SEQ ID NO 85
<211> LENGTH: 15
<212> TYPE: PRT
<213> ORGANISM: Artificial Sequence
<220> FEATURE:
```

```
<221> NAME/KEY: MOD_RES
<222> LOCATION: (1)..(1)
<223> OTHER INFORMATION: chemically synthesized

<400> SEQUENCE: 85

Gln Gly Lys Leu Ser Glu Leu Gln Val Glu Gln Thr Ser Leu Glu
1               5                   10                  15

<210> SEQ ID NO 86
<211> LENGTH: 15
<212> TYPE: PRT
<213> ORGANISM: Artificial Sequence
<220> FEATURE:
<221> NAME/KEY: MOD_RES
<222> LOCATION: (1)..(1)
<223> OTHER INFORMATION: chemically synthesized

<400> SEQUENCE: 86

Gly Lys Leu Ser Glu Leu Gln Val Glu Gln Thr Ser Leu Glu Pro
1               5                   10                  15

<210> SEQ ID NO 87
<211> LENGTH: 15
<212> TYPE: PRT
<213> ORGANISM: Artificial Sequence
<220> FEATURE:
<221> NAME/KEY: MOD_RES
<222> LOCATION: (1)..(1)
<223> OTHER INFORMATION: chemically synthesized

<400> SEQUENCE: 87

Lys Leu Ser Glu Leu Gln Val Glu Gln Thr Ser Leu Glu Pro Leu
1               5                   10                  15

<210> SEQ ID NO 88
<211> LENGTH: 15
<212> TYPE: PRT
<213> ORGANISM: Artificial Sequence
<220> FEATURE:
<221> NAME/KEY: MOD_RES
<222> LOCATION: (1)..(1)
<223> OTHER INFORMATION: chemically synthesized

<400> SEQUENCE: 88

Leu Glu Pro Leu Gln Glu Ser Pro Arg Pro Thr Gly Val Trp Lys
1               5                   10                  15

<210> SEQ ID NO 89
<211> LENGTH: 15
<212> TYPE: PRT
<213> ORGANISM: Artificial Sequence
<220> FEATURE:
<221> NAME/KEY: MOD_RES
<222> LOCATION: (1)..(1)
<223> OTHER INFORMATION: chemically synthesized

<400> SEQUENCE: 89

Glu Pro Leu Gln Glu Ser Pro Arg Pro Thr Gly Val Trp Lys Ser
1               5                   10                  15

<210> SEQ ID NO 90
<211> LENGTH: 15
<212> TYPE: PRT
<213> ORGANISM: Artificial Sequence
<220> FEATURE:
<221> NAME/KEY: MOD_RES
<222> LOCATION: (1)..(1)
<223> OTHER INFORMATION: chemically synthesized
```

```
<400> SEQUENCE: 90

Pro Leu Gln Glu Ser Pro Arg Pro Thr Gly Val Trp Lys Ser Arg
1               5                   10                  15

<210> SEQ ID NO 91
<211> LENGTH: 15
<212> TYPE: PRT
<213> ORGANISM: Artificial Sequence
<220> FEATURE:
<221> NAME/KEY: MOD_RES
<222> LOCATION: (1)..(1)
<223> OTHER INFORMATION: chemically synthesized

<400> SEQUENCE: 91

Leu Gln Glu Ser Pro Arg Pro Thr Gly Val Trp Lys Ser Arg Glu
1               5                   10                  15

<210> SEQ ID NO 92
<211> LENGTH: 15
<212> TYPE: PRT
<213> ORGANISM: Artificial Sequence
<220> FEATURE:
<221> NAME/KEY: MOD_RES
<222> LOCATION: (1)..(1)
<223> OTHER INFORMATION: chemically synthesized

<400> SEQUENCE: 92

Gln Glu Ser Pro Arg Pro Thr Gly Val Trp Lys Ser Arg Glu Val
1               5                   10                  15

<210> SEQ ID NO 93
<211> LENGTH: 15
<212> TYPE: PRT
<213> ORGANISM: Artificial Sequence
<220> FEATURE:
<221> NAME/KEY: MOD_RES
<222> LOCATION: (1)..(1)
<223> OTHER INFORMATION: chemically synthesized

<400> SEQUENCE: 93

Glu Ser Pro Arg Pro Thr Gly Val Trp Lys Ser Arg Glu Val Ala
1               5                   10                  15

<210> SEQ ID NO 94
<211> LENGTH: 15
<212> TYPE: PRT
<213> ORGANISM: Artificial Sequence
<220> FEATURE:
<221> NAME/KEY: MOD_RES
<222> LOCATION: (1)..(1)
<223> OTHER INFORMATION: chemically synthesized

<400> SEQUENCE: 94

Ser Pro Arg Pro Thr Gly Val Trp Lys Ser Arg Glu Val Ala Thr
1               5                   10                  15

<210> SEQ ID NO 95
<211> LENGTH: 15
<212> TYPE: PRT
<213> ORGANISM: Artificial Sequence
<220> FEATURE:
<221> NAME/KEY: MOD_RES
<222> LOCATION: (1)..(1)
<223> OTHER INFORMATION: chemically synthesized

<400> SEQUENCE: 95

Pro Arg Pro Thr Gly Val Trp Lys Ser Arg Glu Val Ala Thr Glu
1               5                   10                  15
```

```
<210> SEQ ID NO 96
<211> LENGTH: 15
<212> TYPE: PRT
<213> ORGANISM: Artificial Sequence
<220> FEATURE:
<221> NAME/KEY: MOD_RES
<222> LOCATION: (1)..(1)
<223> OTHER INFORMATION: chemically synthesized

<400> SEQUENCE: 96

Pro Thr Gly Val Trp Lys Ser Arg Glu Val Ala Thr Glu Gly Ile
1               5                   10                  15

<210> SEQ ID NO 97
<211> LENGTH: 15
<212> TYPE: PRT
<213> ORGANISM: Artificial Sequence
<220> FEATURE:
<221> NAME/KEY: MOD_RES
<222> LOCATION: (1)..(1)
<223> OTHER INFORMATION: chemically synthesized

<400> SEQUENCE: 97

Thr Gly Val Trp Lys Ser Arg Glu Val Ala Thr Glu Gly Ile Arg
1               5                   10                  15

<210> SEQ ID NO 98
<211> LENGTH: 15
<212> TYPE: PRT
<213> ORGANISM: Artificial Sequence
<220> FEATURE:
<221> NAME/KEY: MOD_RES
<222> LOCATION: (1)..(1)
<223> OTHER INFORMATION: chemically synthesized

<400> SEQUENCE: 98

Ile Arg Gly His Arg Lys Met Val Leu Tyr Thr Leu Arg Ala Pro
1               5                   10                  15

<210> SEQ ID NO 99
<211> LENGTH: 15
<212> TYPE: PRT
<213> ORGANISM: Artificial Sequence
<220> FEATURE:
<221> NAME/KEY: MOD_RES
<222> LOCATION: (1)..(1)
<223> OTHER INFORMATION: chemically synthesized

<400> SEQUENCE: 99

Arg Gly His Arg Lys Met Val Leu Tyr Thr Leu Arg Ala Pro Arg
1               5                   10                  15

<210> SEQ ID NO 100
<211> LENGTH: 15
<212> TYPE: PRT
<213> ORGANISM: Artificial Sequence
<220> FEATURE:
<221> NAME/KEY: MOD_RES
<222> LOCATION: (1)..(1)
<223> OTHER INFORMATION: chemically synthesized

<400> SEQUENCE: 100

Gly His Arg Lys Met Val Leu Tyr Thr Leu Arg Ala Pro Arg Ser
1               5                   10                  15

<210> SEQ ID NO 101
<211> LENGTH: 15
```

-continued

```
<212> TYPE: PRT
<213> ORGANISM: Artificial Sequence
<220> FEATURE:
<221> NAME/KEY: MOD_RES
<222> LOCATION: (1)..(1)
<223> OTHER INFORMATION: chemically synthesized

<400> SEQUENCE: 101

Arg Lys Met Val Leu Tyr Thr Leu Arg Ala Pro Arg Ser Pro Lys
1               5                   10                  15

<210> SEQ ID NO 102
<211> LENGTH: 15
<212> TYPE: PRT
<213> ORGANISM: Artificial Sequence
<220> FEATURE:
<221> NAME/KEY: MOD_RES
<222> LOCATION: (1)..(1)
<223> OTHER INFORMATION: chemically synthesized

<400> SEQUENCE: 102

Lys Met Val Leu Tyr Thr Leu Arg Ala Pro Arg Ser Pro Lys Met
1               5                   10                  15

<210> SEQ ID NO 103
<211> LENGTH: 15
<212> TYPE: PRT
<213> ORGANISM: Artificial Sequence
<220> FEATURE:
<221> NAME/KEY: MOD_RES
<222> LOCATION: (1)..(1)
<223> OTHER INFORMATION: chemically synthesized

<400> SEQUENCE: 103

Val Leu Tyr Thr Leu Arg Ala Pro Arg Ser Pro Lys Met Val Gln
1               5                   10                  15

<210> SEQ ID NO 104
<211> LENGTH: 35
<212> TYPE: PRT
<213> ORGANISM: Artificial Sequence
<220> FEATURE:
<221> NAME/KEY: MOD_RES
<222> LOCATION: (1)..(1)
<223> OTHER INFORMATION: chemically synthesized

<400> SEQUENCE: 104

Ser Pro Lys Met Val Gln Gly Ser Gly Cys Phe Gly Arg Lys Met Asp
1               5                   10                  15

Arg Ile Ser Ser Ser Ser Gly Leu Gly Cys Lys Val Leu Arg Arg His
                20                  25                  30

Lys Lys Lys
        35

<210> SEQ ID NO 105
<211> LENGTH: 10
<212> TYPE: PRT
<213> ORGANISM: Artificial Sequence
<220> FEATURE:
<221> NAME/KEY: misc_feature
<223> OTHER INFORMATION: peptide

<400> SEQUENCE: 105

Ser Pro Lys Met Val Gln Gly Ser Gly Cys
1               5                   10

<210> SEQ ID NO 106
```

```
<211> LENGTH: 12
<212> TYPE: PRT
<213> ORGANISM: Artificial Sequence
<220> FEATURE:
<221> NAME/KEY: misc_feature
<223> OTHER INFORMATION: peptide

<400> SEQUENCE: 106

Arg Lys Met Val Leu Tyr Thr Leu Arg Ala Pro Arg
1               5                   10

<210> SEQ ID NO 107
<211> LENGTH: 13
<212> TYPE: PRT
<213> ORGANISM: Artificial Sequence
<220> FEATURE:
<221> NAME/KEY: misc_feature
<223> OTHER INFORMATION: peptide

<400> SEQUENCE: 107

His Arg Lys Met Val Leu Tyr Thr Leu Arg Ala Pro Arg
1               5                   10

<210> SEQ ID NO 108
<211> LENGTH: 15
<212> TYPE: PRT
<213> ORGANISM: Artificial Sequence
<220> FEATURE:
<221> NAME/KEY: misc_feature
<223> OTHER INFORMATION: peptide

<400> SEQUENCE: 108

Tyr Thr Leu Arg Ala Pro Arg Ser Pro Lys Met Val Gln Gly Ser
1               5                   10                  15

<210> SEQ ID NO 109
<211> LENGTH: 16
<212> TYPE: PRT
<213> ORGANISM: Artificial Sequence
<220> FEATURE:
<221> NAME/KEY: misc_feature
<223> OTHER INFORMATION: peptide

<400> SEQUENCE: 109

Cys Tyr Thr Leu Arg Ala Pro Arg Ser Pro Lys Met Val Gln Gly Ser
1               5                   10                  15

<210> SEQ ID NO 110
<211> LENGTH: 11
<212> TYPE: PRT
<213> ORGANISM: Artificial Sequence
<220> FEATURE:
<221> NAME/KEY: misc_feature
<223> OTHER INFORMATION: peptide

<400> SEQUENCE: 110

Cys Tyr Thr Leu Arg Ala Pro Arg Ser Pro Lys
1               5                   10

<210> SEQ ID NO 111
<211> LENGTH: 13
<212> TYPE: PRT
<213> ORGANISM: Artificial Sequence
<220> FEATURE:
<221> NAME/KEY: misc_feature
<223> OTHER INFORMATION: peptide

<400> SEQUENCE: 111
```

Cys Tyr Thr Leu Arg Ala Pro Arg Ser Pro Lys Met Val
1               5                   10

<210> SEQ ID NO 112
<211> LENGTH: 14
<212> TYPE: PRT
<213> ORGANISM: Artificial Sequence
<220> FEATURE:
<221> NAME/KEY: misc_feature
<223> OTHER INFORMATION: peptide

<400> SEQUENCE: 112

Cys Tyr Thr Leu Arg Ala Pro Arg Ser Pro Lys Met Val Gln
1               5                   10

<210> SEQ ID NO 113
<211> LENGTH: 15
<212> TYPE: PRT
<213> ORGANISM: Artificial Sequence
<220> FEATURE:
<221> NAME/KEY: misc_feature
<223> OTHER INFORMATION: peptide

<400> SEQUENCE: 113

Cys Tyr Thr Leu Arg Ala Pro Arg Ser Pro Lys Met Val Gln Gly
1               5                   10                  15

<210> SEQ ID NO 114
<211> LENGTH: 13
<212> TYPE: PRT
<213> ORGANISM: Artificial Sequence
<220> FEATURE:
<221> NAME/KEY: MOD_RES
<222> LOCATION: (1)..(1)
<223> OTHER INFORMATION: chemically synthesized

<400> SEQUENCE: 114

Cys Thr Leu Arg Ala Pro Arg Ser Pro Lys Met Val Gln
1               5                   10

<210> SEQ ID NO 115
<211> LENGTH: 14
<212> TYPE: PRT
<213> ORGANISM: Artificial Sequence
<220> FEATURE:
<221> NAME/KEY: misc_feature
<223> OTHER INFORMATION: peptide

<400> SEQUENCE: 115

Cys Thr Leu Arg Ala Pro Arg Ser Pro Lys Met Val Gln Gly
1               5                   10

<210> SEQ ID NO 116
<211> LENGTH: 15
<212> TYPE: PRT
<213> ORGANISM: Artificial Sequence
<220> FEATURE:
<221> NAME/KEY: misc_feature
<223> OTHER INFORMATION: peptide

<400> SEQUENCE: 116

Cys Thr Leu Arg Ala Pro Arg Ser Pro Lys Met Val Gln Gly Ser
1               5                   10                  15

<210> SEQ ID NO 117
<211> LENGTH: 16
<212> TYPE: PRT
<213> ORGANISM: Artificial Sequence

```
<220> FEATURE:
<221> NAME/KEY: misc_feature
<223> OTHER INFORMATION: peptide

<400> SEQUENCE: 117

Cys Thr Leu Arg Ala Pro Arg Ser Pro Lys Met Val Gln Gly Ser Gly
1               5                   10                  15

<210> SEQ ID NO 118
<211> LENGTH: 11
<212> TYPE: PRT
<213> ORGANISM: Artificial Sequence
<220> FEATURE:
<221> NAME/KEY: misc_feature
<223> OTHER INFORMATION: peptide

<400> SEQUENCE: 118

Cys Leu Arg Ala Pro Arg Ser Pro Lys Met Val
1               5                   10

<210> SEQ ID NO 119
<211> LENGTH: 12
<212> TYPE: PRT
<213> ORGANISM: Artificial Sequence
<220> FEATURE:
<221> NAME/KEY: misc_feature
<223> OTHER INFORMATION: peptide

<400> SEQUENCE: 119

Cys Leu Arg Ala Pro Arg Ser Pro Lys Met Val Gln
1               5                   10

<210> SEQ ID NO 120
<211> LENGTH: 12
<212> TYPE: PRT
<213> ORGANISM: Artificial Sequence
<220> FEATURE:
<221> NAME/KEY: misc_feature
<223> OTHER INFORMATION: peptide

<400> SEQUENCE: 120

Leu Arg Ala Pro Arg Ser Pro Lys Met Val Gln Cys
1               5                   10

<210> SEQ ID NO 121
<211> LENGTH: 14
<212> TYPE: PRT
<213> ORGANISM: Artificial Sequence
<220> FEATURE:
<221> NAME/KEY: misc_feature
<223> OTHER INFORMATION: peptide

<400> SEQUENCE: 121

Cys Leu Arg Ala Pro Arg Ser Pro Lys Met Val Gln Gly Ser
1               5                   10

<210> SEQ ID NO 122
<211> LENGTH: 15
<212> TYPE: PRT
<213> ORGANISM: Artificial Sequence
<220> FEATURE:
<221> NAME/KEY: misc_feature
<223> OTHER INFORMATION: peptide

<400> SEQUENCE: 122

Cys Leu Arg Ala Pro Arg Ser Pro Lys Met Val Gln Gly Ser Gly
1               5                   10                  15
```

```
<210> SEQ ID NO 123
<211> LENGTH: 11
<212> TYPE: PRT
<213> ORGANISM: Artificial Sequence
<220> FEATURE:
<221> NAME/KEY: misc_feature
<223> OTHER INFORMATION: peptide

<400> SEQUENCE: 123

Leu Gln Glu Gln Arg Asn His Leu Gln Gly Lys
1               5                   10

<210> SEQ ID NO 124
<211> LENGTH: 12
<212> TYPE: PRT
<213> ORGANISM: Artificial Sequence
<220> FEATURE:
<221> NAME/KEY: misc_feature
<223> OTHER INFORMATION: peptide

<400> SEQUENCE: 124

Leu Glu Pro Leu Gln Glu Ser Pro Arg Pro Thr Gly
1               5                   10
```

SPECIFIC ANTIBODIES FOR DIAGNOSING HEART FAILURE

This is a 371 of PCT/FR03/002483, filed 7 Aug. 2003.

The invention relates to the field of the in vitro diagnosis of ventricular heart failure.

Congestive heart failure is a common clinical syndrome, in particular in elderly individuals. It usually presents in the form of an insidious triggering of nonspecific symptoms such as coughing with exercise, fatigue, and the appearance of peripheral edemas. Diagnosis is conventionally based on the study of various parameters, such as clinical signs, (classified in four stages: stages I to IV of the NYHA (i.e. of the New York Heart Association), echocardiography, scintigraphy, exercise tests, etc.

Due to the seriousness of heart disease, and also to the high costs of treating it, an early diagnosis of this syndrome is, obviously, extremely desirable: it would contribute to preventing the rapid progression of the syndrome to severe heart failure. Identifying the individuals at risk of heart failure is therefore a necessity. This would also make it possible to adapt a faster, easier and less expensive therapeutic monitoring. Unfortunately, no method for diagnosing heart failure exists that is entirely satisfactory and completely informative.

Presymptomatic markers that predict heart failure have been sought for a long time. In this regard, the fact that cardiomyocytes produce and secrete peptides with natriuretic activity has been demonstrated: a peptide of atrial origin, ANP (atrial natriuretic peptide) discovered in rats by Bold et al. *Life Science* 1981, vol. 28(1): 89-94, and a natriuretic peptide of atrioventricular origin called BNP (brain natriuretic peptide) discovered by Sudoh et al., *Nature* 1988, vol. 332: 78-81 in pigs, and then in humans.

The BNP precursor is preproBNP(1-134), which is a storage form of the molecule in cardiomyocytes. This precursor is cleaved so as to release a signal peptide and proBNP(1-108). proBNP(1-108) consists of a 108 amino acid polypeptide, of sequence:
$H_1$PLGSPGSASDLETSGLQEQRNHLQGKLSELQVEQT SLEPLQESPRPTGVWKSRE VATEGIRGHRKMVLYTLRAPR$_{76}$S$_{77}$PKMVQGSGCFG RKMDRISSSSGLGCKVLRRH$_{108}$ (SEQ ID No. 1). It is cleaved, before and/or during its secretion, between the amino acids Arg$^{76}$ and Ser$^{77}$, to, firstly, BNP, also referred to as BNP(77-108) or BNP-32, or even BNP(1-32) and the N-terminal portion of the prohormone, BNP(1-76), also referred to as N-terminal fragment of proBNP or NT-proBNP.

BNP or BNP(77-108), a vasoreactive form of the molecule, consists of a 32 amino acid peptide, of sequence:

(SEQ ID No. 2)
$S_{77}$PKMVQGSGCFGRKMDRISSSSGLGCKVLRRH$_{108}$.

NT-proBNP or BNP(1-76) consists of the 76 N-terminal amino acids of proBNP(1-108) constituting the following sequence:

(SEQ ID No. 3)
$H_1$PLGSPGSASDLETSGLQEQRNHLQGKLSELQVEQTSLEPLQESPRPTG VWKSREVATEGIRGHRKMVLYTLRAPR$_{76}$.

The level of hormonal BNP, BNP(77-108), in the blood is high in patients exhibiting ventricular dystrophy. Assays for BNP(77-108) in the plasma have, moreover, been described, using it as a marker for predicting ventricular heart failure. However, it is well known that the hormone BNP(77-108) is relatively unstable. As a result of this, the assaying thereof requires particular precautions (Davidson, N. C. et al. Circulation 1995; 91:1276) (Gobinet-Georges et al. Clin. Chem. Lab. Med. 2000; 38:519-23). In addition, the half-life of BNP is very short and its plasma concentration is not very high. As a result of this, a certain number of false-negative results are observed in individuals at risk of heart failure. Thus, the assaying of BNP(77-108) does not make it possible to correctly discriminate between patients in stage I of the NYHA classification and normal individuals (Clerico A. et al. J. Endocrinol. Invest. 1998; 21:170-9) (Del Ry S, et al. Scand. J. Clin. Lab. Invest. 2000; 60:81-90).

In order to circumvent this difficulty, patent application WO 93/24531 describes a method of in vitro diagnosis of heart failure based on the detection of BNP(1-76) (N-terminal fragment of proBNP), an abundant compound which has a long half-life compared with that of the BNP(77-108) hormone. However, the method described in application WO 93/24531 does not appear to be simple to carry out on BNP (1-76) in blood samples. In fact, the only examples shown are carried out, not on real sera, but on standard ranges obtained using a synthetic peptide, the peptide BNP(47-64), a subsequence of BNP(1-76). To overcome this drawback, a highly sophisticated automated system has since proven necessary.

The article Hunt et al., *Biochemical and Biophysical Research Communications*, vol. 214(3), 1995, pp. 1175-1183 describes a competitive RIA assay for BNP on plasmas from patients suffering from heart failure, involving an antiserum directed against the N-terminal fragment of proBNP(1-13). The article shows precisely that, in heart failure patients, the level of BNP(1-76), which correlates very well with that of BNP(77-108), is considerably higher than the level observed in control individuals. However, the protocol described for specifically extracting only plasma BNP(1-76) is complex since it requires extraction of the plasma on a Sep-pak C18™ cartridge (Millipore-Waters), followed by HPLC chromatography. Moreover, this article emphasizes that, in the RIA assay thus used, proBNP(1-108) does not appear to be recognized. It suggests rather that proBNP(1-108) could be secreted into the circulation from the heart tissue, but might then be rapidly degraded to a smaller peptide, by cleavage of the N-terminal acids. Alternatively, according to the article, proBNP(1-108) may be present in such a way that the anti-proBNP(1-108) antiserum is incapable of binding to it. Finally, they also suggest that BNP(1-76) (N-terminal fragment of proBNP) could even be a more specific marker for cardiac dysfunction than BNP(77-108) or than the N-terminal fragment of proANP.

The article Karl et al. (*Scand. J. Clin. Lab. Invest.* 1999; 59(suppl 230): 177-181) describes a method for detecting BNP(1-76) that is similar to that of patent application WO 93/24531, but it does not provide any results obtained on samples from patients.

The article Schulz et al., *Scand. J. Clin. Lab. Invest.*, 2001, vol. 61, pp. 33-42, also describes a radioimmunoassay specific for BNP(1-76) (N-terminal fragment of proBNP), without extraction, using an antiserum directed against amino acids 1-21 of this fragment. The authors confirm the advantage of the BNP(1-76) assay in the diagnosis of ventricular heart failure and also the good correlation thereof with the assaying of BNP(77-108). In a study of the various circulating forms of proBNP(1-108), they put forward the hypothesis that proBNP(1-108) would circulate in the blood both in the form of intact prohormone and in the form of cleavage products, BNP(1-76) (N-terminal fragment of proBNP) and BNP (77-108). However, there is no mention or suggestion in the article regarding any possible physiological activity of the proBNP(1-108) or any diagnostic value of proBNP(1-108) as a predictive or diagnostic marker for ventricular heart failure.

The article Shimizu et al. *Clinica Chimica Acta*, 2002, vol. 316, pp. 129-135, presents a study on the degradation of human BNP in the blood and the circulating molecular forms of immunoreactive BNP in the plasma of heart failure patients. It observes, in the plasma of the latter, the presence of two immunoreactive BNP forms: a high molecular weight BNP (36 KD, which could correspond to a trimer of proBNP (1-108)) and a low molecular weight BNP. The latter corresponds to the simultaneous presence of a form of degradation product of BNP-32 having lost the N-terminal serine and proline (i.e. des-SerPro-BNP(BNP3-32)) of the hormonal form of BNP-32 (here referred to as BNP(1-32)). proBNP(1-108) and hormonal BNP(BNP-32, BNP(1-32) or alternatively BNP(77-108)) are therefore secreted by the heart into the blood. However, the authors appear to suggest that proBNP(1-108) in its oligomerized form (trimer) is present at a concentration similar to that of the circulating BNP(77-108), but they do not measure it. Consequently, the correlation between the concentration of proBNP(1-108) and the clinical condition of the patients is not studied. It ensues that the diagnostic or prognostic value of serum proBNP(1-108) is not demonstrated therein; neither is it suggested that it is possible to assay the latter routinely.

Moreover, a certain number of epitopes present on proBNP (1-108) are known. Thus, in the context of the detection of BNP(77-108), the epitope of sequence $S_{77}PKMVQGSGC_{86}$ (SEQ ID No. 105) corresponding to the 10 N-terminal amino acids (AA 1-10) of BNP(77-108) is described in application WO 97/32900. Similarly, in the context of the detection of BNP(1-76) (N-terminal fragment of proBNP), the epitope of sequence $R_{65}KMVLYTLRAPR_{76}$ (SEQ ID No. 106) corresponding to the 12 C-terminal amino acids of BNP(1-76) (N-terminal fragment of proBNP) is described in application WO 00/35951, and a similar sequence $H_{64}RKMVLYTLRAPR_{76}$ (SEQ ID No. 107) is described in application WO 00/45176. However, none of these patent applications either describes or suggests the existence of an epitope that is an intermediate or hybrid between these sequences.

There therefore still exists a need, in the context of the early diagnosis of heart failure, to have a method which avoids the drawbacks of the prior art. In particular, there is a need for a simple method that can be used routinely and is reliable, and that avoids the drawbacks of the detection of BNP(77-108), a molecule that is not very abundant and is relatively unstable, while at the same time avoiding the complex extractions brought about by the assaying of other molecular forms of BNP and that can possibly go as far as requiring a sophisticated automation.

The authors of the present invention have therefore endeavored to develop an alternative method in order to solve the problem posed. At the center of the present invention is the unexpected discovery, made by the inventors, of an epitope with unique properties located in the domain of the hinge sequence $Y_{70}TLRAPR_{76}S_{77}PKMVQGSG_{85}$ (SEQ ID No. 4) or of the sequence $Y_{70}TLRAPR_{76}S_{77}PKMVQGS_{84}$ (SEQ ID No. 108) of proBNP(1-108) and comprising at least the sequence $RAPR_{76}S_{77}P$ (SEQ ID No. 5).

In fact, when rabbits were immunized with a peptide of the hinged region of proBNP(1-108), of sequence $CY_{70}TLRAPR_{76}S_{77}PKMVQGSG_{85}$ (SEQ ID No. 16) or alternatively with the peptide of sequence $CY_{70}TLRAPR_{76}S_{77}PKMVQGS_{84}$ (SEQ ID No. 109), they discovered, surprisingly, that the antiserum obtained not only contained antibodies which specifically recognized said peptide of the hinge region without substantially recognizing the BNP(1-76) and BNP(77-108) forms, but in addition have the ability to recognize circulating proBNP(1-108).

The authors of the present application have also shown, for the first time, that circulating proBNP(1-108) is effectively a marker for predicting heart failure and that it is present at a concentration that is significantly higher in heart failure patients than in normal control individuals.

The authors have also discovered that another way to obtain this type of antibody is to immunize animals using the complete proBNP(1-108) molecule. In fact, the authors have found that immunization with the complete proBNP(1-108) molecule makes it possible to induce the appearance of antibodies that specifically recognize a sequence of the hinge region.

In addition, the authors of the present invention have demonstrated that the minimum epitope recognized by the antibodies according to the invention has the following sequence: $RAPR_{76}S_{77}P$. They have also shown that a successful way of obtaining the antibodies which are the subject of the present invention is to immunize animals with a peptide of general formula:

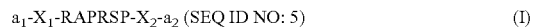
$a_1$-$X_1$-RAPRSP-$X_2$-$a_2$ (SEQ ID NO: 5)     (I)

where $a_1$ may be H or may represent a function or a chemical group chosen from a thiol, alcohol, aminoxy, primary amine or secondary amine function, an aminocarboxyl group, a biotinyl group and an acetyl group, $X_1$ represents a peptide sequence of 0 to 3 amino acids, which may or may not be derived from the natural sequence of proBNP(1-108), $X_2$ represents a peptide sequence of 0 to 8 amino acids, preferably 7 amino acids, which may or may not be derived from the natural sequence of proBNP(1-108), $a_2$ may represent an OH function, an $NH_2$ function, or an alkoxyl group.

Similarly, the authors of the present invention have shown that it is possible to obtain the same specific antibodies by immunizing an animal with a peptide comprising the sequence $RAPR_{76}S_{77}P$ (SEQ ID NO: 5) or with a peptide of formula:

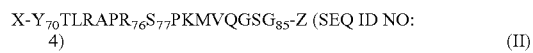
X-$Y_{70}$TLRAPR$_{76}$S$_{77}$PKMVQGSG$_{85}$-Z (SEQ ID NO: 4)     (II)

where X may be H or may represent either an acetyl group, or 1 to 3 amino acids not belonging to the sequence of proBNP (1-108), and where Z may represent an OH function, or 1 to 3 amino acids not belonging to the sequence of proBNP(1-108).

In addition, the authors of the present invention have shown that it is possible to obtain the same specific antibodies by immunizing an animal with a peptide of formula:

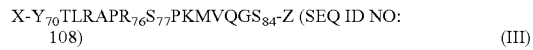
X-$Y_{70}$TLRAPR$_{76}$S$_{77}$PKMVQGS$_{84}$-Z (SEQ ID NO: 108)     (III)

where X may be H or may represent either an acetyl group, or 1 to 3 amino acids not belonging to the sequence of proBNP (1-108), and where Z may represent an OH function, or 1 to 3 amino acids not belonging to the sequence of proBNP(1-108).

The authors of the present invention have also developed a simple and reliable method for the early diagnosis of heart failure, based on the detection of circulating proBNP(1-108) in the blood, and a kit for carrying out this detection of circulating proBNP(1-108).

A subject of the present invention is therefore an anti-proBNP(1-108) antibody, characterized in that, firstly, it specifically recognizes the sequence $Y_{70}TLRAPR_{76}S_{77}PKMVQGSG_{85}$ of proBNP(1-108) and does not substantially recognize BNP(1-76) or BNP(77-108) and, secondly, it has the ability to specifically recognize circulating proBNP(1-108) in human serum or plasma samples.

A subject of the present invention is also an anti-proBNP(1-108) antibody, characterized in that, firstly, it specifically recognizes the sequence $Y_{70}TLRAPR_{76}S_{77}PKMVQGS_{84}$ of proBNP(1-108) and does not substantially recognize BNP(1-76) or BNP(77-108) and, secondly, it has the ability to specifically recognize circulating proBNP(1-108) in human serum or plasma samples.

A subject of the present invention is particularly an anti-proBNP(1-108) antibody, characterized in that, firstly, it specifically recognizes the sequence $RAPR_{76}S_{77}P$ of proBNP(1-108) and does not substantially recognize BNP(1-76) or BNP(77-108) and, secondly, it has the ability to specifically recognize circulating proBNP(1-108) in human serum or plasma samples.

A subject of the invention is also a method for obtaining anti-proBNP(1-108) antibodies that specifically recognize the sequence $Y_{70}TLRAPR_{76}S_{77}PKMVQGSG_{85}$, the sequence $Y_{70}TLRAPR_{76}S_{77}PKMVQGS_{84}$ and/or the sequence $RAPR_{76}S_{77}P$ of proBNP(1-108) with the substantial exclusion of BNP(1-76) and of BNP(77-108), and that have the ability to specifically recognize circulating proBNP(1-108) in human serum or plasma samples, characterized in that an animal is immunized with the whole proBNP(1-108) molecule, and then in that the antiserum obtained is depleted using the BNP(77-108) peptide and/or the BNP(1-76) peptide.

The expression "depletion of an antiserum" obtained against a given specific antigen (the immunizing antigen) is intended to mean the elimination of nonspecific antibodies potentially present in this antiserum by bringing said antiserum into contact with, and incubating it with, "nonspecific antigens", i.e. antigens that are different from the immunizing antigen, and then immunologically separating and eliminating the antibodies which have reacted with said "nonspecific antigens" and recovering the antiserum thus depleted (i.e. depleted of nonspecific antibodies). The depletion conventionally serves to render specific an antiserum directed against a given antigen.

In the present case, an antiserum that recognizes the sequence $Y_{70}TLRAPR_{76}S_{77}PKMVQGSG_{85}$ and/or the sequence $Y_{70}TLRAPR_{76}S_{77}PKMVQGS_{84}$ or the sequence $RAPR_{76}S_{77}P$ of proBNP(1-108) can be depleted, i.e. made specific, by bringing into contact with the abovementioned BNP(77-108) and/or BNP(1-76), it being possible, for example, for the latter to be immobilized in a solid phase and to serve as a support for chromatography by immunoadsorption according to conventional techniques, known to those skilled in the art. The antibody finally present in the depleted antiserum is here a monospecific polyclonal antibody.

A subject of the present invention is also a peptide of formula:

$a_1$-$X_1$-RAPRSP-$X_2$-$a_2$ (SEQ ID NO: 5)    (I)

where $a_1$ may be H or may represent a function or a chemical group chosen from a thiol, alcohol, aminoxy, primary amine or secondary amine function, an aminocarboxyl group, a biotinyl group and an acetyl group, $X_1$ represents a peptide sequence of 0 to 3 amino acids, which may or may not be derived from the natural sequence of proBNP(1-108), $X_2$ represents a peptide sequence of 0 to 8 amino acids, preferably 7 amino acids, which may or may not be derived from the natural sequence of proBNP(1-108), $a_2$ may represent an OH function, an $NH_2$ function or an alkoxyl group.

A subject of the present invention is also a peptide of formula: X-$Y_{70}TLRAPR_{76}S_{77}PKMVQGSG_{85}$-Z (SEQ ID NO: 4) (II) where X may be H or may represent either an acetyl group, or 1 to 3 amino acids not belonging to the sequence of proBNP(1-108), and where Z may represent an OH function, or 1 to 3 amino acids not belonging to the sequence of proBNP(1-108).

A subject of the present invention is also a peptide of formula: X-$Y_{70}TLRAPR_{76}S_{77}PKMVQGS_{84}$-Z (SEQ ID NO: 108) (III) where X may be H or may represent either an acetyl group, or 1 to 3 amino acids not belonging to the sequence of proBNP(1-108), and where Z may represent an OH function, or 1 to 3 amino acids not belonging to the sequence of proBNP(1-108).

The invention also relates to any peptide containing the sequence X-$Y_{70}TLRAPR_{76}S_{77}PKMVQGSG_{85}$-Z (SEQ ID NO: 4) (II) or the sequence X-$Y_{70}TLRAPR_{76}S_{77}PKMVQGS_{84}$-Z (SEQ ID NO: 108) (III), or one of the abovementioned sequences (II) or (III) in a form which is substituted, conservatively or nonconservatively, at any one of the amino acids of position 70 to position 85 or 84, respectively, on condition that it keeps intact (in particular unsubstituted) the portion $RAPR_{76}S_{77}P$ (SEQ ID NO: 5).

It is therefore a peptide comprising a sequence derived from the sequence X-$Y_{70}TLRAPR_{76}S_{77}PKMVQGSG_{85}$-Z (SEQ ID NO: 4) (II) or from the sequence X-$Y_{70}TLRAPR_{76}S_{77}PKMVQGS_{84}$-Z (SEQ ID NO: 108) (III) by substitution of one or more among the amino acids $Y_{70}$, $T_{71}$, $L_{72}$, $K_{79}$, $M_{80}$, $V_{81}$, $Q_{82}$, $G_{83}$, $S_{84}$ and $G_{85}$, with it being possible for X to be absent or to represent either an $NH_2$ function, or 1 to 3 amino acids not belonging to the sequence of proBNP(1-108), and it being possible for Z to be absent or to represent either an OH function, or 1 to 3 amino acids not belonging to the sequence of proBNP(1-108).

Finally, the invention relates to the peptide of sequence $Y_{70}TLRAPR_{76}S_{77}PKMVQGSG_{85}$, and to the peptide of sequence $Y_{70}TLRAPR_{76}S_{77}PKMVQGS_{84}$.

A subject of the invention is also a method for obtaining anti-proBNP(1-108) antibodies that specifically recognize the sequence $Y_{70}TLRAPR_{76}S_{77}PKMVQGSG_{85}$ (SEQ ID NO: 4), $Y_{70}TLRAPR_{76}S_{77}PKMVQGS_{84}$ (SEQ ID NO: 108) and/or the sequence $RAPR_{76}S_{77}P$ of proBNP(1-108) with the substantial exclusion of BNP(1-76) and of BNP(77-108), and that have the ability to specifically recognize circulating proBNP(1-108) in human serum or plasma samples, characterized in that an animal is immunized with a peptide of formula:

$a_1$-$X_1$-RAPRSP-$X_2$-$a_2$ (SEQ ID NO: 5)    (I)

where $a_1$, $X_1$, $X_2$ and $a_2$ have the same meaning as above, and, optionally, in that the antiserum obtained is depleted using the BNP(77-108) peptide and/or the BNP(1-76) peptide. The antibody thus obtained is a monospecific antibody.

A subject of the invention is also a method for obtaining anti-proBNP(1-108) antibodies that specifically recognize the sequence $Y_{70}TLRAPR_{76}S_{77}PKMVQGSG_{85}$ (SEQ ID NO: 4), $Y_{70}TLRAPR_{76}S_{77}PKMVQGS_{84}$ (SEQ ID NO: 108)

and/or the sequence $RAPR_{76}S_{77}P$ (SEQ ID NO: 5) of proBNP(1-108) with the substantial exclusion of BNP(1-76) and of BNP(77-108), and that have the ability to specifically recognize circulating proBNP(1-108) in human serum or plasma samples, characterized in that an animal is immunized with a peptide of formula:

$$X-Y_{70}TLRAPR_{76}S_{77}PKMVQGSG_{85}-Z \text{ (SEQ ID NO: 4)} \quad (II)$$

or with a peptide of formula $X-Y_{70}TLRAPR_{76}S_{77}PKMVQGS_{84}-Z$ (SEQ ID NO: 108) (III), where X and Z are as defined above and, optionally, in that the antiserum obtained is depleted using the BNP(77-108) peptide and/or the BNP(1-76) peptide.

A subject of the invention is also a method for obtaining a hybridoma that secretes anti-proBNP(1-108) antibodies that specifically recognize the sequence $Y_{70}TLRAPR_{76}S_{77}PKMVQGSG_{85}$ (SEQ ID NO: 4), $Y_{70}TLRAPR_{76}S_{77}PKMVQGS_{84}$ (SEQ ID NO: 108) and/or the sequence $RAPR_{76}S_{77}P$ of proBNP(1-108) with the substantial exclusion of BNP(1-76) and of BNP(77-108), and that have the ability to specifically recognize circulating proBNP(1-108) in human serum or plasma samples, characterized in that an animal is immunized with a peptide of formula:

$$X-Y_{70}TLRAPR_{76}S_{77}PKMVQGSG_{85}-Z \text{ (SEQ ID NO: 4)} \quad (II)$$

or with a peptide of formula $X-Y_{70}TLRAPR_{76}S_{77}PKMVQGS_{84}-Z$ (SEQ ID NO: 108) (III), in a form that is substituted, conservatively or nonconservatively, on condition that it keeps intact (in particular unsubstituted) the portion $RAPR_{76}S_{77}P$ (SEQ ID NO: 5), where X and Z are as defined above and, optionally, in that the antiserum obtained is depleted using the BNP(77-108) peptide and/or the BNP(1-76) peptide.

A subject of the invention is also a method for obtaining anti-proBNP(1-108) antibodies that specifically recognize the sequence $Y_{70}TLRAPR_{76}S_{77}PKMVQGSG_{85}$, $Y_{70}TLRAPR_{76}S_{77}PKMVQGS_{84}$ and/or the sequence $RAPR_{76}S_{77}P$ of proBNP(1-108) with the substantial exclusion of the BNP(1-76) and BNP(77-108) peptides, and that have the ability to specifically recognize circulating proBNP (1-108) in human serum or plasma samples, characterized in that an animal is immunized with the peptide of sequence $Y_{70}TLRAPR_{76}S_{77}PKMVQGSG_{85}$ or the peptide of sequence $Y_{70}TLRAPR_{76}S_{77}PKMVQGS_{84}$ and, optionally, in that the antiserum obtained is depleted using the BNP(77-108) peptide and/or the BNP(1-76) peptide.

A subject of the invention is also a method for obtaining a hybridoma that secretes anti-proBNP(1-108) antibodies that specifically recognize the sequence $Y_{70}TLRAPR_{76}S_{77}PKMVQGSG_{85}$, the sequence $Y_{70}TLRAPR_{76}S_{77}PKMVQGS_{84}$ and/or the sequence $RAPR_{76}S_{77}P$ of proBNP(1-108) with the substantial exclusion of BNP(1-76) and of BNP(77-108), and that have the ability to specifically recognize circulating proBNP(1-108) in human serum or plasma samples, characterized in that:

an animal is immunized with a peptide chosen from the peptides of formulae below:

$$a_1-X_1-RAPRSP-X_2-a_2 \text{ (SEQ ID NO: 5)} \quad (I)$$

where $a_1$, $X_1$, $X_2$ and $a_2$ have the same meaning as above, $$X-Y_{70}TLRAPR_{76}S_{77}PKMVQGSG_{85}-Z \text{ (SEQ ID NO: 4)} \quad (II)$$

where X and Z have the same meaning as above, $$X-Y_{70}TLRAPR_{76}S_{77}PKMVQGS_{84}-Z \text{ (SEQ ID NO: 108)} \quad (III)$$

where X and Z have the same meaning as above, $$X-Y_{70}TLRAPR_{76}S_{77}PKMVQGSG_{85}-Z \text{ (SEQ ID NO: 4)} \quad (II)$$

in a form which is substituted, conservatively or nonconservatively, on condition that it keeps intact (in particular unsubstituted) the portion $RAPR_{76}S_{77}P$, where X and Z have the same meaning as above, $$X-Y_{70}TLRAPR_{76}S_{77}PKMVQGS_{84}-Z \text{ (SEQ ID NO: 108)} \quad (III)$$

in a form which is substituted, conservatively or nonconservatively, on condition that it keeps intact (in particular unsubstituted) the portion $RAPR_{76}S_{77}P$ (SEQ ID NO: 5), where X and Z have the same meaning as above, $Y_{70}TLRAPR_{76}S_{77}PKMVQGSG_{85}$ (SEQ ID NO: 4) and $Y_{70}TLRAPR_{76}S_{77}PKMVQGS_{84}$ (SEQ ID NO: 108);

immunoglobulin-secreting lymphocytes are removed from this animal, and in that the lymphocytes are fused with myeloma cells so as to obtain at least one immunoglobulin-secreting hybridoma.

This corresponds to the conventional technique for obtaining hybridomas, the principle of which is described in Köhler and Milstein, (1975) Nature (London), 256: 495-497.

A subject of the invention is also such a hybridoma and the monoclonal anti-proBNP(1-108) antibody secreted by said hybridoma.

A subject of the present invention is also a method of in vitro diagnosis of heart failure in a human, comprising bringing a biological sample, preferably blood, plasma or serum, into contact with an anti-proBNP(1-108) antibody that specifically recognizes the sequence $Y_{70}TLRAPR_{76}S_{77}PKMVQGSG_{85}$, the sequence $Y_{70}TLRAPR_{76}S_{77}PKMVQGS_{84}$ and/or the sequence $RAPR_{76}S_{77}P$ of proBNP(1-108) with the substantial exclusion of BNP(1-76) and of BNP(77-108), and that has the ability to specifically recognize circulating proBNP(1-108) in human serum or plasma samples, and detecting the proBNP (1-108) in the sample.

The invention provides, in general, a method of in vitro diagnosis of heart failure in a human, comprising:

a) bringing a biological sample, preferably blood, plasma or serum, into contact with an anti-proBNP(1-108) antibody that specifically recognizes the sequence $Y_{70}TLRAPR_{76}S_{77}PKMVQGSG_{85}$, the sequence $Y_{70}TLRAPR_{76}S_{77}PKMVQGS_{84}$ and/or the sequence $RAPR_{76}S_{77}P$ of proBNP(1-108) with the substantial exclusion of BNP(1-76) and of BNP(77-108), and that has the ability to specifically recognize circulating proBNP(1-108) in human serum or plasma samples, b) incubating the mixture under conditions that allow the formation of antigen-antibody complexes, and c) revealing the antigen-antibody complexes formed, optionally using a labeled detection antibody capable of binding specifically to the proBNP(1-108) present in the primary complex, or using a labeled detection antigen capable of binding to the antibody directed against said proBNP(1-108) present in the primary complex.

In particular, the invention provides a method of diagnosing heart failure which comprises, in addition to the above-mentioned steps a, b and c, a step d) for correlating the amount of the antigen-antibody complexes revealed with the clinical condition of the individual.

A subject of the present invention is also a kit for detecting proBNP(1-108) in a biological sample, in particular in a blood, plasma or serum sample, containing at least one anti-proBNP(1-108) antibody that specifically recognizes the sequence $Y_{70}TLRAPR_{76}S_{77}PKMVQGSG_{85}$, the sequence $Y_{70}TLRAPR_{76}S_{77}PKMVQGS_{84}$ and/or the sequence $RAPR_{76}S_{77}P$ of proBNP(1-108) with the substantial exclusion of BNP(1-76) and of BNP(77-108), and that has the ability to specifically recognize circulating proBNP(1-108) in human serum or plasma samples.

Finally, the invention is directed toward a kit for detecting proBNP(1-108) in a biological sample, in particular in a blood, plasma or serum sample, containing, as standard and/or control, a compound containing at least one peptide chosen from the group of peptides of formulae below:

$a_1$-$X_1$-RAPRSP-$X_2$-$a_2$ (SEQ ID NO: 5)   (I)

where $a_1$, $X_1$, $X_2$ and $a_2$ have the same meaning as above,

X-$Y_{70}TLRAPR_{76}S_{77}PKMVQGSG_{85}$-Z (SEQ ID NO: 4)   (II)

where X and Z have the same meaning as above,

X-$Y_{70}TLRAPR_{76}S_{77}PKMVQGSG_{85}$-Z (SEQ ID NO: 4)   (II)

in a form which is substituted, conservatively or nonconservatively, on condition that it keeps intact (in particular unsubstituted) the portion $RAPR_{76}S_{77}P$ (SEQ ID NO: 5), where X and Z have the same meaning as above,

X-$Y_{70}TLRAPR_{76}S_{77}PKMVQGS_{84}$-Z (SEQ ID NO: 108)   (III)

where X and Z have the same meaning as above

X-$Y_{70}TLRAPR_{76}S_{77}PKMVQGS_{84}$-Z (SEQ ID NO: 108)   (III)

in a form which is substituted, conservatively or nonconservatively, on condition that it keeps intact (in particular unsubstituted) the portion $RAPR_{76}S_{77}P$ (SEQ ID NO: 5), where X and Z have the same meaning as above, $Y_{70}TLRAPR_{76}S_{77}PKMVQGSG_{85}$ (SEQ ID NO: 4), $Y_{70}TLRAPR_{76}S_{77}PKMVQGS_{84}$ (SEQ ID NO: 108).

Definitions

In the context of the invention, a "biological sample" or alternatively a "biological fluid sample" preferably consists of a biological liquid, such as blood, plasma, serum, urine, cerebrospinal fluid, saliva, etc.

The term "heart failure" is intended to mean the pathological condition in which an anomaly of cardiac function is responsible for the inability of the heart to pump blood sufficiently to satisfy the metabolic needs of the organism and/or in which the heart meets the needs but with abnormally high filling pressures. It may in particular be a right and/or left ventricular failure.

The term "antibody" refers to any whole antibody or functional fragment of an antibody (which may or may not be obtained by genetic engineering) comprising, or consisting of, at least one antigen combining site, allowing said antibody to bind to at least one antigenic determinant of an antigenic compound. By way of example of antibody fragments, mention may be made of Fab, Fab' and F(ab')$_2$ fragments and also single-chain variable fragments (scFv chains).

The anti-proBNP(1-108) antibodies according to the invention may be of the polyclonal or monoclonal type. A polyclonal anti-proBNP(1-108) antibody according to the invention may be obtained, inter alia, by immunizing an animal such as a rabbit, a mouse, etc., using whole proBNP(1-108), removing the antiserum obtained and then depleting it on, for example, an immunoadsorbent containing BNP(77-108) and/or BNP(1-76) according to methods known in themselves to those skilled in the art. A monoclonal anti-proBNP (1-108) antibody according to the invention may be obtained, inter alia, by the conventional method of Köhler and Milstein (Nature (London), 256: 495-497 (1975)).

The production of monoclonal antibodies or of monospecific polyclonal sera, or of antibodies obtained by screening genomic libraries, that are useful in the context of the invention, results from conventional techniques which are explained in detail later.

The term "capture antibody" is intended to mean an antibody or a part of an antibody, preferably attached to a solid phase, which is capable of retaining the proBNP(1-108) antigen present in a biological sample, by affinity binding.

The presence of the antigen in the biological sample is revealed by "detection means". As regards the detection of the antigen, the invention envisions in particular detection using at least one "detection antibody". Such a detection antibody, that is labeled, is capable of binding to the antigen captured, by affinity binding, by recognizing an epitope site that is different from that recognized by the capture antibody.

The term "labeled" refers both to direct labeling (by means of enzymes, radioisotopes, fluorochromes, luminescent compounds, etc.) and to indirect labeling (for example by means of antibodies that are themselves directly labeled or using reagents of a labeled "affinity pair", such as, but not exclusively, the labeled avidin-biotin pair, etc.).

The term "antigenic fragment" is intended to mean any part of proBNP(1-108) capable of inducing the synthesis of antibodies substantially specific for only proBNP(1-108) in an immunized animal.

In accordance with the present invention, an "antigenic fragment" contains at least the "epitope site" or epitope $RAPR_{76}S_{77}P$. An "epitope site" or "epitope" is a sequence of amino acids which is recognized by at least one antibody and allows the specific binding thereof.

The term "monospecific polyclonal antibody" applies to any polyclonal antibody having specificity for a single epitope. This means that the antibody is capable of binding an amino acid sequence of the sequence of proBNP(1-108) containing the amino acids comprising the epitope, but is incapable of binding an amino acid sequence of the sequence proBNP(1-108) which does not contain the amino acids comprising the epitope.

The term "specifically", when it refers to a recognition or a specific binding of an antibody for an antigen, means that the antibody interacts with the antigen without substantial interaction with other antigens, or if referring to "specific" recognition with an epitope, by virtually exclusive recognition of this epitope. Association constants greater than $10^8$ L·mol$^{-1}$ are preferable.

The term "conservative substitution" is intended to mean in particular the substitution of an amino acid of one class with an amino acid of the same class, which substitution does not significantly modify the immunoreactivity of the peptide obtained relative to that of the peptide of origin. Among the various amino acid classes, amino acids with a polar side chain (such as asparagine, glutamine, serine, threonine and tyrosine), amino acids with a nonpolar side chain (such as glycine, alanine, valine, leucine, isoleucine, phenylalanine, methionine, tryptophan and cysteine), amino acids with a basic side chain (such as lysine, arginine and histidine), and amino acids with an acid side chain (such as aspartic acid and glutamic acid), are generally distinguished.

The term "nonconservative substitution" is intended to mean any other type of substitution, which does not significantly modify the immunoreactivity of the peptide obtained relative to that of the peptide of origin.

The expression “does not substantially recognize BNP(1-76) or BNP(77-108)” is intended to mean that the antibody targeted by the invention exhibits a cross reaction with BNP (1-76) or BNP(77-108) of less than 20%, particularly of less than 10%, preferably of less than 5%. The percentage cross reaction is determined according to methods known in themselves to those skilled in the art, for example that illustrated in example 5.

The “substantial” nonrecognition of the BNP(1-76) and BNP(77-108) peptides preferably corresponds to an absence, or virtual absence, of reaction of the antibodies of the invention with these peptides.

The expression “with the substantial exclusion of BNP(1-76) and of BNP(77-108)” is intended to mean that the antibody “does not substantially recognize BNP(1-76) or BNP (77-108)” in the sense seen above.

Production of Specific Antibodies

The antibodies used in the present invention are antigen-specific antibodies and, for this reason, are monoclonal antibodies or monospecific polyclonal antibodies, i.e. they specifically recognize only one epitope.

The monoclonal antibodies can be obtained according to the conventional method of lymphocyte fusion and hybridoma culture described by Köhler and Milstein, Nature, 1975, 256: 495-497. Other methods for preparing monoclonal antibodies are also known (Harlow et al, ed., 1988 “Antibodies: a laboratory manual”). The monoclonal antibodies can be prepared by immunizing a mammal (for example a mouse, a rat, a rabbit, or even a human being, etc.) and using the lymphocyte fusion technique resulting in hybridomas (Köhler and Milstein, 1975).

Techniques that are alternatives to this usual technique exist. It is possible, for example, to produce monoclonal antibodies by expressing a nucleic acid cloned from a hybridoma. It is also possible to produce antibodies by the phage display technique, by introducing antibody cDNAs into vectors, which are typically filamentous phages which present V gene libraries at the surface of the phage (for example fUSE5 for *E. coli*, J. K. Scott and G. P. Smith, *Science,* 1990, 249: 386-390). Protocols for constructing these antibody libraries are described in Marks et al., 1991, J. Mol. Biol, 222: 581-597).

The polyclonal antibodies can be obtained from a serum of an animal immunized against an antigen that is peptide in nature, according to the usual procedures. The polyclonal antibodies thus obtained may, if need be, and by depletion with BNP(77-108) and BNP(1-76), according to techniques known in themselves to those skilled in the art, such as, for example, column immunoadsorption, be made monospecific for the sequence $Y_{70}TLRAPR_{76}S_{77}PKMVQGSG_{85}$, for the sequence $Y_{70}TLRAPR_{76}S_{77}PKMVQGS_{84}$ and/or for a peptide comprising the sequence $RAPR_{76}S_{77}P$, thus ensuring specificity with respect to proBNP(1-108), with the substantial exclusion of BNP(1-76) and of BNP(77-108).

Capture and/or Detection Antibodies

In the sandwich technique, the capture antibody is chosen such that it specifically recognizes an epitope, on the natural antigen of the patient, while the detection antibody is chosen, preferably but not necessarily, such that it specifically recognizes another epitope, on the natural antigen of the patient.

The biological sample can optionally be treated in a prior step, or placed directly together with at least one capture antibody under conditions that promote exposure of the epitope to be detected.

The diagnostic method according to the invention can be carried out according to various formats well known to those skilled in the art: in a solid phase or in a homogeneous phase; in one step or in two steps; in the sandwich method or in a competition method, by way of nonlimiting examples.

According to a preferred embodiment, the capture antibody is immobilized on a solid phase. By way of nonlimiting examples of the solid phase, use may be made of microplates, in particular of polystyrene microplates such as those sold by the company Nunc, Denmark. Use may also be made of solid particles or beads, paramagnetic beads, such as those provided by Dynal or Merck-Eurolab (France) (under the trademark Estapor™), or else polystyrene or propylene test tubes, etc.

An immunoassay format such as a sandwich between two antibodies (capture and detection antibodies) is particularly advantageous for detecting the antigens present in the biological sample.

An immunoassay format for detecting the antigens by competition is also possible. Other immunoassay modes can also be envisioned and are well known to those skilled in the art.

ELISA assays, radioimmunoassays, or any other detection technique can be used to reveal the presence of the antigen-antibody complexes formed.

Kits

The kits and reagents used for detecting the proBNP(1-108) in a biological fluid sample, in accordance with the method of the invention, can be provided for a practical implementation of the invention that is easy and applicable to many biological samples.

Kits for detecting proBNP(1-108) in a biological sample can contain at least one antibody as defined above. Other kits, containing, as standard and/or control, at least one peptide of formula (I) or (II) or a substituted peptide as defined above, may also be useful for implementing the invention.

Another particular subject of the invention is therefore a kit for detecting proBNP(1-108) in a biological fluid sample, comprising:

- at least one anti-proBNP(1-108) antibody that specifically recognizes the sequence $Y_{70}TLRAPR_{76}S_{77}PKMVQGSG_{85}$, the sequence $Y_{70}TLRAPR_{76}S_{77}PKMVQGS_{84}$ and/or the sequence $RAPR_{76}S_{77}P$ of proBNP(1-108) with the substantial exclusion of BNP(1-76) and of BNP(77-108), and that has the ability to specifically recognize circulating proBNP(1-108) in human serum or plasma samples, and that is preferably an antibody for capturing said proBNP (1-108) present in said biological sample, and a labeled conjugate capable of binding specifically to the antigen-antibody complexes formed.

As is described above, the capture antibody may be advantageously provided in a form immobilized on a solid phase, such as a microplate, for example, but not exclusively.

A preferred kit comprises at least:

an anti-proBNP(1-108) capture antibody that specifically recognizes the sequence $Y_{70}TLRAPR_{76}S_{77}PKMVQGS_{85}$, the sequence $Y_{70}TLRAPR_{76}S_{77}PKMVQGS_{84}$, and/or the sequence $RAPR_{76}S_{77}P$ of proBNP(1-108) with the substantial exclusion of BNP(1-76) and of BNP(77-108), and that has the ability to specifically recognize circulating proBNP(1-108) in human serum or plasma samples, said capture antibody being immobilized on a solid phase; and a labeled detection antibody directed against another epitope, that is intact, of proBNP(1-108), or optionally a labeled detection antigen which is a peptide of proBNP(1-108) or proBNP(1-108) itself.

According to a particular embodiment, a kit for detecting proBNP(1-108) in a biological sample, may contain:

in a container, at least one antibody as defined above;

in another container, at least one peptide as defined above, that is useful in particular as a standard and/or control.

The following figures and examples illustrate the invention without limiting the scope thereof.

FIGURE LEGENDS

Figure 9:
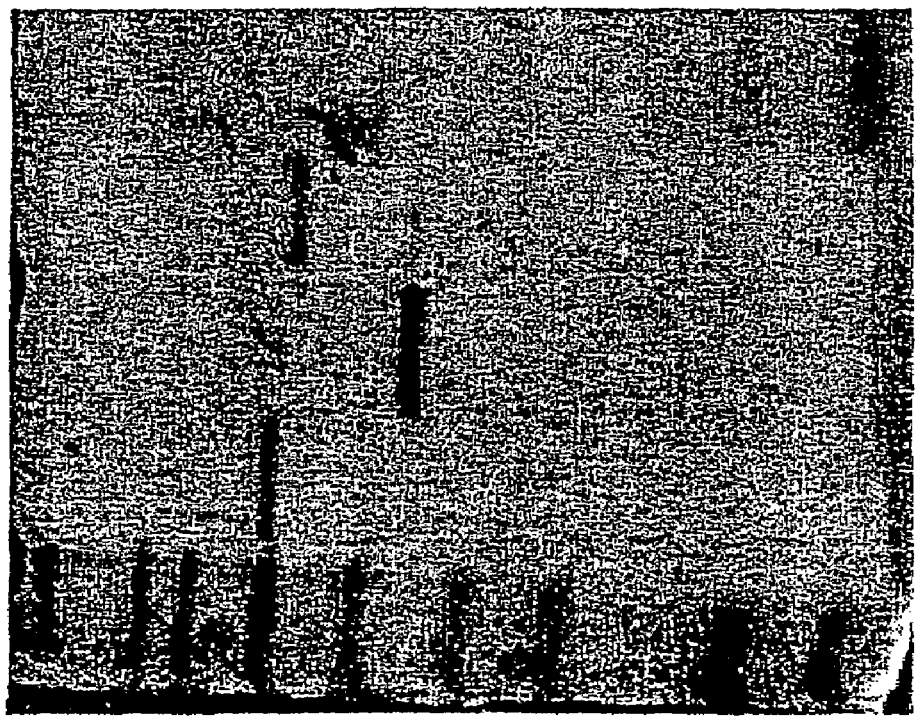

FIG. 9 shows a photograph of the 16% acrylamide gel in which each protein was migrated (1 µg of protein per lane). Lane 1: molecular weight marker; lane 2: proBNP(1-108)-GST; lane 3: GST (negative control protein); lane 4: BNP(1-76)-GST; lane 5: BNP(77-108).

Figure 10:
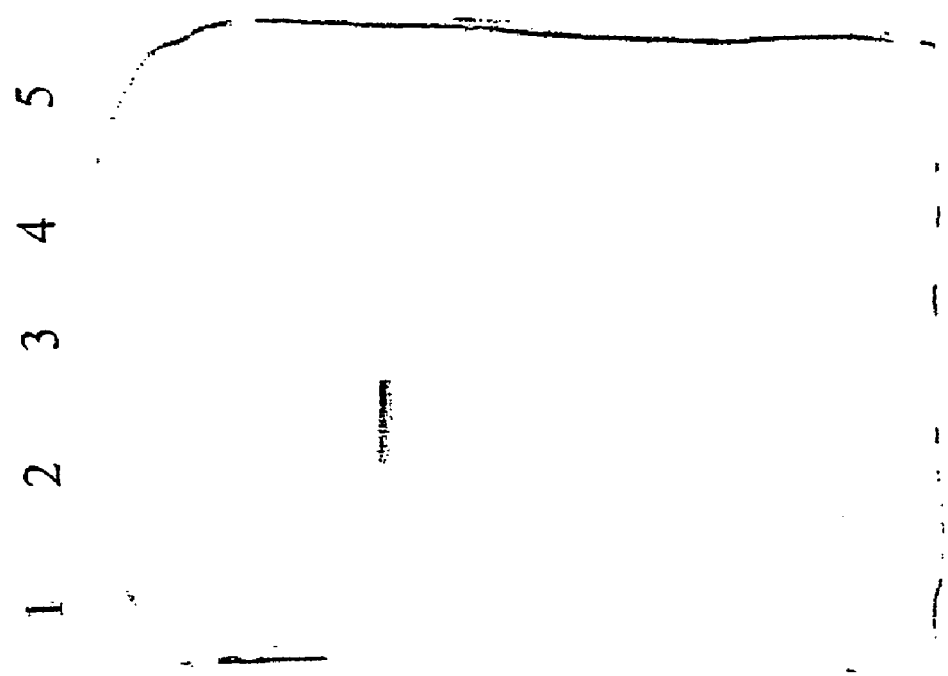

FIG. 10 shows the results of the Western blotting assay with the antibody produced by the 3D4 hybridoma, on proBNP(1-108)-GST (lane 2), GST (negative control protein) (lane 3), BNP(1-76)-GST (lane 4), and BNP(77-108) (lane 5), loaded on a gel (1 µg of protein per gel) and then transferred onto a nitrocellulose membrane.

Figure 11:
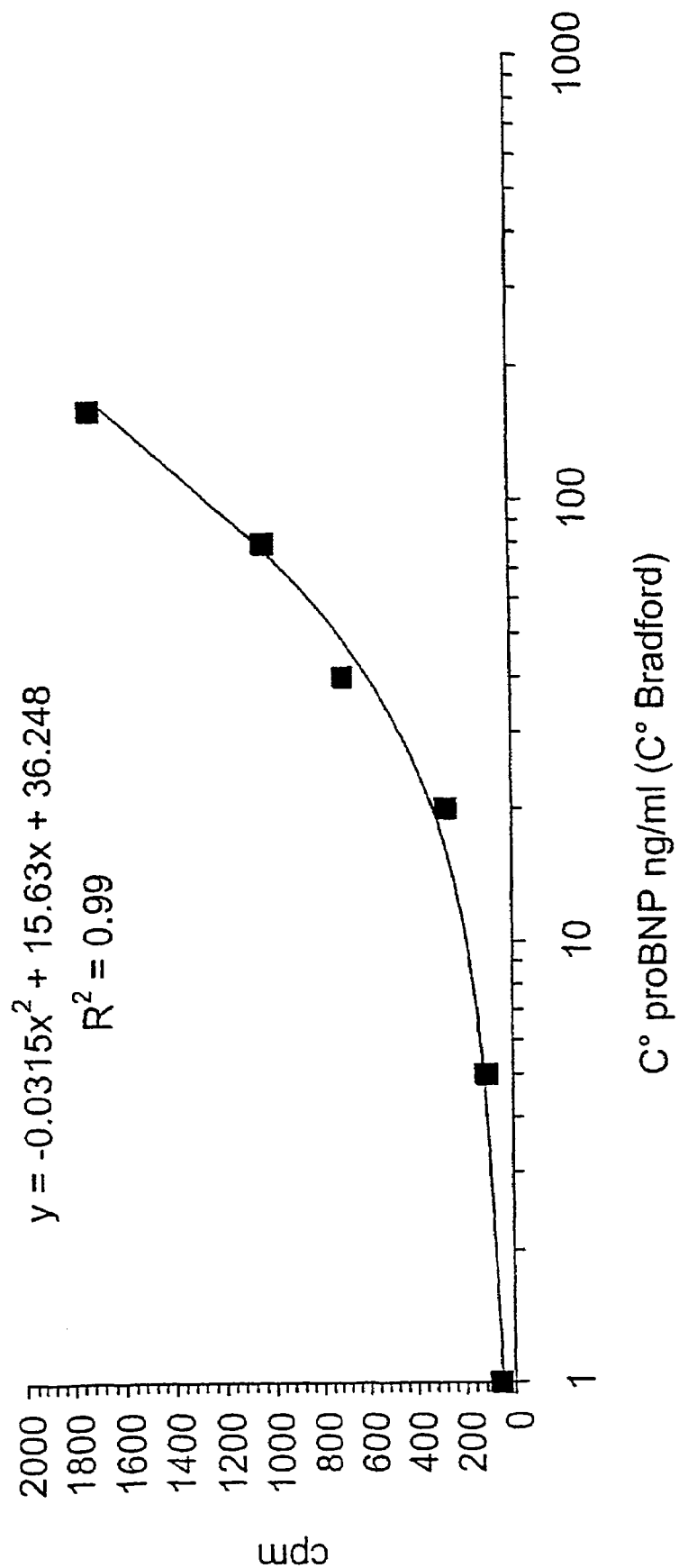

FIG. 11 represents a standard curve for the proBNP(1-108) IRMA assay.

Figure 12:
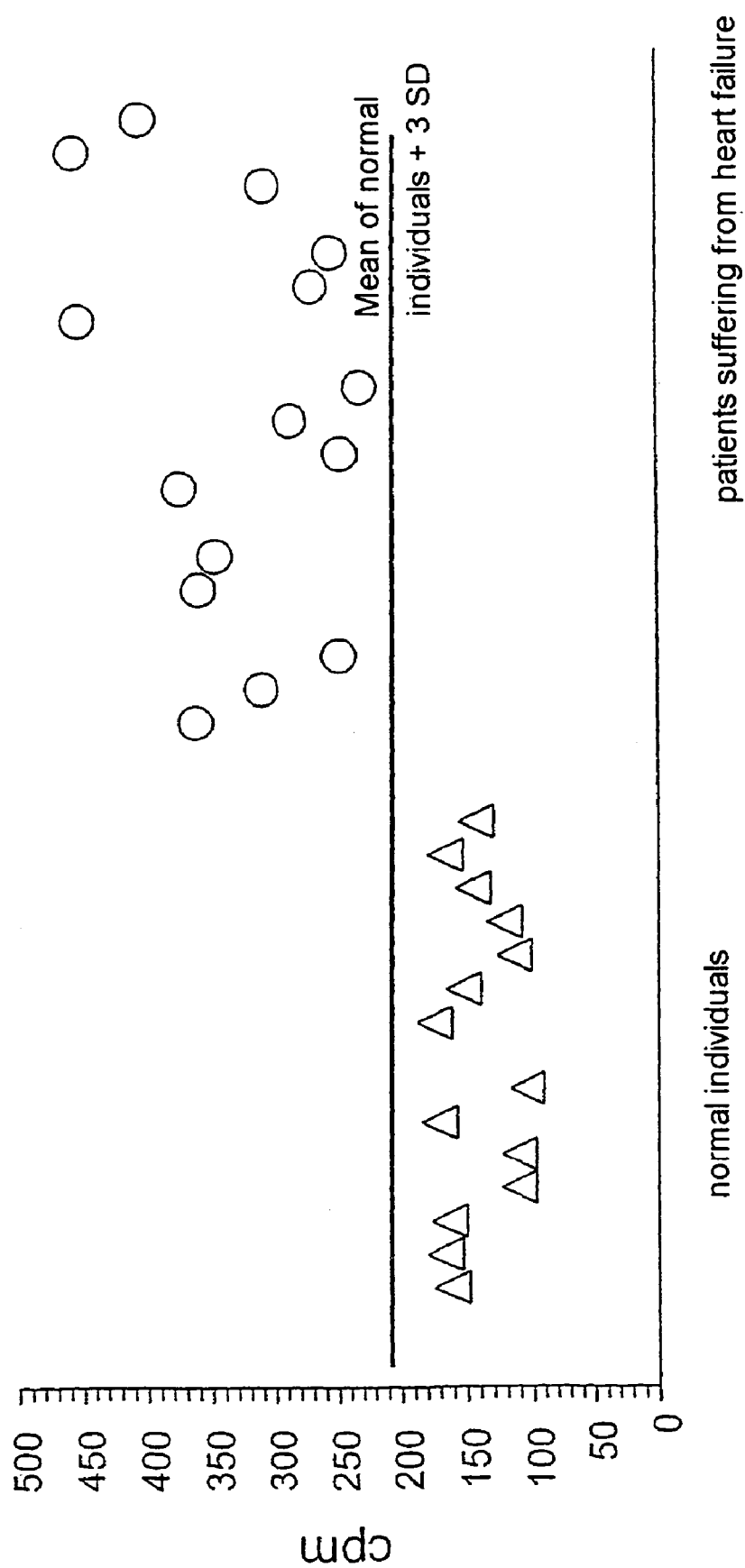

FIG. 12 shows the results in cpm (counts per minute of radioactivity) of the IRMA assay for proBNP(1-108) in the samples from 14 normal individuals and from 15 patients suffering from heart failure.

Figure 13:
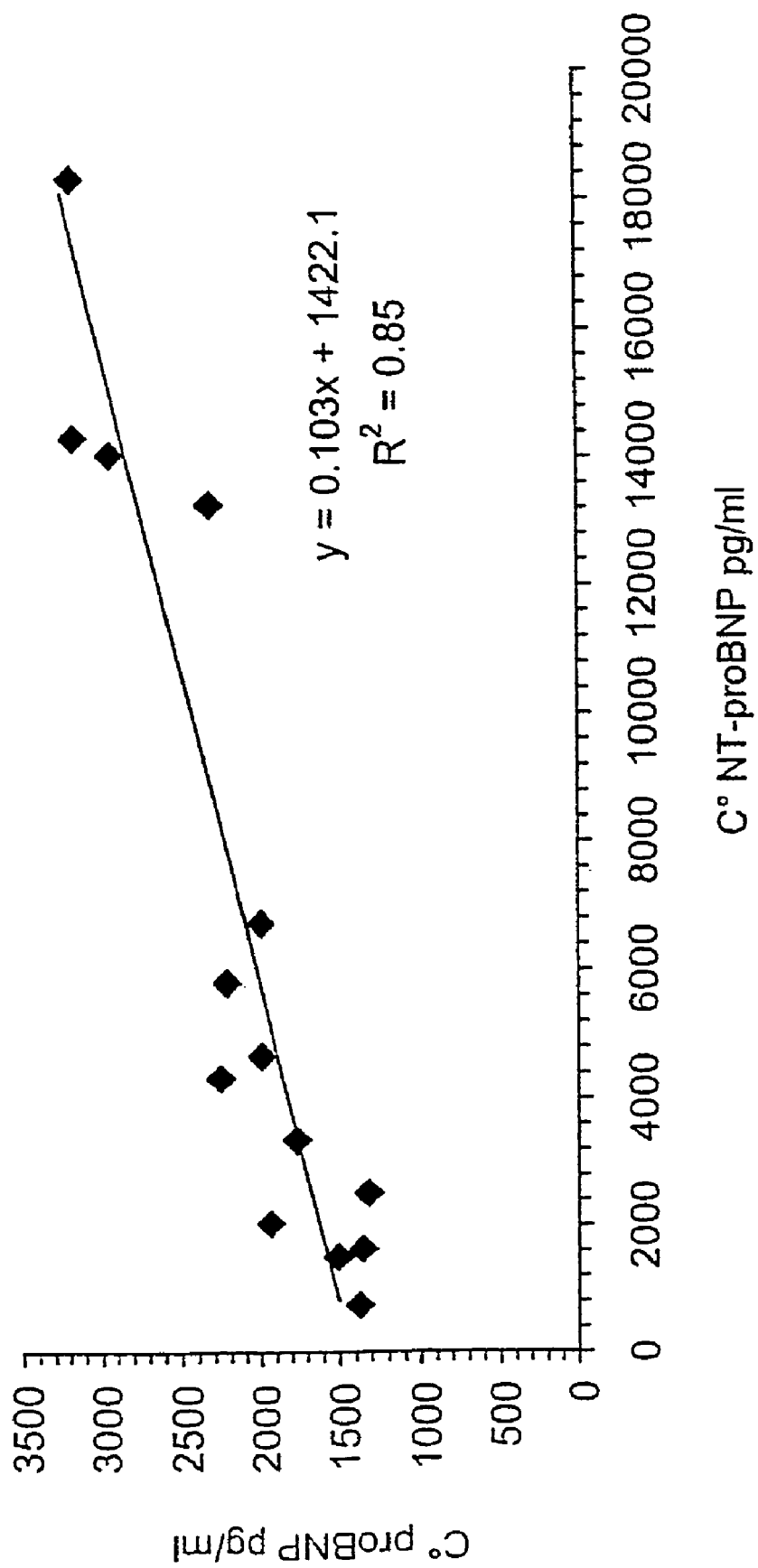

FIG. 13 gives the correlation between the concentrations of proBNP(1-108) (in pg/ml) determined by means of the immunoradiometric assay according to the invention and the concentrations of BNP(1-76) (pg/ml) determined by means of the assay on the Elecsys® automated device (trademark of the company Hoffmann La Roche), in the samples from 14 patients suffering from heart failure.

Figure 14:
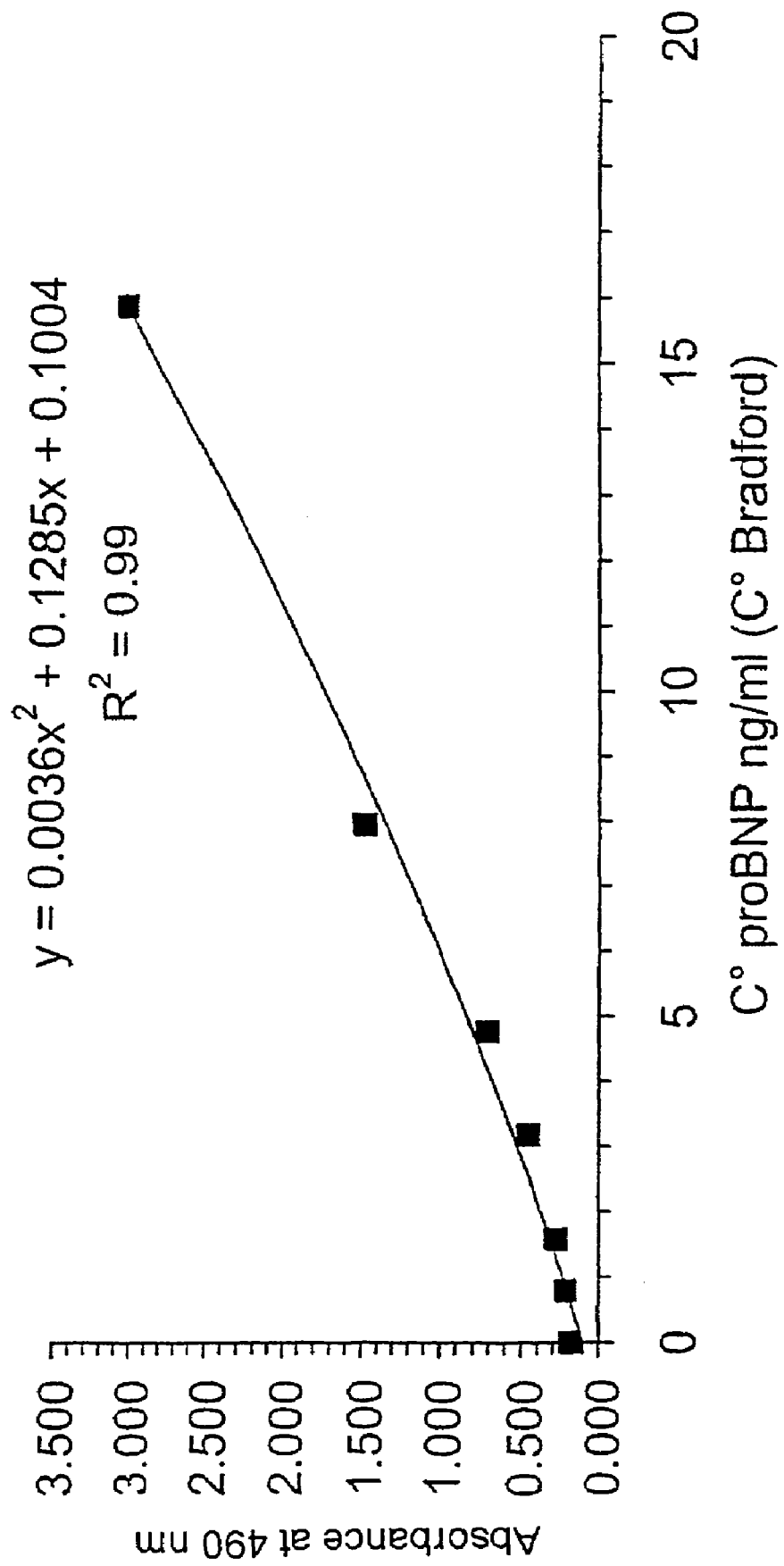

FIG. 14 represents a standard curve of the ELISA assay for proBNP(1-108) according to the invention.

Figure 15:
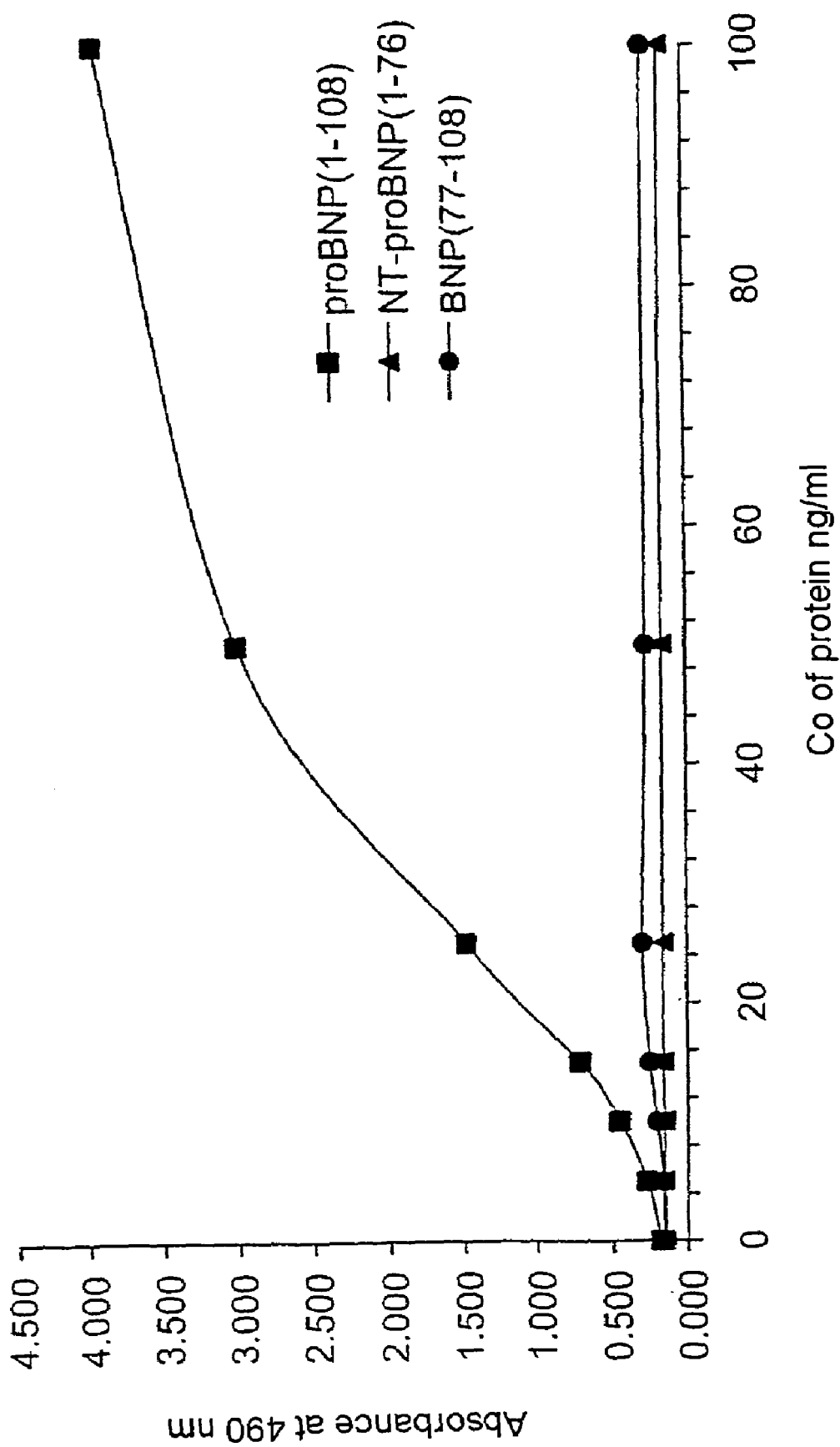

FIG. 15 represents an evaluation of the cross reaction, with respect to BNP(1-76) and to BNP(77-108), of the polyclonal antibody of rabbit #046 805, not depleted, coupled to biotin, used in a sandwich in the proBNP(1-108) ELISA assay, jointly with the anti-BNP(77-108) polyclonal antibody.

Figure 16:
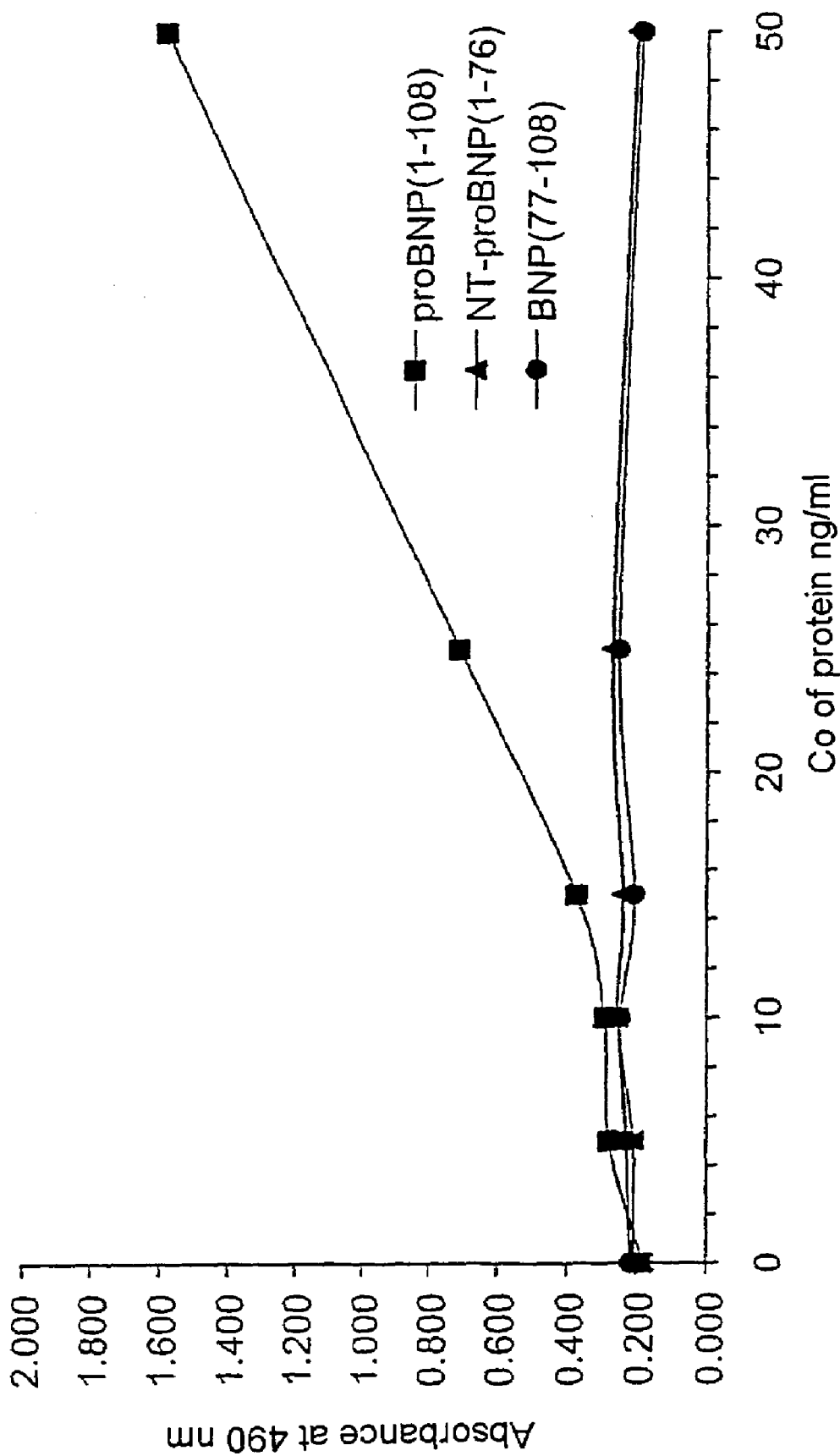

FIG. 16 represents the evaluation of the cross reaction, with respect to BNP(1-76) and to BNP(77-108), of the polyclonal antibody from rabbit #046 805, not depleted, coupled to biotin, used in a sandwich in the proBNP(1-108) ELISA assay, together with the anti-NT-proBNP(1-29) polyclonal antibody.

EXAMPLES

Example 1

Synthesis of Peptides for Immunization

The synthetic peptides are produced by standard techniques well known to those skilled in the art. Mention may be made, by way of example, of Merrifield-type synthesis, which is advantageous given the ease with which it can be carried out (Merrifield, (1963); R. C. Sheppard (1971); Atherton et al. (1989)). As an automatic synthesizer, use may be made of the Millipore "9050 Plus Pep Synthesizer", the Perspective "Pioneer" synthesizer or the ABI "433A" synthesizer. The peptides can also be obtained by homogeneous-phase synthesis.

The syntheses hereinafter were carried out on a Pioneer synthesizer, using "Fmoc" (9-fluorenylmethyloxy-carbonyl) chemistry: at each step, the reagents (i.e. the protected amino acid and the coupling activators (TBTU(2-(1H-benzotriazol-1-yl)-1,1,3,3-tetramethyl-uronium tetrafluoroborate)/HOBt (N-hydroxybenzo-triazole)) are added in excess (in a ratio "moles of reagent/moles of substitutable groups on the resin"=5). At the end of the synthesis, the peptide is separated from the resin with a trifluoroacetic acid-based solution (reagent K). The peptide is then precipitated in a cooled ether solution, and then purified by HPLC.

The inventors synthesized the following peptides containing the amino acid sequence of the hinge region $R_{76}S_{77}$:

```
SEQ ID No. 6:     C-G-R-A-P-R-S-P

SEQ ID No. 7:     Acetyl-C-G-R-A-P-R-S-P

SEQ ID No. 8:     C-G-R-A-P-R-S-P-K

SEQ ID No. 9:     Acetyl-C-G-R-A-P-R-S-P-K

SEQ ID No. 10:    C-G-R-A-P-R-S-P-K-M-V

SEQ ID No. 11:    C-G-R-A-P-R-S-P-K-M-V-Q-G-S-G

SEQ ID No. 12:    R-A-P-R-S-P-G-C

SEQ ID No. 13:    Acetyl-R-A-P-R-S-P-G-C

SEQ ID No. 14:    Acetyl-C-Y-T-L-R-A-P-R-S-P-K

SEQ ID No. 15:    C-H-R-K-M-V-L-Y-T-L-R-A-P-R-S-P-K

SEQ ID No. 16:    C-Y-T-L-R-A-P-R-S-P-K-M-V-Q-G-S-G
                  (peptide C13P30)

SEQ ID No. 17:    C-F-T-L-R-A-P-R-S-P-K-M-V-Q-G-S-G

SEQ ID No. 18:    C-F-S-I-R-A-P-R-S-P-K-M-V-Q-G-S-G

SEQ ID No. 19:    C-Y-T-L-R-A-P-R-S-P-K-M-V-Q-G-S-βA

SEQ ID No. 20:    C-Y-T-L-R-A-P-R-S-P-K-M-V-Q-A-T-βA

SEQ ID No. 21:    C-F-S-I-R-A-P-R-S-P-K-M-V-Q-A-T-βA

SEQ ID No. 22:    C-F-S-I-R-A-P-R-S-P-A-L-A-S-G-T-A
and also

SEQ ID No. 109:   C-Y-T-L-R-A-P-R-S-P-K-M-V-Q-G-S
                  (peptide CN32)

SEQ ID No. 110:   C-Y-T-L-R-A-P-R-S-P-K

SEQ ID No. 111:   C-Y-T-L-R-A-P-R-S-P-K-M-V

SEQ ID No. 112:   C-Y-T-L-R-A-P-R-S-P-K-M-V-Q

SEQ ID No. 113:   C-Y-T-L-R-A-P-R-S-P-K-M-V-Q-G

SEQ ID No. 114:   Acetyl-C-T-L-R-A-P-R-S-P-K-M-V-Q

SEQ ID No. 115:   C-T-L-R-A-P-R-S-P-K-M-V-Q-G

SEQ ID No. 116:   C-T-L-R-A-P-R-S-P-K-M-V-Q-G-S

SEQ ID No. 117:   C-T-L-R-A-P-R-S-P-K-M-V-Q-G-S-G

SEQ ID No. 118:   C-L-R-A-P-R-S-P-K-M-V

SEQ ID No. 119:   C-L-R-A-P-R-S-P-K-M-V-Q

SEQ ID No. 120:   L-R-A-P-R-S-P-K-M-V-Q-C

SEQ ID No. 121:   C-L-R-A-P-R-S-P-K-M-V-Q-G-S

SEQ ID No. 122:   C-L-R-A-P-R-S-P-K-M-V-Q-G-S-G
NB: βA signifies beta-alanine.
```

The subject of the invention is therefore also any peptide chosen from the group consisting of the above sequences.

Example 2

Coupling of a Peptide to a Carrier Protein for Immunization

The peptide is coupled to a carrier protein, KLH (Keyhole Limpet Hemocyanin), thyroglobulin, BSA (bovine serum albumin), via various functions (thiol, amine, aldehyde, etc.), so as to make the peptide more immunogenic. The coupling agent used to bond the peptide to the protein may be heterobifunctional or homobifunctional. The reagents most commonly used are BS3, sSMCC, SPDP, glutaraldehyde, etc. One of the coupling techniques used is that which uses glutaraldehyde as chemical coupling agent and KLH as carrier protein. The coupling of the KLH to the peptide is carried out using the amine functions of the peptide (N-terminal group and amine group carried by lysine mainly).

A solution of the peptide C13P30 of sequence YTLRAPRSPKMVQGSG-NH$_2$ (SEQ ID No. 16) or of the peptide CN32 of sequence YTLRAPRSPKMVQGS-NH$_2$ (SEQ ID No. 109) at 5 mg/ml is prepared in Dulbecco PBS buffer containing 0.15M NaCl, at pH 7.4. A bottle of 20 mg of KLH lyophilized in PBS buffer (Pierce #77600) is taken up with 2 ml of water for injectable preparation, so as to obtain a 10 mg/ml KLH solution in PBS buffer.

1 ml of the peptide solution (i.e. 5 mg) is mixed with 1.25 ml of the KLH solution (i.e. 12.5 mg). Under a suction hood, 2.25 ml of a 2% glutaraldehyde solution, prepared extemporaneously (from 25% glutaraldehyde, Sigma #G-5882), are added to the mixture. In order to avoid the formation of KLH complexes, the 2% glutaraldehyde solution is added dropwise and with stirring of the mixture. The conjugation reaction is carried out for 2 hours 30 min of incubation at ambient temperature. The coupling reaction is stopped by adding a 100 mg/ml sodium borohydride solution so as to achieve a final concentration of 10 mg/ml. The mixture is incubated overnight at 4° C. Finally, the solution is dialyzed overnight at 4° C. against Dulbecco PBS buffer at pH 7.4. The solution is finally aliquoted and stored at −80° C.

Example 3

Immunizations with Peptides

For the production of polyclonal antibodies, rabbits (females of the New Zealand strain) were immunized with the peptide Cys-YTLRAPRSPKMVQGSG-NH$_2$ (SEQ ID No. 16) coupled to KLH according to example 2. For the first injection, an emulsion of 1.5 ml of KLH-coupled peptide with 1.5 ml of complete Freund's adjuvant (Sigma #F-5881) is prepared and 1 ml of this latter emulsion (i.e. 200 μg of peptide) is injected intradermally into each of the rabbits. Two boosters are given, 20 days apart, by intradermal injection of 1 ml of an emulsion of KLH-coupled peptide (i.e. 200 μg of peptide) with incomplete Freund's adjuvant (Sigma #F-5506). Twenty days after the second booster, a third booster is given in the same way as the previous boosters, but by subcutaneous injection. Twenty days after the latter booster, and after evaluation of the antibody titer obtained, the rabbits are bled. More particularly, the polyclonal antibodies from the rabbits identified by the numbers #046 805 and 046 832, obtained by immunization with the peptide C-YTLRAPRSPKMVQGSG-NH$_2$ (SEQ ID No. 16) coupled to KLH, and from the rabbit identified by #L01235, obtained by immunization with the peptide C-YTLRAPRSPKMVQGS-NH$_2$ (SEQ ID No. 109) coupled to KLH, were used for the rest of the studies.

Example 4

Obtaining and Purifying the Antibodies

After purification, the rabbit sera are centrifuged for 30 minutes at 4500 rpm at 4° C. After separation by settling out, the serum is diluted by half in 1.5M glycine buffer, at pH 8.0, containing 1M NaCl.

Example 4.a

IgG Purification on Protein A-sepharose

The polyclonal antibody purification is carried out by affinity chromatography on a protein A-sepharose gel (Amersham Biosciences #17.1279.02). Protein A extracted from *Staphylococcus aureus* combines specifically with the Fc fragment of the IgG molecules. Next, the IgGs, all subclasses included, are eluted at pH 3.0.

All the buffers used are degassed for 15 minutes in an ultrasound bath before being used on the column, in order to prevent the formation of bubbles.

A chromatography column is prepared using 12 ml of protein A-sepharose. The gel column is equilibrated for 40 minutes with distilled and degassed water, and then for 40 minutes with Dulbecco PBS buffer, at pH 7.4, containing 0.5M NaCl and, finally, with 1.5M glycine buffer, at pH 8.0, containing 1M NaCl, until a correct baseline is obtained.

Next, 10 ml of rabbit serum diluted by half in 1.5M glycine buffer, at pH 8.0, containing 1M NaCl are passed through the column at a flow rate of 0.5 ml/min. After the appearance of the albumin peak, the serum IgGs are eluted by means of a 0.1M citric acid solution brought to pH 3.0 with 0.1M trisodium citrate buffer. The IgG elution peak is recovered and rapidly dialyzed in Dulbecco PBS buffer, at pH 7.4, overnight at 4° C. The IgG concentration is determined after dialysis by reading the optical density at 280 nm against PBS buffer.

Figure 1:
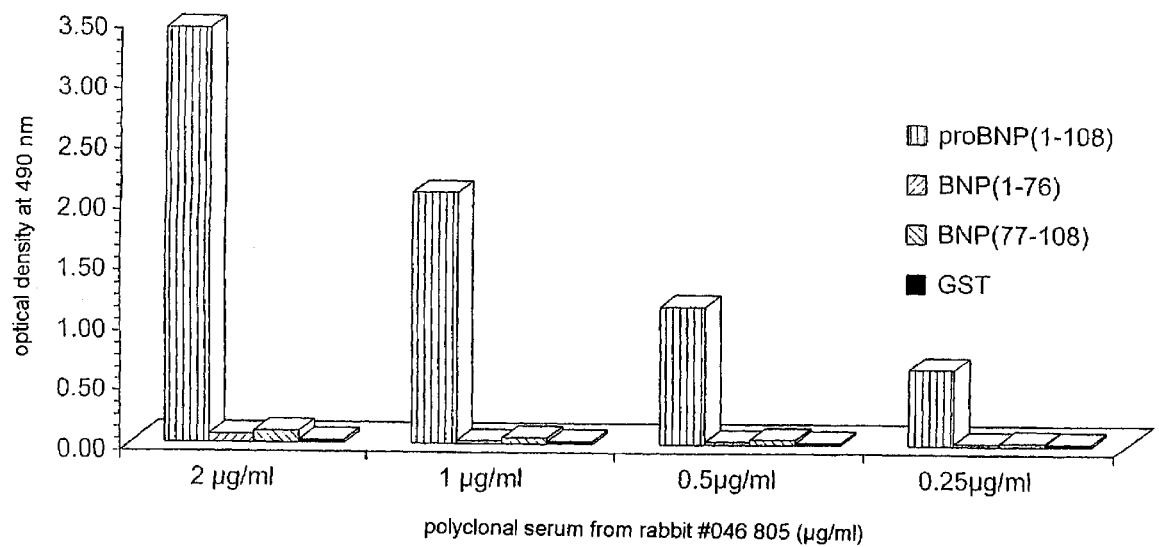
FIG. 1 represents the reactivity of the polyclonal antibodies from rabbit #046 805, purified on protein A-sepharose with proBNP(1-108), the BNP(1-76) fragment, BNP(77-108), or GST (glutathione-S-transferase, used as a control protein) adsorbed onto a microplate at 0.25 µg/ml.

After purification on protein A, the reactivity of the polyclonal antibodies is tested by ELISA on cupules coated either with proBNP(1-108), or with BNP(1-76), or with BNP(77-108), adsorbed at 0.25 µg/ml. The results obtained for the polyclonal antibodies from rabbit #046 805 are given in FIG. 1. The polyclonal antibodies from rabbit #046 832 gave identical results. The polyclonal antibodies from rabbits #046 805 and #046 832 are relatively specific for proBNP(1-108). We were, however, able to note the presence of a weak anti-BNP (77-108) reactivity at high concentrations, which reactivity we were able to eliminate by making the polyclonal antibodies from these rabbits monospecific by depletion on BNP-K$_3$-NHS-sepharose resin, according to the method described in example 4.b.

Example 4.b

Depletion of IgGs on BNP-K$_3$-NHS-sepharose Resin

The aim of this operation is to eliminate the cross reactivity observed with respect to BNP(77-108).

Since the cross reactivity of the polyclonal antibody that is obtained is located in the N-terminal position of the BNP(77-108) molecule, it was important to correctly present this region of BNP(77-108) to the immunoglobulins to be eliminated. For this purpose, the BNP(77-108) was synthesized with an extension of 3 lysine residues in the C-terminal position (BNP-K$_3$) in order to promote coupling thereof to the NHS-sepharose resin via its C-terminal end.

The BNP-K$_3$: S-P-K-M-V-Q-G-S-G-C-F-G-R-K-M-D-R-I-S-S-S-S-G-L-G-C-K-V-L-R-R-H-K-K-K (SEQ ID No. 104) was synthesized on a Pioneer synthesizer, using "Fmoc" (9-fluorenylmethyloxycarbonyl) chemistry, mentioned above in example 1.

5 mg of BNP-K$_3$ are dissolved using 100 mM NaHCO$_3$ buffer, at pH 8.3, to which 0.5M NaCl has been added, at a concentration of 10 mg/ml. 2 ml of NHS-sepharose resin (NHS-activated Sepharose 4 Fast Flow, Amersham Biosciences #17.0906.01) are centrifuged for 30 seconds at 1000 rpm at 4° C. The resin is washed with 15 ml of a cold 1 mM HCl solution. After centrifugation and removal of the HCl solution, the resin is mixed with the BNP-K$_3$ ligand at 10 mg/ml. The mixture is incubated for 1 hour at ambient temperature with slow stirring. After centrifugation and elimination of the ligand solution, the nonreactive groups of the resin are blocked with 5 ml of 0.1M glycine buffer, at pH 8.0. The mixture is incubated for 1 hour at ambient temperature with slow stirring. After centrifugation and removal of the blocking buffer, the resin is taken up with 5 ml of 100 mM NaHCO$_3$ buffer, at pH 8.3, to which 0.5M NaCl has been added. Four washes with this buffer are performed. After the final wash, the mixture is loaded onto a chromatography column.

Figure 2:
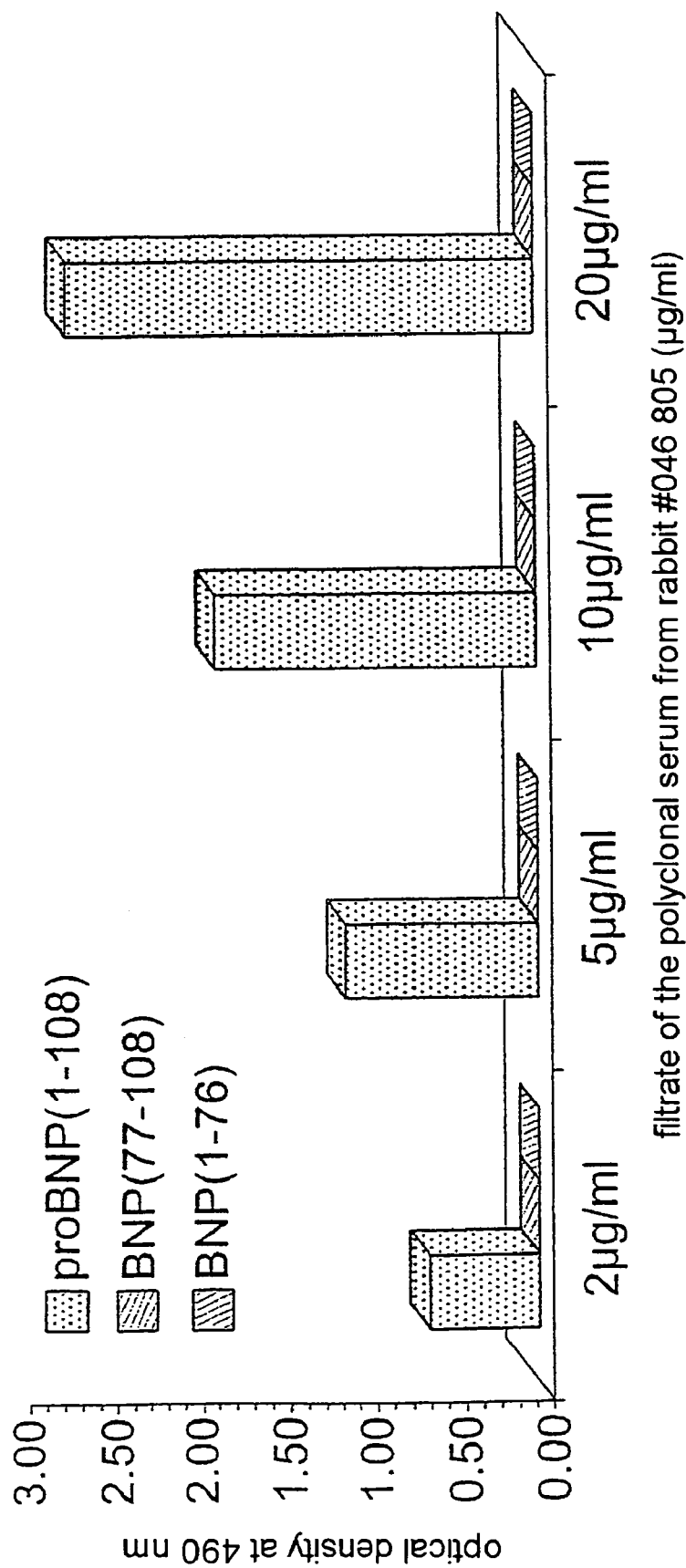
FIG. 2 represents the reactivity of the polyclonal antibodies of the filtrate of rabbit #046 805, obtained after depletion on $BNP-K_3$-NHS-sepharose resin. The polyclonal antibodies are prepared in the form of dilution ranges of 2 to 20 µg/ml, and then tested on cupules coated with proBNP(1-108), BNP(1-76) or BNP(77-108) polypeptide adsorbed at 0.25 µg/ml.
Figure 3:
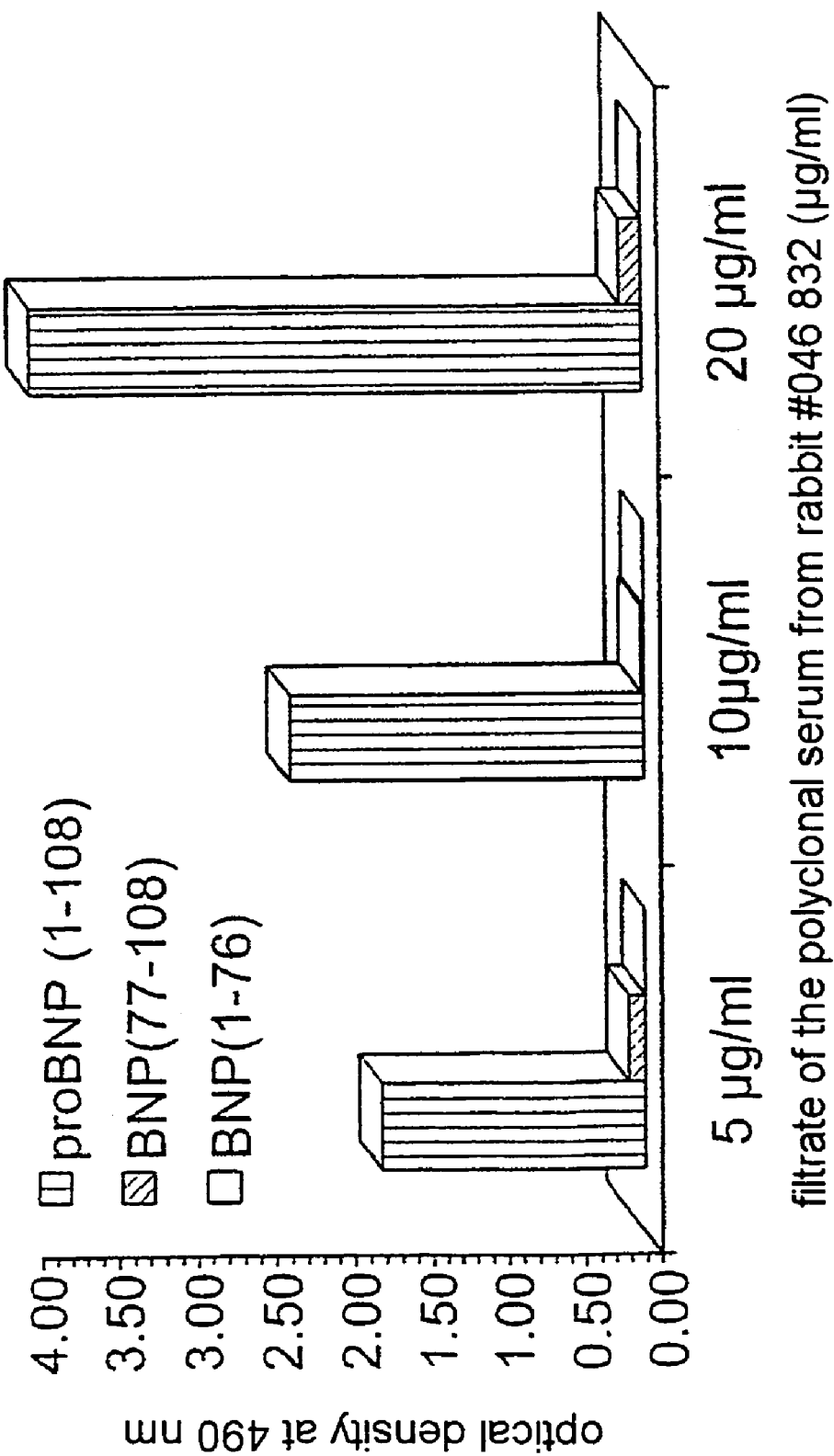
FIG. 3 represents the reactivity of the polyclonal antibodies of the filtrate of rabbit #046 832, obtained after depletion on $BNP-K_3$-NHS-sepharose resin. The polyclonal antibodies are prepared in the form of dilution ranges of 5 to 20 µg/ml, and then tested on cupules coated with proBNP(1-108), BNP(1-76) or BNP(77-108) polypeptide adsorbed at 0.25 µg/ml.
Figure 4:
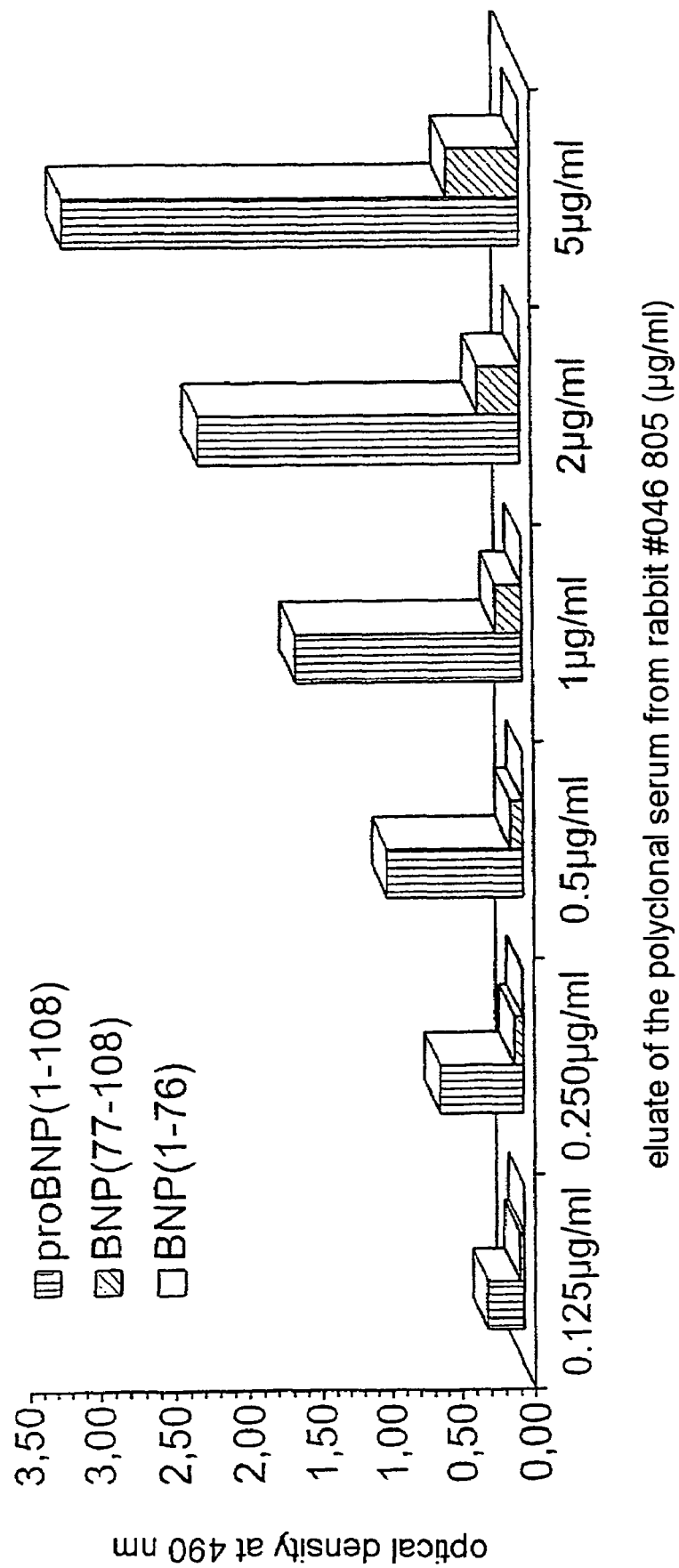
FIG. 4 represents the reactivity of the eluate of the polyclonal serum of rabbit #046 805, obtained after depletion on $BNP-K_3$-NHS-sepharose resin. The polyclonal antibodies are prepared in the form of dilution ranges of 2 to 20 µg/ml, and then tested on cupules coated with proBNP(1-108), BNP(1-76) or BNP(77-108) polypeptide adsorbed at 0.25 µg/ml.
Figure 5:
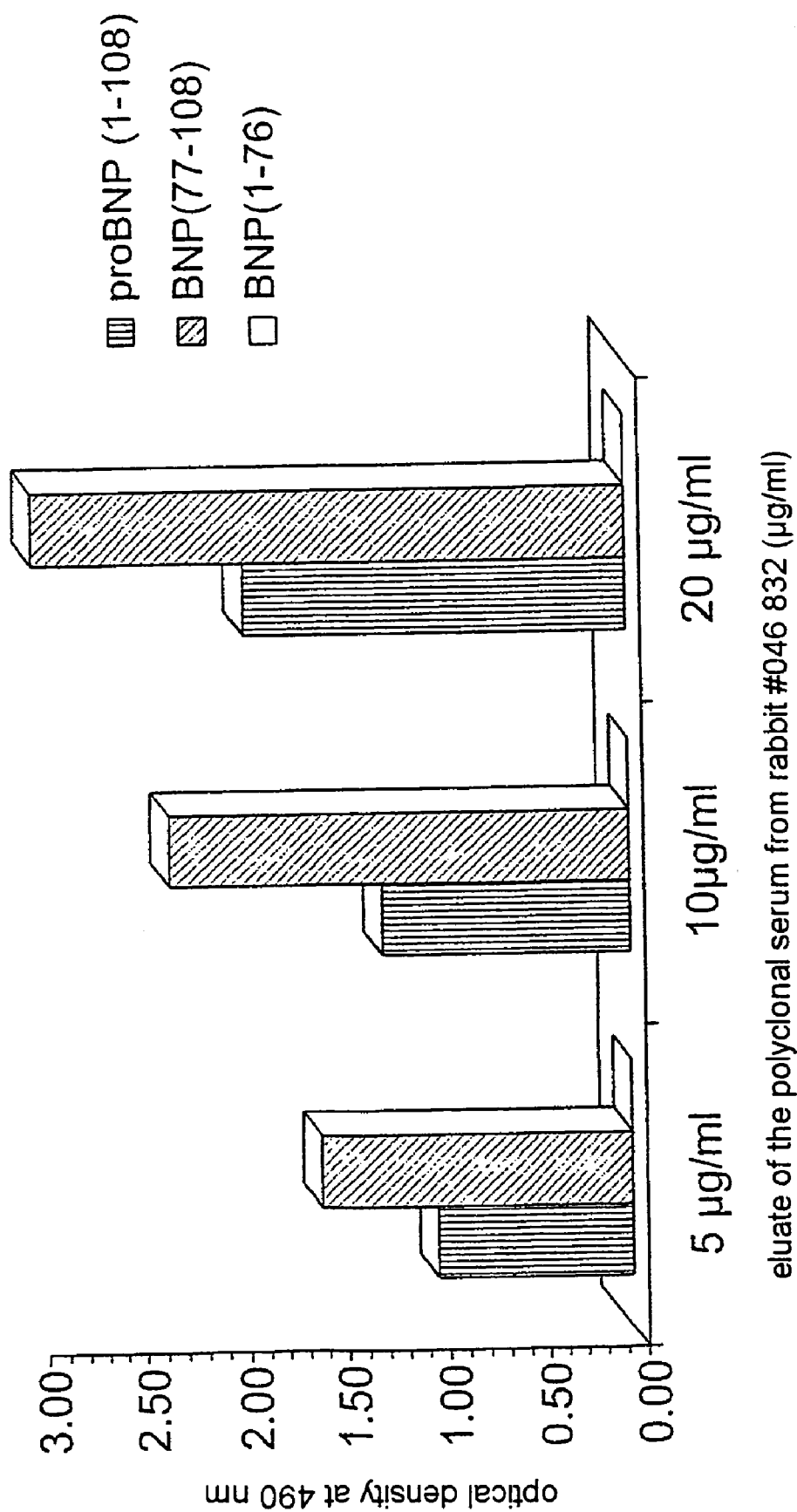
FIG. 5 represents the reactivity of the eluate of the polyclonal serum of rabbit #046 832, obtained after depletion on $BNP-K_3$-NHS-sepharose resin. The polyclonal antibodies are prepared in the form of dilution ranges of 5 to 20 µg/ml, and then tested on cupules coated with proBNP(1-108), BNP(1-76) or BNP(77-108) polypeptide adsorbed at 0.25 µg/ml.

After preparation of the chromatography column, 10 mg of IgG from rabbit #046 805 or from rabbit #046 832 are loaded onto the column. A peristaltic pump connected to the column makes it possible to circulate the rabbit serum IgGs overnight at 4° C. The following day, the IgG solution is recovered (=filtrate). The IgG fraction bound to the BNP-K$_3$ is eluted (=eluate) with 20 mM Tris buffer, at pH 8.0, containing 5M urea. The eluate and the filtrate are then tested in order to be sure of the effectiveness of the depletion. FIGS. 2 and 3 show the results of the tests carried out by ELISA with the filtrate of the polyclonal sera from rabbit #046 805 and #046 832, respectively. FIGS. 4 and 5 show the results of the tests carried out by ELISA with the eluate of the polyclonal sera from rabbit #046 805 and #046 832, respectively.

As was expected, the filtrate of the polyclonal sera from rabbit #046 805 and #046 832 is specific for proBNP(1-108): no reactivity is observed on BNP(1-76) nor on BNP(77-108). The eluate conserves a considerable reactivity with respect to proBNP(1-108) but also a reactivity with respect to BNP(77-108). These results confirm the effectiveness of the depletion of the rabbit polyclonal serum on the BNP-K$_3$-NHS-sepharose resin.

The BNP(77-108) comes from Sigma (#B-5900), while the proBNP(1-108) and the BNP(1-76) were produced in the form of recombined proteins expressed after cloning in the vector pGEX-2T (Amersham Pharmacia Biotech) and transfection in *E. coli*, by conventional techniques well known to those skilled in the art. The vector of origin was provided by the company Berlex Biosciences (Richmond, Calif., USA) and the preparation thereof is described by Yan et al. (PNAS, 2000, vol. 97, pp. 8525-8529). The concentration of proBNP (1-108) and that of BNP(1-76) were determined by the Bradford method for calorimetric protein assay (M. Bradford, Anal. Biochem. 1976; 72: 248-54).

Example 5

Determination of the Percentage Cross Reaction of the Anti-proBNP(1-108) Antibodies from Rabbits #046 805 and #L01235, with Respect to BNP(1-76) and to BNP(77-108)

Materials:
1) Solid phase: flat-bottomed Maxisorp microplate, Nunc (Denmark).
2) The BNP(77-108) comes from Sigma (#B-5900), while the proBNP(1-108) and the BNP(1-76) were produced in the form of recombined proteins. The concentration of these protein solutions was determined by the Bradford method for calorimetric assay of proteins (M. Bradford, Anal. Biochem. 1976; 72: 248-54).
3) The conjugate used is a peroxidase-coupled anti-rabbit IgG polyclonal antibody (Sigma #A-9169).
4) Saturation buffer: Dulbecco PBS buffer, at pH 7.4, containing 1% of bovine serum albumin (BSA, Sigma #A-7888).
5) Dilution buffer: Dulbecco PBS buffer, at pH 7.4, containing 0.1% of BSA and 0.1% of Tween 20.
6) Washing solution: Dulbecco PBS buffer at pH 7.4, containing 0.1% of Tween 20.
7) Visualizing solution: the visualizing solution is composed:
7a) of a substrate buffer: solution of 0.01M citric acid and of 0.04M trisodium citrate containing 0.33% $H_2O_2$, final pH 5.6, and
7b) of a chromogen: OPD (ortho-phenylenediamine) tablets. 1 OPD tablet to be dissolved in 10 ml of substrate buffer.
8) Stop solution: $4NH_2SO_4$.

Protocol:
The assay consists in evaluating the immunoreactivity of the polyclonal antibodies directly on the various proteins immobilized in the cupules of a microtitration plate.

Several coating solutions in Dulbecco PBS buffer, pH 7.4, are first of all prepared: a first containing BNP(77-108) at 0.25 μg/ml, a second containing proBNP(1-108) at 0.25 μg/ml, a third containing BNP(1-76) at 0.25 μg/ml, and a fourth containing GST (background noise control protein) at 0.25 μg/ml.

100 μl of each of these solutions are deposited separately in the wells of a microplate.

The microplate is incubated overnight at 4° C.

After removal of the coating solution, the microplate is washed with 300 μl of a Dulbecco PBS buffer, at pH 7.4, containing 0.1% of Tween 20, and then saturated by addition of 250 μl of Dulbecco PBS buffer, at pH 7.4, containing 1% of BSA.

The microplate is then incubated for 1 hour at 37° C.

The microplate is then washed (3 times) with the washing solution.

100 μl of polyclonal antibody solution, diluted beforehand to 2 and 1 μg/ml for the polyclonal serum from rabbit #046 805, and to 1/2500 and 1/5000 for the polyclonal serum from rabbit #L01235, are deposited in each cupule.

The reaction medium is incubated for 2 hours at ambient temperature.

The microplate is then washed 3 times with 300 μl of the washing solution.

100 μl of the peroxidase-coupled anti-rabbit IgG polyclonal antibody conjugate, diluted to 1/8000 in dilution buffer, are added to each well of the microplate.

The reaction medium is incubated for 1 hour at ambient temperature.

The plates are then washed (5 washes) with 300 μl of the washing solution. 100 μl of the visualizing solution are distributed into each cupule. The reaction is left to develop in the dark for 20 minutes at ambient temperature (18-24° C.).

50 μl of the stop solution are then distributed into each cupule.

After the reaction has been stopped, the optical density is read on a spectrophotometer at 490/620 nm.

Table I: Results of the Determination of the Percentage Cross Reaction of the Polyclonal Antibodies for Rabbits #046 805 and #L01235, with Respect to BNP(1-76) and to BNP(77-108)

For a given anti-proBNP(1-108) antibody, tested on BNP (77-108) adsorbed at 0.25 μg/ml, on proBNP(1-108) adsorbed at 0.25 μg/ml and on GST adsorbed at 0.25 μg/ml, the percentage cross reaction of the antibody with BNP (77-108) is calculated using the following formula:

$$\% = \frac{OD_{(BNP77-108)} - OD_{(GST)}}{OD_{(proBNP1-108)} - OD_{(GST)}} \times 100$$

For a given anti-proBNP(1-108) antibody, tested on BNP (1-76) adsorbed at 0.25 μg/ml, on proBNP(1-108) adsorbed at 0.25 μg/ml and on GST adsorbed at 0.25 μg/ml, the percentage cross reaction of the antibody with BNP(1-76) is calculated using the following formula:

$$\% = \frac{OD_{(BNP1-76)} - OD_{(GST)}}{OD_{(proBNP1-108)} - OD_{(GST)}} \times 100$$

|  | % cross reaction | | | |
| --- | --- | --- | --- | --- |
|  | Polyclonal serum #046 805 at 1 μg/ml | Polyclonal serum #046 805 at 2 μg/ml | Polyclonal serum #L01235 1/5000 | Polyclonal serum #L01235 1/2500 |
| BNP(77-108) to 0.25 μg/ml | 1.44% | 2.13% | 3.55% | 4.3% |
| BNP(1-76) to 0.25 μg/ml | 1.00% | 1.29% | 0.21% | 0.00% |

Conclusion: The cross reaction of the polyclonal antibodies of these sera is less than 2% on BNP(1-76) and less than 5% on BNP(77-108). The cross reactivity with respect to BNP(77-108) can be eliminated by means of the depletion method described in example 4.b. However, as is described in examples 19 and 20, under the conditions of an immunoenzymetric assay for proBNP(1-108), and at the concentrations of BNP(77-108) and of BNP(1-76) usually found in patients, these polyclonal antibodies can be used in their non-depleted version without resulting in the appearance of cross reaction.

Example 6

Identification of the Epitope Recognized by the Polyclonal Sera from Rabbits #046 805 and #046 832 Before and After Depletion on BNP-$K_3$-NHS-sepharose Resin The polyclonal sera from rabbits #046 805 and #046 832 before and after depletion on BNP-$K_3$-NHS-sepharose resin were tested by the spot method in order to identify the epitope recognized by these polyclonal sera. This method, described by Frank (Tetrahedron, 1992; 48: 9217-32), allows the rapid synthesis, on a nitrocellulose membrane, of a large number of peptides of predefined sequences. The protocols used are those described by Molina et al. (Pept. Res., 1996; 9: 151-5). Spots approximately 5 mm in diameter, comprising an aminated function, are created on a sheet of paper, which spots serve as an anchoring point for the C-terminal amino acid of the synthetic peptide. The peptide chain is extended by successive additions of activated Fmoc-amino acids. The amino acid side chains are blocked with appropriate chemical groups. All the peptides are synthesized with their N-terminal residue being N-acetylated. At the end of the synthesis, the side chains are deprotected through the action of trifluoroacetic acid. This treatment does not affect the binding between the peptide and the cellulose support, and the reactivity of the peptides can be evaluated by means of a colorimetric assay.

The series of peptides synthesized on a membrane consists of 32 pentadecapeptides with a 3-amino acid residue shift representing the entire sequence of proBNP(1-108).

TABLE II

Spot membrane consisting of 32 pentadecapeptides with a 3-amino acid residue shift representing the entire sequence of proBNP (1-108)

| Sequence | Spot No. | Sequence | Spot No. |
|---|---|---|---|
| HPLGSPGSASDLETS (SEQ ID No. 23) | 1 | GVWKSREVATEGIRG (SEQ ID No. 39) | 17 |
| GSPGSASDLETSGLQ (SEQ ID No. 24) | 2 | KSREVATEGIRGHRK (SEQ ID No. 40) | 18 |
| GSASDLETSGLQEQR (SEQ ID No. 25) | 3 | EVATEGIRGHRKMVL (SEQ ID No. 41) | 19 |
| SDLETSGLQEQRNHL (SEQ ID No. 26) | 4 | TEGIRGHRKMVLYTL (SEQ ID No. 42) | 20 |
| ETSGLQEQRNHLQGK (SEQ ID No. 27) | 5 | IRGHRKMVLYTLRAP (SEQ ID No. 43) | 21 |
| GLQEQRNHLQGKLSE (SEQ ID No. 28) | 6 | HRKMVLYTLRAPRSP (SEQ ID No. 44) | 22 |
| EQRNHLQGKLSELQV (SEQ ID No. 29) | 7 | MVLYTLRAPRSPKMV (SEQ ID No. 45) | 23 |
| NHLQGKLSELQVEQT (SEQ ID No. 30) | 8 | YTLRAPRSPKMVQGS (SEQ ID No. 46) | 24 |
| QGKLSELQVEQTSLE (SEQ ID No. 31) | 9 | RAPRSPKMVQGSGCF (SEQ ID No. 47) | 25 |
| LSELQVEQTSLEPLQ (SEQ ID No. 32) | 10 | RSPKMVQGSGCFGRK (SEQ ID No. 48) | 26 |
| LQVEQTSLEPLQESP (SEQ ID No. 33) | 11 | KMVQGSGCFGRKMDR (SEQ ID No. 49) | 27 |
| EQTSLEPLQESPRPT (SEQ ID No. 34) | 12 | QGSGCFGRKMDRISS (SEQ ID No. 50) | 28 |
| SLEPLQESPRPTGVW (SEQ ID No. 35) | 13 | GCFGRKMDRISSSSG (SEQ ID No. 51) | 29 |
| PLQESPRPTGVWKSR (SEQ ID No. 36) | 14 | GRKMDRISSSSGLGC (SEQ ID No. 52) | 30 |
| ESPRPTGVWKSREVA (SEQ ID No. 37) | 15 | MDRISSSSGLGCKVL (SEQ ID No. 53) | 31 |
| RPTGVWKSREVATEG (SEQ ID No. 38) | 16 | ISSSSGLGCKVLRRH (SEQ ID No. 54) | 32 |

Figure 6:
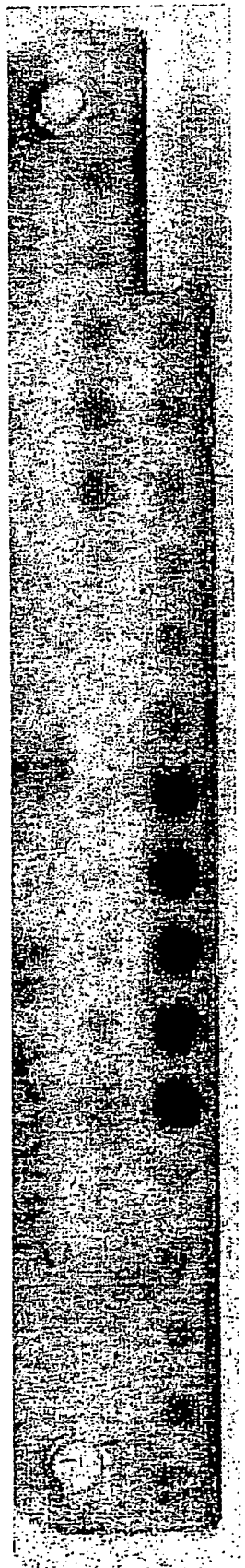
FIG. 6 represents an epitope analysis, by means of the spot technique, of the polyclonal serum from rabbit #046 805 before depletion (for this example, the background noise is 30.4±5.93 relative intensity units).
Figure 7:
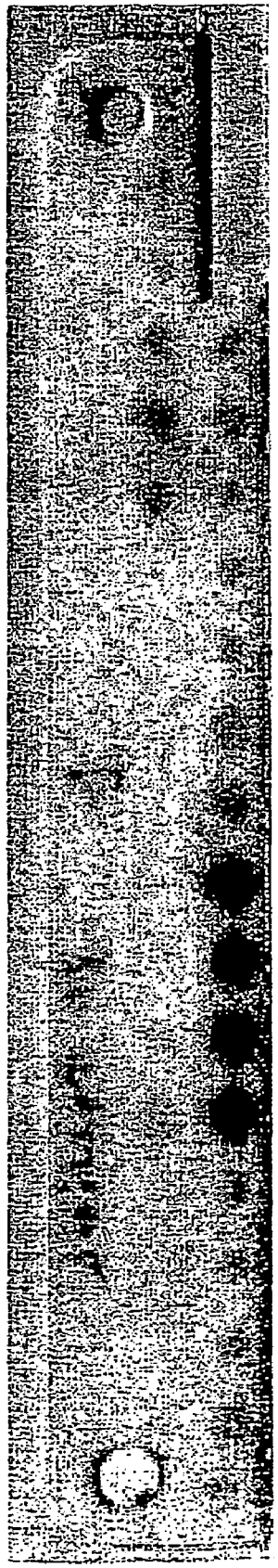
FIG. 7 represents an epitope analysis, by means of the spot technique, of the polyclonal serum from rabbit #046 805 after depletion on $BNP-K_3$-NHS-sepharose resin (for this example, the background nose is 31.3±6.31 relative intensity units).

After saturation of the membrane with 30 ml of TBS (Tris buffered saline) buffer, at pH 7.0, to which has been added 0.1% Tween 20, 5% blocking buffer (Euromedex #SU-07-250), and 5% sucrose, the reactivity of 20 ml of the rabbit polyclonal serum diluted to 10 μg/ml is tested (over an incubation of 1 hour 30 minutes at 37° C. with agitation). After washing with the TBS buffer at pH 7.0, to which 0.1% Tween 20 has been added, 20 ml of alkaline phosphatase-coupled anti-rabbit IgG conjugate (Sigma #A-8025) are incubated for 1 hour at ambient temperature with agitation. Finally, after a last series of washes with 30 ml of washing solution, the spots are visualized by addition of 30 ml of substrate solution (solution of 30 ml of CBS (citrate buffered saline) buffer, at pH 7.0, containing 120 μl of 0.15M BCIP (5-bromo-4-chloro-3-indolyl phosphate), 150 μl of 1M $MgCl_2$ and 180 μl of 0.1M MTT (thiazolyl blue tetrazolium bromide)). After scanning of the membrane, the intensity of the spots on the membrane is evaluated (in relative intensity units) using image processing software. The background noise is calculated from the spots not detected by the antiserum. The results of the epitope analysis for the polyclonal serum from rabbit #046 805 before depletion are given in FIG. 6. Five peptides (spots 22 to 26) are detected by the polyclonal serum, and the sequence common to these five peptides is $R_{76}S_{77}P$. However, the reactivity is clearly increased when the RAP unit is added at the N-terminal position of the $R_{76}S_{77}P$ unit. The results of the epitope analysis for the polyclonal serum from rabbit #046 805 after depletion on BNP-$K_3$-NHS-sepharose resin are given in FIG. 7. Four peptides (spots 22 to 25) are detected by the polyclonal serum, and the sequence common to these four peptides is $RAPR_{76}S_{77}P$. Unlike that which is observed for the polyclonal serum before depletion, no reactivity on the $R_{76}S_{77}P$ unit alone is observed (spot 26). This explains that, after depletion on BNP-$K_3$-NHS-sepharose resin, the polyclonal serum no longer detects BNP(77-108) [as a reminder, the $S_{77}P$ unit corresponds to the first two amino acids of the sequence of BNP(77-108)]. In conclusion, the epitope recognized by the polyclonal serum from rabbit #046 805 made monospecific is $RAPR_{76}S_{77}P$.

Entirely identical results were obtained using the polyclonal serum from rabbit #046 832: the epitope recognized by the polyclonal serum from this rabbit, made monospecific, is also RAPR$_{76}$S$_{77}$P.

Example 7

Identification of the Minimum Epitope of the Polyclonal Sera from Rabbits #046 805 and #046 832 Before and After Depletion, by the Ala-scan Method The polyclonal sera from rabbits #046 805 and #046 832, before and after depletion on BNP-K$_3$-NHS-sepharose resin, were tested by the spot method (described in example 6) in order to identify the minimum epitope, in the hinge peptide, that allows specific recognition of only proBNP(1-108) by the polyclonal sera. A membrane was synthesized, consisting of 16 pentadecapeptides repeating the sequence of the hinge peptide YTLRAPRSPKMVQGS and bearing a substitution, from neighbor-to-neighbor, of an amino acid with an alanine residue (alanine-scanning or "Ala-scan") or glycine residue, the substitution being each time shifted to the right by one amino acid residue (table III). The results of the Ala-scan analysis of the polyclonal sera from rabbits #046 805 and #046 832 before and after depletion on BNP-K$_3$-NHS-sepharose resin are given in table III.

TABLE III

Spot membrane containing 16 pentadecapeptides YTLRAPRSPKMVQGS bearing a substitution, from neighbor-to-neighbor, of each amino acid with an alanine or glycine residue. Reactivity of the polyclonal sera from rabbits #046 805 and #046 832 before and after depletion on BNP-K$_3$-NHS-sepharose resin

| SEQ ID | Sequence | Spot No. | Reactivity (in relative intensity units) polyclonal serum rabbit #046 805 not depleted | Reactivity (in relative intensity units) polyclonal serum rabbit #046 805 depleted | Reactivity (in relative intensity units) polyclonal serum rabbit #046 832 not depleted | Reactivity (in relative intensity units) polyclonal serum rabbit #046 832 depleted |
|---|---|---|---|---|---|---|
| SEQ ID No. 46 | YTLRAPRSPKMVQGS | 716 | 84 | 69 | 151 | 132 |
| SEQ ID No. 55 | ATLRAPRSPKMVQGS | 717 | 90 | 68 | 148 | 130 |
| SEQ ID No. 56 | YALRAPRSPKMVQGS | 718 | 101 | 71 | 154 | 130 |
| SEQ ID No. 57 | YTARAPRSPKMVQGS | 719 | 108 | 77 | 152 | 133 |
| SEQ ID No. 58 | YTLAAPRSPKMVQGS | 720 | 101 | 39 | 148 | 106 |
| SEQ ID No. 59 | YTLRGPRSPKMVQGS | 721 | 93 | 39 | 156 | 132 |
| SEQ ID No. 60 | YTLRAARSPKMVQGS | 722 | 103 | 96 | 137 | 48 |
| SEQ ID No. 61 | YTLRAPASPKMVQGS | 723 | 50 | 23 | 150 | 116 |
| SEQ ID No. 62 | YTLRAPRAPKMVQGS | 724 | 58 | 44 | 148 | 113 |
| SEQ ID No. 63 | YTLRAPRSAKMVQGS | 725 | 74 | 41 | 85 | 67 |
| SEQ ID No. 64 | YTLRAPRSPAMVQGS | 726 | 138 | 118 | 157 | 148 |
| SEQ ID No. 65 | YTLRAPRSPKAVQGS | 727 | 98 | 77 | 150 | 130 |
| SEQ ID No. 66 | YTLRAPRSPKMAQGS | 728 | 100 | 68 | 138 | 130 |
| SEQ ID No. 67 | YTLRAPRSPKMVAGS | 729 | 95 | 71 | 142 | 133 |
| SEQ ID No. 68 | YTLRAPRSPKMVQAS | 730 | 107 | 78 | 143 | 134 |
| SEQ ID No. 69 | YTLRAPRSPKMVQGA | 731 | 112 | 68 | 153 | 132 |

NB: The alanine or glycine residues substituted for the initial amino acids are underlined (A and G).

The amino acids that are essential in the recognition of the epitope recognized by the polyclonal serum from rabbit #046 805 before depletion are $R_{76}S_{77}P$, whereas, after depletion of the polyclonal serum from rabbit #046 805 on BNP-$K_3$-NHS-sepharose resin, besides the $R_{76}S_{77}P$ unit, the RA unit becomes a contributor. For the polyclonal serum from rabbit #046 832 before depletion, only the proline $P_{78}$ contributes, whereas, after depletion of the polyclonal serum from rabbit #046 832 on BNP-$K_3$-NHS-sepharose resin, the contributing unit is R-P$R_{76}S_{77}P$. These results therefore show that the obligatory minimum epitope in the specific recognition of proBNP(1-108) by the polyclonal antibodies from rabbits #046 805 and #046 832 is RAP$R_{76}S_{77}P$.

Example 8

Identification of the Minimum Epitope of the Polyclonal Serum from Rabbit #L01235, by the Ala-scan Method The polyclonal serum from rabbit #L01235, specific for proBNP(1-108) from the start (no need for depletion), was tested by the spot method (described in example 6) in order to identify the minimum epitope, in the hinge peptide, allowing specific recognition of only proBNP(1-108) by the polyclonal serum. The membrane used is that described in example 7. The results of the Ala-scan analysis of the polyclonal serum from rabbit #L01235 are given in table IV.

TABLE IV

Spot membrane containing 16 pentadecapeptides YTLRAPRSPKMVQGS bearing a substitution, from neighbor-to-neighbor, of each amino acid with an alanine or glycine residue. Reactivity of the polyclonal serum from rabbit #L01235.

| SEQ ID | Sequence | Reactivity (in relative intensity units) polyclonal serum from rabbit #L01235 |
|---|---|---|
| SEQ ID No. 46 | YTLRAPRSPKMVQGS | 94 |
| SEQ ID No. 55 | ATLRAPRSPKMVQGS | 91 |
| SEQ ID No. 56 | YALRAPRSPKMVQGS | 84 |
| SEQ ID No. 57 | YTARAPRSPKMVQGS | 92 |
| SEQ ID No. 58 | YTLAAPRSPKMVQGS | 66 |
| SEQ ID No. 59 | YTLRGPRSPKMVQGS | 71 |
| SEQ ID No. 60 | YTLRAARSPKMVQGS | 67 |
| SEQ ID No. 61 | YTLRAPASPKMVQGS | 71 |
| SEQ ID No. 62 | YTLRAPRAPKMVQGS | 47 |
| SEQ ID No. 63 | YTLRAPRSAKMVQGS | 53 |
| SEQ ID No. 64 | YTLRAPRSPAMVQGS | 102 |
| SEQ ID No. 65 | YTLRAPRSPKAVQGS | 73 |
| SEQ ID No. 66 | YTLRAPRSPKMAQGS | 70 |
| SEQ ID No. 67 | YTLRAPRSPKMVAGS | 70 |

TABLE IV-continued

Spot membrane containing 16 pentadecapeptides YTLRAPRSPKMVQGS bearing a substitution, from neighbor-to-neighbor, of each amino acid with an alanine or glycine residue. Reactivity of the polyclonal serum from rabbit #L01235.

| SEQ ID | Sequence | Reactivity (in relative intensity units) polyclonal serum from rabbit #L01235 |
|---|---|---|
| SEQ ID No. 68 | YTLRAPRSPKMVQAS | 83 |
| SEQ ID No. 69 | YTLRAPRSPKMVQGA | 80 |

NB: The alanine or glycine residues substituted for the initial amino acids are underlined (A and G).

As for the polyclonal sera from rabbits #046 805 and #046 832 (example 7), these results show that the obligatory minimum epitope in the specific recognition of proBNP(1-108) by the polyclonal antibodies from rabbit #L01235 is RAP$R_{76}S_{77}P$.

Example 9

Immunization of Mice with the proBNP(1-108) Recombined Protein

Mice of the BALB/c strain (6-week-old females) were immunized with the recombined proBNP(1-108) described in example 4.b, by conventional techniques well known to those skilled in the art. At the first injection, an emulsion of 1 ml of proBNP(1-108) with 1 ml of complete Freund's adjuvant (Sigma #F-5881) is prepared, and 300 µl of this emulsion (i.e. 100 µg of protein) are injected subcutaneously into each of the mice. Two boosters are given 15 days apart by intraperitoneal injection of 300 µl of an emulsion of proBNP(1-108) (i.e. 100 µg of protein) with incomplete Freund's adjuvant (Sigma #F-5506). Fifteen days after the second booster, a third booster is given in the same way as the previous ones, but by subcutaneous injection. Finally, 15 days after the last booster, blood samples are taken from the mice in order to analyze the immune response by the spot technique. The immune response of mouse 12 proves to be particularly advantageous for the remainder of the studies.

Example 10

Identification of the Epitopes Recognized by the Polyclonal Antibodies from Mouse 12 on the Sequence of proBNP(1-108)

The spot method used to identify the epitopes recognized by the polyclonal antibodies from mouse 12 on a sequence of proBNP(1-108) is described in example 6.

The series of peptides synthesized on the membrane consists of 94 pentadecapeptides, each shifted by one amino acid residue, representing the entire sequence of proBNP(1-108). The reactivity of the polyclonal serum from mouse 12, diluted to 1/500, is tested on this membrane, as described in example 6. After scanning of the membrane, the intensity of the spots on the membrane is evaluated (relative intensity units) by means of image processing software. The background noise, calculated from the spots not detected by the antiserum, was 30 relative intensity units.

Three regions located in the N-terminal position of the sequence of proBNP(1-108) are thus particularly well detected by the antibodies of the antiserum from mouse 12: sequence $H_1PLGSPGSASDLETS_{15}$ (SEQ ID No. 23) (spots 1 to 12), sequence $L_{17}QEQRNHLQGK_{27}$ (SEQ ID No. 123) (spots 17 to 27) and sequence $L_{38}EPLQESPRPTG_{49}$ (SEQ ID No. 124) (spots 38 to 49).

Surprisingly, the antiserum from mouse 12 also contains antibodies capable of recognizing spots in which the peptide sequence comprises the $RAPR_{76}S_{77}P$ unit: spots 64 to 68. The peptide sequences of the spots are described in table V.

TABLE V

Epitopes of the hinge region recognized, using the spot technique, by the antiserum from mouse 12

| Spot No. | Peptide sequence of the spot detected | Reactivity in relative intensity units | Spot No. | Peptide sequence of the spot detected | Reactivity in relative intensity units |
| --- | --- | --- | --- | --- | --- |
| 1 | HPLGSPGSASDLETS (SEQ ID No. 23) | 177.0 | 38 | LEPLQESPRPTGVWK (SEQ ID No. 88) | 177.0 |
| 2 | PLGSPGSASDLETSG (SEQ ID No. 70) | 170.0 | 39 | EPLQESPRPTGVWKS (SEQ ID No. 89) | 188.0 |
| 3 | LGSPGSASDLETSGL (SEQ ID No. 71) | 145.7 | 40 | PLQESPRPTGVWKSR (SEQ ID No. 90) | 109.0 |
| 4 | GSPGSASDLETSGLQ (SEQ ID No. 24) | 166.3 | 41 | LQESPRPTGVWKSRE (SEQ ID No. 91) | 166.0 |
| 5 | SPGSASDLETSGLQE (SEQ ID No. 72) | 185.0 | 42 | QESPRPTGVWKSREV (SEQ ID No. 92) | 164.0 |
| 6 | PGSASDLETSGLQEQ (SEQ ID No. 73) | 169.3 | 43 | ESPRPTGVWKSREVA (SEQ ID No. 93) | 147.0 |
| 7 | GSASDLETSGLQEQR (SEQ ID No. 25) | 155.2 | 44 | ESPRPTGVWKSREVA (SEQ ID No. 93) | 149.0 |
| 8 | SASDLETSGLQEQRN (SEQ ID No. 74) | 176.5 | 45 | SPRPTGVWKSREVAT (SEQ ID No. 94) | 175.0 |
| 9 | ASDLETSGLQEQRNH (SEQ ID No. 75) | 108.0 | 46 | PRPTGVWKSREVATE (SEQ ID No. 95) | 186.0 |
| 10 | SDLETSGLQEQRNHL (SEQ ID No. 76) | 118.3 | 47 | RPTGVWKSREVATEG (SEQ ID No. 16) | 171.0 |
| 11 | DLETSGLQEQRNHLQ (SEQ ID No. 77) | 121.0 | 48 | PTGVWKSREVATEGI (SEQ ID No. 96) | 148.0 |
| 12 | LETSGLQEQRNHLQG (SEQ ID No. 78) | 101.0 | 49 | TGVWKSREVATEGIR (SEQ ID No. 97) | 72.0 |
| 17 | LQEQRNHLQGKLSEL (SEQ ID No. 79) | 99.0 | 61 | IRGHRKMVLYTLRAP (SEQ ID No. 98) | 105.8 |
| 18 | QEQRNHLQGKLSELQ (SEQ ID No. 80) | 179.8 | 62 | RGHRKMVLYTLRAPR (SEQ ID No. 99) | 97.7 |
| 19 | EQRNHLQGKLSELQV (SEQ ID No. 29) | 189.6 | 63 | GHRKMVLYTLRAPRS (SEQ ID No. 100) | 95.9 |
| 20 | QRNHLQGKLSELQVE (SEQ ID No. 81) | 211.8 | 64 | HRKMVLYTLRAPRSP (SEQ ID No. 53) | 92.8 |
| 21 | RNHLQGKLSELQVEQ | 219.0 | 65 | RKMVLYTLRAPRSPK (SEQ ID No. 101) | 48.0 |
| 22 | NHLQGKLSELQVEQT (SEQ ID No. 30) | 213.3 | 66 | KMVLYTLRAPRSPKM (SEQ ID No. 102) | 48.0 |
| 23 | HLQGKLSELQVEQTS (SEQ ID No. 83) | 202.6 | 67 | MVLYTLRAPRSPKMV (SEQ ID No. 45) | 42.1 |
| 24 | LQGKLSELQVEQTSL (SEQ ID No. 84) | 189.5 | 68 | VLYTLRAPRSPKMVQ (SEQ ID No. 103) | 38.4 |

TABLE V-continued

Epitopes of the hinge region recognized, using the spot technique, by the antiserum from mouse 12

| Spot No. | Peptide sequence of the spot detected | Reactivity in relative intensity units | Spot No. | Peptide sequence of the spot detected | Reactivity in relative intensity units |
|---|---|---|---|---|---|
| 25 | QGKLSELQVEQTSLE (SEQ ID No. 85) | 187.3 | | | |
| 26 | GKLSELQVEQTSLEP (SEQ ID No. 86) | 36.6 | | | |
| 27 | KLSELQVEQTSLEPL (SEQ ID No. 87) | 69.9 | | | |

Example 11

Production of Monoclonal Antibodies that Specifically Recognize proBNP(1-108), with the Substantial Exclusion of BNP(1-76) and of BNP(77-108)

The mouse (5-week-old BALB/c female) selected for the production of monoclonal antibodies was immunized with the peptide SEQ ID No. 16 C-YTLRAPRSPKMVQGSG-NH$_2$ (C13P30) coupled to KLH (keyhole limpet hemocyanin) according to the following protocol: 100 µg of the KLH-coupled peptide diluted volume-for-volume with complete Freund's adjuvant were injected subcutaneously. Four boosters were given, three weeks apart, with 100 µg of the KLH-coupled peptide diluted volume-for-volume with incomplete Freund's adjuvant, injected subcutaneously.

Three days before lymphocyte fusion was to be performed, the mouse underwent a hyperimmunization according to the following protocol: the total dose of immunogen, in this case 100 µg of peptide C-YTLRAPRSPKMVQGSG-NH$_2$ coupled to KLH in sterile PBS buffer, is fractionated into four injections. The first and the second injections each correspond to 1/10 of the total dose. These injections are given subcutaneously at various sites, and 45 minutes apart. The third injection, which corresponds to 2/10 of the total dose, is given 45 minutes after the second injection, subcutaneously. Thirty minutes after the third injection, an intraperitoneal injection of 100 µl of a 1 mg/ml solution of promethazine in sterile PBS (2.5% Phenergan, Laboratoires Medeva Parma) is given in order to prevent any anaphylactic shock. Finally, 15 minutes later, the last injection corresponding to 6/10 of the total dose is given intraperitoneally.

The lymphocyte hybridization is carried out according to the method described by Köhler and Milstein (Nature, 1975; 256: 495-97). It is carried out using lymphocyte cells extracted from the spleen of the mouse and myeloma cells (P3-X63-Ag8.653) placed in culture beforehand in RPMI 1640 medium (Bio-Whittaker #BE 12/167F), supplemented with a mixture of L-glutamine, penicillin and streptomycin (Sigma #G-6784), to which have been added 10% of fetal calf serum, decomplemented beforehand (Bio-Whittaker #BE02701E), and 8-azaguanine (Sigma #A-8526). The lymphocyte cells and the myeloma cells, placed beforehand in RPMI-1640 medium (Bio-Whittaker #BE12-167F) supplemented with a mixture of L-glutamine, penicillin and streptomycin (Sigma #G-6784) without the addition of fetal calf serum, are mixed in a proportion of 5 lymphocyte cells per myeloma cell. After centrifugation of the mixture for 7 minutes at 900 rpm at ambient temperature, and resuspension of the cell pellet, 1 ml of Hybri-Max® polyethylene glycol (Sigma #P-7777) is added. After incubation for 1 minute in a waterbath at 37° C., the cells are centrifuged for 1 minute 30 seconds at 1000 rpm at ambient temperature. Finally, after incubation for 2 minutes in a waterbath at 37° C., the pellet is resuspended and 6 ml of RPMI 1640 medium (Bio-Whittaker #BE12-167F) supplemented with a mixture of L-glutamine, penicillin and streptomycin (Sigma #G-6784), placed at 37° beforehand, are added at a rate of 100 µl every 5 seconds, and 9 ml of this same medium are added all at once. After centrifugation for 10 minutes at 900 rpm at ambient temperature, and removal of the supernatant, the pellet is taken up with RPMI 1640 medium (Bio-Whittaker #BE12-167F), supplemented with a mixture of L-glutamine, penicillin and streptomycin (Sigma #G-6784), to which have been added 15% of fetal calf serum, decomplemented beforehand (Bio-Whittaker #BE02701E), and HAT (hypoxanthine, aminopterin, thymidine, Sigma #H-0262), so as to distribute, in 100 µl, 120 000 cells per well. The solution is deposited, in 100 µl, in the wells of the 96-well culture plates seeded beforehand with murine macrophages. The plates are then placed in a $CO_2$ incubator. Fifteen days after the lymphocyte hybridization, the number of clones present in the fusion plates is estimated and expressed as percentage development of hybridomas.

The selection of the hybridomas is carried out by ELISA on proBNP(1-108), BNP(1-76), BNP(77-108) and a peptide bearing the sequence RAPR$_{76}$S$_{77}$P(C13P30). Only the hybridomas secreting antibodies capable of detecting proBNP(1-108) and the C13P30 peptide bearing the sequence RAPR$_{76}$S$_{77}$P and not substantially recognizing BNP(1-76) or BNP(77-108) are selected. The hybridomas selected are maintained in culture and cloned by limiting dilution. The hybridomas thus cloned can then be used for producing the monoclonal antibody in ascites fluid.

In this way, the inventors produced a murine hybridoma, clone 3D4, that secretes an immunoglobulin of isotype IgG$_1$κ having the characteristics of the antibodies according to the invention. This hybridoma was deposited, on Jul. 31, 2003, with the CNCM (Collection Nationale de Cultures de Microorganismes [National Collection of Microorganism Cultures], Pasteur Institute, 25 rue du Docteur Roux, 75 724 Paris, Cedex 15, France) under the registration number CNCM I-3073.

Subjects of the invention are therefore also the hybridoma 3D4 deposited with the CNCM under the registration number CNCM I-3073, and the monoclonal antibody that it secretes.

Example 12

Validation by ELISA of the Specificity of The Antibody Produced by the Hybridoma 3D4

Materials:
1) Solid phase: flat-bottomed Maxisorp microplate, Nunc (Denmark)
2) The BNP(77-108) comes from Sigma (#B-5900), while the proBNP(1-108) and the BNP(1-76) were produced in the form of recombined proteins. The concentration of these protein solutions was determined by the Bradford method for calorimetric assay of proteins (M. Bradford, Anal. Biochem. 1976; 72: 248-54).
3) The conjugate used is a peroxidase-coupled donkey anti-mouse IgG polyclonal antibody (Jackson Immunoresearch #715-035-150).
4) Saturation buffer: Dulbecco PBS buffer, at pH 7.4, containing 1% of bovine serum albumin (BSA, Sigma #A-7888).
5) Dilution buffer: Dulbecco PBS buffer, at pH 7.4, containing 0.1% of BSA and 0.1% of Tween 20.
6) Washing solution: Dulbecco PBS buffer, at pH 7.4, containing 0.1% of Tween 20.
7) Visualizing solution: The visualizing solution is composed:
7a) of a substrate buffer (solution of 0.01M citric acid and of 0.04M trisodium citrate containing 0.33% $H_2O_2$, final pH 5.6, and
7b) of a chromogen: OPD (ortho-phenylenediamine) tablets. 1 OPD tablet to be dissolved in 10 ml of substrate buffer.
8) Stop solution: 4N $H_2SO_4$.

Protocol:

The assay consists in evaluating the immunoreactivity of the culture supernatant of the hybridoma 3D4 directly on the various proteins immobilized in the cupules of a microtitration plate.

Several coating solutions in Dulbecco PBS buffer, pH 7.4, are first of all prepared: a first containing BNP(77-108) at 1 µg/ml, a second containing proBNP(1-108) at 1 µg/ml, and a third containing BNP(1-76) at 1 µg/ml.

100 µl of each of these solutions are deposited separately in the wells of a microplate.

The microplate is incubated overnight at 4° C.

After removal of the coating solution, the microplate is washed with a Dulbecco PBS buffer, at pH 7.4, containing 0.1% of Tween 20, and then saturated by addition of 250 µl of Dulbecco PBS buffer, at pH 7.4, containing 1% of BSA.

The microplate is then incubated for 1 hour at 37° C.

The microplate is then washed (3 times) with 300 µl of the washing solution.

100 µl of hybridoma 3D4 supernatant, diluted beforehand to ½ in the dilution buffer, are deposited in each cupule.

The reaction medium is incubated for 2 hours at ambient temperature.

The microplate is then washed 3 times with 300 µl of the washing solution.

100 µl of conjugate, peroxidase-coupled anti-mouse IgG polyclonal diluted to 1/2000 in dilution buffer, are added to each well of the microplate.

The reaction medium is incubated for 1 hour at ambient temperature.

The plates are then washed (5 washes) with 300 µl of the washing solution. 100 µl of the visualizing solution are distributed in each cupule. The reaction is left to develop in the dark for 20 minutes at ambient temperature (18-24° C.).

50 µl of the stop solution are then distributed into each cupule.

After the reaction has been stopped, the optical density is read on a spectrophotometer at 490/620 nm.

Figure 8:
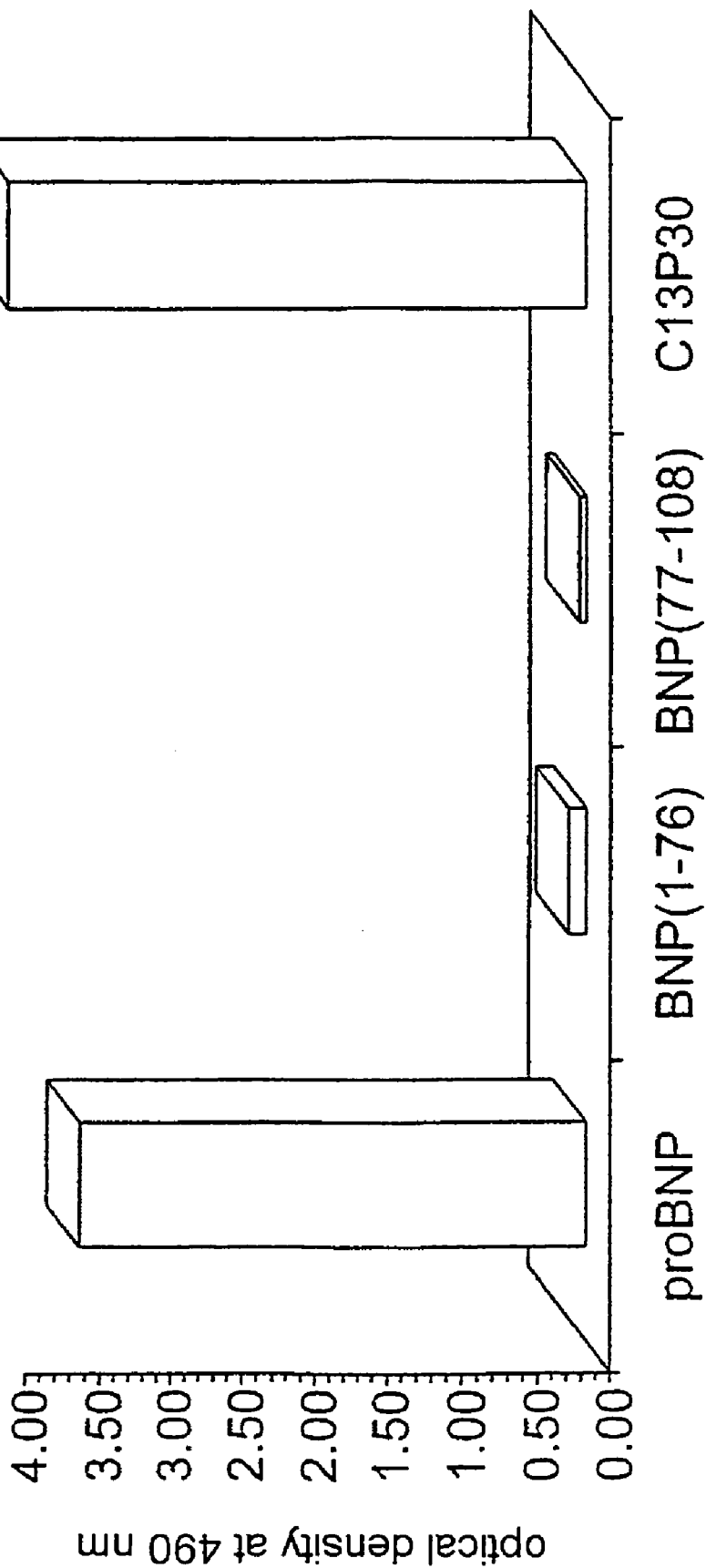
FIG. 8 represents the reactivity of the culture supernatant of the hybridoma 3D4 diluted to ½, tested on cupules coated either with proBNP(1-108), or with BNP(1-76), or with BNP(77-108), or with peptide YTLRAPRSPKMVQGSG (C13P30), adsorbed at 1 µg/ml.

FIG. 8 illustrates the result of this assay: the antibody produced in the hybridoma 3D4 supernatant is capable of detecting only proBNP(1-108) and the C13P30 immunizing peptide, no reactivity is obtained on BNP(1-76) or on BNP (77-108). These results validate the specificity of the antibody produced by the hybridoma 3D4 for proBNP(1-108), with the exclusion of BNP(1-76) and of BNP(77-108).

The antibody according to the invention derived from the hybridoma 3D4 is therefore clearly an antibody that specifically recognizes proBNP(1-108), with the substantial exclusion of BNP(1-76) and of BNP(77-108).

Example 13

Validation by Western Blotting of the Specificity of the Antibody Produced by the Hybridoma 3D4

Materials:
1) Conventional SDS-PAGE electrophoresis apparatus
2) Stacking gel: 5% acrylamide.
3) Resolving gel: 16% acrylamide.
4) Anode buffer: 0.2M Tris, pH 8.9.
5) Cathode buffer: 0.1M Tris-tricine; 0.1% SDS.
6) Sample buffer: 0.5M Tris, pH 6.8; 25% glycerol; 2% SDS; 14.4 mM beta-mercaptoethanol; 0.1% bromophenol blue.
7) Electrophoretic transfer apparatus.
8) Transfer buffer: 25 mM Tris base; 190 mM glycine; 20% methanol; 0.05% SDS.
9) The BNP(77-108) comes from Sigma (#B-5900), while the proBNP(1-108)-GST, the BNP(1-76)-GST and the GST (used as negative control) were produced in the form of recombined proteins. The concentration of these protein solutions was determined by the Bradford method for colorimetric assay of proteins (M. Bradford, Anal. Biochem. 1976; 72: 248-54).
10) The conjugate used is a peroxidase-coupled donkey anti-mouse IgG polyclonal antibody (Jackson Immunoresearch #715-035-150).
11) ECL kit for detection by Western blotting (Amersham Biosciences #RPN2106).

Protocol:

The implementation of this assay comprises three main steps: electrophoretic migration of the various proteins in a 16% acrylamide gel, then transfer of these proteins onto a nitrocellulose membrane and, finally, Western blotting.

Various solutions are prepared in sample buffer in a final volume of 35 µl: a first comprising 1 µg of proBNP(1-108)-GST, a second comprising 1 µg of GST, a third comprising 1 µg of BNP(1-76)-GST, and a fourth comprising 1 µg of BNP(77-108).

Each solution is incubated in a waterbath for 5 minutes at 100° C., and then loaded into a well of the gel. The migration through the acrylamide gel is effected under constant voltage at 120V for 1 hour 30 min. FIG. 9 corresponds to a photograph of the acrylamide gel obtained. The proteins loaded are stained with coomassie blue.

After migration, the proteins in the gel are transferred onto a nitrocellulose membrane for 1 hour under 120 mA.

The nitrocellulose membrane is then washed with PBS buffer+0.1% Tween, and saturated for 30 minutes at ambient temperature in PBS buffer+0.1% Tween+2% skimmed milk.

After 3 washes with PBS buffer+0.1% Tween, the membrane is incubated for 1 hour at +37° C., with agitation, with 5 ml of hybridoma 3D4 supernatant.

After 3 washes with the PBS buffer+0.1% Tween, the membrane is incubated for 1 hour at ambient temperature, with agitation, with 10 ml of peroxidase-coupled anti-mouse IgG conjugate diluted to 1/2000 in PBS buffer+0.1% Tween+2% skimmed milk.

After 3 washes with the PBS buffer+0.1% Tween, the membrane is soaked in the ECL visualizing reagent, before being exposed to a photographic film for 4 minutes.

As shown in FIG. 10, which corresponds to the scanned image of the photograph obtained, the antibody produced in the hybridoma 3D4 supernatant is capable of detecting only the band corresponding to proBNP(1-108). BNP(1-76), BNP (77-108) and also GST are not detected by the antibody of the hybridoma 3D4. These results also validate the specificity of the antibody produced by the hybridoma 3D4 for proBNP(1-108).

The antibody according to the invention derived from the hybridoma 3D4 is therefore clearly an antibody that specifically recognizes proBNP(1-108), with the substantial exclusion of BNP(1-76) and of BNP(77-108).

Example 14

Identification of the Epitope Recognized by the Antibody Produced by the Hybridoma 3D4, by the Spot Method The hybridoma 3D4 supernatant was tested by the spot method (described in example 6) in order to identify the epitope recognized by the hybridoma 3D4 antibody. The results obtained indicate that the 3D4 antibody effectively recognizes peptide sequences comprising the $RAPR_{76}S_{77}P$ unit.

These results are in agreement with those obtained by ELISA (example 12) and Western blotting (example 13), validating the specificity of the 3D4 antibody for proBNP(1-108).

Example 15

Immunoradiometric Assay for proBNP(1-108)

Materials:
1) Solid phase: flat-bottomed cleavable-well Maxisorp microplate, Nunc (Denmark).
2) The capture antibody used is the polyclonal antibody obtained from the serum from rabbit #046 805, not depleted.
3) The conjugate used is an anti-BNP(77-108) antibody labeled with $I^{125}$ (anti-BN:-$I^{125}$). It is the tracer antibody of the Shionoria BNP kit sold by the company Shionogi.
4) Saturation buffer: Dulbecco PBS buffer, at pH 7.4, containing 1% of bovine serum albumin (BSA, Sigma #A-7888).
5) Dilution buffer: Dulbecco PBS buffer, at pH 7.4, containing 0.1% of BSA and 0.1% of Tween 20 (Sigma #P-1379).
6) Washing buffer: Dulbecco PBS buffer, at pH 7.4, containing 0.1% of Tween 20.
7) proBNP(1-108) standard: product in the form of a recombined protein.

Protocol:
The principle of the assay used is based on the sandwich radioimmunoassay method, carried out in a flat-bottomed cleavable-well microplate. It is a one-step assay in which sample (or standard solution of proBNP(1-108)) and tracer are added one after the other without intermediate washing.

A coating solution is first of all prepared with the polyclonal antibody from rabbit #046 805, diluted in Dulbecco PBS buffer, at pH 7.4, to 40 µg/ml. 300 µl of this solution are deposited into each of the wells of the microplate.

The microplate is incubated overnight at 4° C.

After removal of the coating solution, the microplate is washed with 300 µl of a Dulbecco PBS buffer, at pH 7.4, containing 0.1% of Tween 20, and then saturated by addition of 300 µl of Dulbecco PBS buffer, at pH 7.4, containing 1% of BSA.

The microplate is then incubated for 1 hour at 37° C.

The microplate is then washed (3 times) with 300 µl of the washing solution (Dulbecco PBS buffer, at pH 7.4, to which has been added 0.1% Tween 20).

100 µl of standard proBNP(1-108) solution, of serum or of plasma are deposited in each cupule. The proBNP(1-108), if it is present, binds to the capture antibody retained on the solid phase.

200 µl of the ready-to-use anti-BNP-$I^{125}$ tracer solution (taken from the Shionogi Shionoria BNP kit) are added to each of the wells.

The reaction medium is incubated overnight (18-22 h) at 4° C.

The following day, the microplate is washed (3 times) with 300 µl of the washing solution. At the final wash, and after the washing solution has been suctioned out, each cupule is transferred into a pre-identified tube.

The radioactivity present in each cupule, and proportional to the amount of tracer bound, and therefore to the amount of proBNP(1-108) present in the sample, is measured using a gamma counter.

FIG. 11 gives the results obtained using a standard range of proBNP(1-108).

Example 16

Results of the Assaying of Human Samples 14 samples from normal individuals and 15 samples from patients suffering from heart failure were tested by means of the proBNP(1-108) IRMA assay according to the invention described in example 15 and of the BNP(1-76) assay sold by the company Roche and carried out on the Elecsys® automated device. The blood samples were all taken on a tube containing EDTA. FIG. 12 gives the results in cpm (counts per minute) of the tests carried out on these samples with the proBNP(1-108) IRMA assay according to the invention. The results obtained on the samples from patients suffering from heart failure are significantly higher than those obtained on the samples from normal individuals. These results demonstrate the presence of circulating proBNP(1-108) in the samples from patients suffering from heart failure, and constitute the first demonstration that serum proBNP(1-108) is a marker for predicting heart failure. FIG. 13 shows the correlation between the concentrations of proBNP(1-108) (in pg/ml) determined by means of the proBNP IRMA assay according to the invention and the concentrations of BNP(1-

76) (pg/ml) determined by means of the Roche assay on the Elecsys® automated device, of the samples from 14 patients suffering from heart failure. The correlation observed is significant with a coefficient $R^2=0.85$.

Example 17

Coupling of the Polyclonal Antibody from Rabbit #046 805 to Biotin

The coupling method uses an N-hydroxysuccinimide (NHS) derivative of biotin, which reacts with the primary amines of IgGs so as to form an amide bond.

A 100 mM solution of (+)-biotin N-succinimidyl ester (Fluka #14405) is prepared by dissolving biotin in dimethylformamide. The biotinylation is carried out in a glass flask. 500 µg of the polyclonal antibody from rabbit #046 805, purified beforehand but not depleted, are placed in the flask with 17 µl of the 100 mM biotin solution (the biotin/antibody molar ratio is 500). The reaction is carried out in Dulbecco PBS buffer at pH 7.4. The reaction mixture is incubated for 1 hour 30 min at ambient temperature with slow stirring. After coupling, the biotin is inactivated by adding a volume of 2M glycine buffer. The mixture is incubated for 10 minutes at ambient temperature with slow stirring. Finally, the mixture is dialyzed overnight at 4° C. against Dulbecco PBS buffer at pH 7.4. The following day, a solution of sodium azide is added at a final concentration of 0.02%. The conjugate is stored at 4° C.

Example 18

Immunoenzymometric Assay for proBNP(1-108)

An immunoenzymometric assay according to the invention was also set up.

Materials:
1) Solid phase: flat-bottomed Maxisorp microplate, Nunc (Denmark).
2) The capture antibody used is a polyclonal anti-BNP(77-108) antibody sold by the company Strategic Biosolution (#B9105RA00-A0).
3) The conjugate used is the polyclonal antibody from rabbit #046 805, not depleted, coupled to biotin according to the method described in example 17.
4) Streptavidin-peroxidase conjugate (Amersham Pharmacia Biotech #RPN1231V).
5) Saturation buffer: Dulbecco PBS buffer, at pH 7.4, containing 1% of bovine serum albumin (BSA, Sigma #A-7888).
6) Dilution buffer: Dulbecco PBS buffer, at pH 7.4, containing 0.1% of BSA and 0.1% of Tween 20.
7) Washing solution: Dulbecco PBS buffer, at pH 7.4, containing 0.1% of Tween 20.
8) proBNP(1-108) standard: recombined protein.
9) Visualizing solution: the visualizing solution is composed:
9a) of a substrate buffer: solution of 0.01M citric acid and of 0.04M trisodium citrate containing 0.33% $H_2O_2$, final pH 5.6, and
9b) of a chromogen: OPD (ortho-phenylenediamine) tablets. 1 OPD tablet to be dissolved in 10 ml of substrate buffer.
10) Stop solution: 4N $H_2SO_4$.

Protocol:
The principle of the assay is based on the sandwich-type immunoenzyme assay method carried out in a flat-bottomed plate. It is a two-step assay in which the sample (or the standard solution) is first of all incubated with the capture antibody and then, after incubation and washes, the detection antibody is added.

A coating solution is first of all prepared with the anti-BNP (77-108) polyclonal antibody diluted in Dulbecco PBS buffer, at pH 7.4, to 10 µg/ml. 100 µl of this solution are deposited into each of the wells of the microplate.

The microplate is incubated overnight at 4° C.

After removal of the coating solution, the microplate is washed with 300 µl of a Dulbecco PBS buffer, at pH 7.4, containing 0.1% of Tween 20, and then saturated by addition of 250 µl of Dulbecco PBS buffer, at pH 7.4, containing 1% of BSA.

The microplate is then incubated for 1 hour at 37° C.

The microplate is then washed (3 times) with the washing solution.

100 µl of standard proBNP(1-108) solution, of serum or of plasma are deposited into each cupule. The proBNP(1-108), if it is present, binds to the capture antibody retained on the solid phase.

The reaction medium is incubated for 2 hours at ambient temperature.

The microplate is then washed (5 washes) with 300 µl of the washing solution.

100 µl of biotinylated polyclonal antibody from rabbit #046 805 (concentrated to 6 µg/ml) are added to each well of the microplate.

The reaction medium is incubated for 2 hours at ambient temperature.

The microplate is then washed (5 washes) with 300 µl of the washing solution.

Finally, 100 µl of streptavidin-POD conjugate diluted to 1/1000 are added to each of the wells of the microplate.

The reaction medium is incubated for 1 hour 30 min at ambient temperature.

The plates are then washed (5 washes) with 300 µl of the washing solution. 100 µl of the visualizing solution are distributed into each cupule. The reaction is left to develop in the dark for 20 minutes at ambient temperature (18-24° C.).

50 µl of the stop solution are then distributed into each cupule.

After the reaction has been stopped, the optical density is read on a spectrophotometer at 490/620 nm.

FIG. 14 gives the results obtained using a standard proBNP (1-108) range.

Example 19

Evaluation of the Cross Reaction, with Respect to BNP(1-76) and to BNP(77-108), of the Non-depleted, Biotin-coupled Polyclonal Antibody from #046 805, Used in a Sandwich in the proBNP(1-108) ELISA Assay, Together with the Anti-BNP(77-108) Polyclonal Antibody The cross reaction of the non-depleted, biotinylated anti-proBNP(1-108) antibody according to the invention (rabbit #046 805) with respect to BNP(1-76) and to BNP(77-108), was evaluated by means of the proBNP(1-108) ELISA assay described in example 18. Concentration ranges of 5 ng/ml to 100 ng/ml were prepared with proBNP(1-108), BNP(1-76) and BNP(77-108), and were assayed by means of the proBNP (1-108) ELISA assay described in example 18. The results of the variation in optical density at 490 nm as a function of the concentration are given in FIG. 15 for each of the proteins. No cross reaction is observed with respect to BNP(1-76) or to BNP(77-108): the signal obtained is equivalent to the background noise, whatever the concentration assayed. At the BNP(1-76) and BNP(77-108) concentrations usually found in patients (of the order of 1 ng/ml for the highest concentrations), the polyclonal antibody from rabbit #046 805 can be used in its non-depleted version without resulting in the appearance of cross reaction.

Example 20

Evaluation of the Cross Reaction, with Respect to BNP(1-76) and to BNP(77-108), of the Non-depleted, Biotin-coupled Polyclonal Antibody from Rabbit #046 805, Used in a Sandwich in the proBNP (1-108) ELISA Assay, Together with the Anti-NT-proBNP(1-29) Polyclonal Antibody The cross reaction of the non-depleted, biotinylated polyclonal antibody from rabbit #046 805, with respect to BNP (1-76) and to BNP(77-108), was evaluated by means of a proBNP(1-108) ELISA assay using the protocol and the reagents described in example 18, except for the fact that the antiBNP(77-108) polyclonal antibody is, in this instance, replaced with an anti-NT-proBNP(1-29) polyclonal antibody.

The anti-NT-proBNP(1-29) polyclonal antibody was produced according to the protocol described in example 3, apart from the fact that the peptide used as immunogen was the peptide NT-proBNP(1-29) coupled to KLH. Concentration ranges of 5 ng/ml to 100 ng/ml were prepared with proBNP (1-108), BNP(1-76) and BNP(77-108), and were assayed by means of the proBNP(1-108) ELISA assay. The results of the variation in optical density at 490 nm as a function of the concentration are given in FIG. 16 for each of the proteins. No cross reaction of the polyclonal antibody from rabbit #046 805 according to the invention is observed with respect to BNP(1-76) or to BNP(77-108); the signal obtained is equivalent to the background noise, whatever the concentration assayed. At the BNP(1-76) and BNP(77-108) concentrations usually found in patients (of the order of 1 ng/ml), the polyclonal antibody from rabbit #046 805 can be used in its non-depleted version without resulting in the appearance of a cross reaction.

In summary, it clearly emerges from the entire disclosure above that the present invention has made it possible to discover a novel epitope, $RAPR_{76}S_{77}P$, located on the hinge region of human proBNP(108), to derive therefrom immunogenic peptides containing it, and to obtain antibodies specific for proBNP(108) which do not substantially recognize BNP (1-76) or BNP(77-108), and some of which have the ability of specifically recognizing circulating proBNP(1-108) in human serum or plasma samples.

It also clearly appears that the present invention has made it possible to develop an assay for circulating proBNP(1-108) that thus makes it possible to diagnose heart failure simply, routinely and reliably.

---

The invention claimed is:

1. An isolated anti-proBNP(1-108) antibody, characterized in that, firstly, it specifically recognizes the sequence RAPR$_{76}$S$_{77}$P (SEQ ID NO: 5) of proBNP(1-108) and does not substantially recognize the peptides BNP(1-76) or BNP (77-108) and, secondly, it has the ability to specifically recognize circulating proBNP(1-108) in human serum or plasma samples.

2. The anti-proBNP(1-108) antibody as claimed in claim 1, which specifically recognizes the sequence Y$_{70}$TLRAPR$_{76}$S$_{77}$PKMVQGSG$_{85}$ (SEQ ID NO: 4) of proBNP(1-108).

3. The anti-proBNP(1-108) antibody as claimed in claim 1, which specifically recognizes the sequence Y$_{70}$TLRAPR$_{76}$S$_{77}$PKMVQGS$_{84}$ (SEQ ID NO: 108) of proBNP(1-108).

4. A method for obtaining an anti-proBNP(1-108) antibody as defined in claim 1, in which an animal is immunized with the whole proBNP(1-108) molecule, and then the antiserum obtained is depleted using the BNP(77-108) peptide and/or the BNP(1-76) peptide.

5. A method for obtaining an anti-proBNP(1-108) antibody as defined in claim 1, in which an animal is immunized with a peptide chosen from a peptide of formula $$a_1\text{-}X_1\text{-RAPRSP-}X_2\text{-}a_2 \text{ (SEQ ID NO: 5)} \quad (I)$$

where a1 may be H or may represent a function or a chemical group chosen from a thiol, alcohol, aminoxy, primary amine or secondary amine function, an aminocarboxyl group, a biotinyl group and an acetyl group, X$_1$ represents a peptide sequence of 0 to 3 amino acids, which may or may not be derived from the natural sequence of proBNP(1-108), X$_2$ represents a peptide sequence of 0 to 7 amino acids, which may or may not be derived from the natural sequence of proBNP(1-108), a2 may represent an OH function, an NH2 function or an alkoxyl group;

a peptide of formula $$X\text{-}Y_{70}\text{TLRAPR}_{76}S_{77}\text{PKMVQGSG}_{85}\text{-}Z \text{ (SEQ ID NO: 4)} \quad (II)$$

where X may be H or may represent either an acetyl group, or 1 to 3 amino acids not belonging to the sequence of proBNP(1-108), and where Z may represent an OH function, or 1 to 3 amino acids not belonging to the sequence of proBNP(1-108);

a peptide of formula $$X\text{-}Y_{70}\text{TLRAPR}_{76}S_{77}\text{PKMVQGS}_{84}\text{-}Z \text{ (SEQ ID NO: 108)} \quad (III)$$

where X may be H or may represent either an acetyl group, or 1 to 3 amino acids not belonging to the sequence of proBNP(1-108), and where Z may represent an OH function, or 1 to 3 amino acids not belonging to the sequence of proBNP(1-108);

a peptide comprising a sequence derived from the sequence

X-Y$_{70}$TLRAPR$_{76}$S$_{77}$PKMVQGSG$_{85}$-Z (II) or from the sequence

X-Y$_{70}$TLRAPR$_{76}$S$_{77}$PKMVQGS$_{84}$-Z (III) by substitution of one or more among the amino acids Y$_{70}$, T$_{71}$, L$_{72}$, K$_{79}$, M$_{80}$, V$_{81}$, Q$_{82}$, G$_{83}$, S$_{84}$ and G$_{85}$, with it being possible for X to be H or to represent either an acetyl group, or 1 to 3 amino acids not belonging to the sequence of proBNP(1-108), and where Z may be an OH function, or 1 to 3 amino acids not belonging to the sequence of proBNP(1-108);

the peptide having the sequence C-Y-T-L-R-A-P-R-S-P-K-M-V-Q-G-S-G (C13P30: SEQ ID NO: 16);

the peptide having the sequence C-Y-T-L-R-A-P-R-S-P-K-M-V-Q-G-S (CN32: SEQ ID No. 109);

and, optionally, the antiserum obtained is depleted using the BNP(77-108) peptide and/or the BNP(1-76) peptide.

6. A method for obtaining a hybridoma that secretes an anti-proBNP(1-108) antibody as defined in claim 1, in which an animal is immunized with a peptide chosen from a peptide of formula $$a_1\text{-}X_1\text{-RAPRSP-}X_2\text{-}a_2 \text{ (SEQ ID NO: 5)} \quad (I)$$

where
- $a_1$ may be H or may represent a function or a chemical group chosen from a thiol, alcohol, aminoxy, primary amine or secondary amine function, an aminocarboxyl group, a biotinyl group and an acetyl group,
- $X_1$ represents a peptide sequence of 0 to 3 amino acids, which may or may not be derived from the natural sequence of proBNP(1-108),
- $X_2$ represents a peptide sequence of 0 to 7 amino acids, which may or may not be derived from the natural sequence of proBNP(1-108),
- $a_2$ may represent an OH function, an $NH_2$ function or an alkoxyl group;

a peptide of formula $$X\text{-}Y_{70}\text{TLRAPR}_{76}S_{77}\text{PKMVQGSG}_{85}\text{-Z (SEQ ID NO: 4)} \quad (II)$$

where X may be H or may represent either an acetyl group, or 1 to 3 amino acids not belonging to the sequence of proBNP(1-108), and where Z may represent an OH function, or 1 to 3 amino acids not belonging to the sequence of proBNP(1-108);

a peptide of formula $$X\text{-}Y_{70}\text{TLRAPR}_{76}S_{77}\text{PKMVQGS}_{84}\text{-Z (SEQ ID NO: 108)} \quad (III)$$

where X may be H or may represent either an acetyl group, or 1 to 3 amino acids not belonging to the sequence of proBNP(1-108), and where Z may represent an OH function, or 1 to 3 amino acids not belonging to the sequence of proBNP(1-108);

a peptide comprising a sequence derived from the sequence $X_{70}\text{TLRAPR}_{76}S_{77}\text{PKMVQGSG}_{85}\text{-Z}$ (II) or from the sequence $X\text{-}Y_{70}\text{TLRAPR}_{76}S_{77}\text{PKMVQGS}_{84}\text{-Z}$ (III) by substitution of one or more among the amino acids $Y_{70}, T_{71}, L_{72}, K_{79}, M_{80}, V_{81}, Q_{82}, G_{83}, S_{84}$ and $G_{85}$, with it being possible for X to be H or to represent either an acetyl group, or 1 to 3 amino acids not belonging to the sequence of proBNP(1-108), and where Z may be an OH function, or 1 to 3 amino acids not belonging to the sequence of proBNP(1-108);

the peptide having the sequence C-Y-T-L-R-A-P-R-S-P-K-M-V-Q-G-S-G (C13P30: SEQ ID NO: 16);

the peptide having the sequence C-Y-T-L-R-A-P-R-S-P-K-M-V-Q-G-S (CN32: SEQ ID NO: 109);

immunoglobulin-secreting lymphocytes are taken from this animal, and the lymphocytes are fused with myeloma cells so as to obtain at least one immunoglobulin-secreting hybridoma.

7. The method as claimed in claim 5, in which the peptide of formula (II) has the sequence $Y_{70}\text{TLRAPR}_{76}S_{77}\text{PKMVQGSG}_{85}$ (SEQ ID NO: 4).

8. The method as claimed in claim 5, in which the peptide of formula (III) has the sequence $Y_{70}\text{TLRAPR}_{76}S_{77}\text{PKMVQGS}_{84}$ (SEQ ID NO: 108).

9. A hybridoma which can be produced by the method as claimed in claim 6, wherein the antibody secreted by the hybridoma specifically recognizes the sequence $\text{RAPR}_{76}S_{77}P$ (SEQ ID NO: 5) of proBNP(1-108) and does not substantially recognize the peptides BNP(1-76) or BNP(77-108).

10. An anti-proBNP(1-108) monoclonal antibody secreted by a hybridoma as claimed in claim 9.

11. A method of in vitro diagnosis of heart failure in a human subject, comprising bringing a biological sample of the human subject into contact with an anti-proBNP(1-108) antibody as defined in claim 1 and detecting the proBNP(1-108) in the sample, whereby, if the proBNP(1-108) concentration in the biological sample is higher than that of normal individuals, then the human subject is diagnosed as having heart failure.

12. A method of in vitro diagnosis of heart failure in a human subject, comprising:
a) bringing a biological sample of the human subject into contact with an anti-proBNP(1-108) antibody as defined in claim 1,
b) incubating the mixture under conditions that allow the formation of antigen-antibody complexes, and
c) revealing the antigen-antibody complexes formed, optionally using a labeled detection antibody capable of binding specifically to the proBNP(1-108) present in the primary complex, or using a labeled detection antigen capable of binding to the antibody directed against said proBNP(1-108) present in the primary complex, and
d) correlating the amount of antigen-antibody complexes revealed with the clinical condition of the human subject, wherein, if the amount of antigen-antibody complexes is higher than that of normal individuals, then the human subject is diagnosed as having heart failure.

13. A kit for detecting proBNP(1-108) in a biological sample, containing at least one antibody as defined in claim 1.

14. The kit for detecting proBNP(1-108) in a biological sample, as claimed in claim 13, containing:
(i) in a container, the at least one antibody;
(ii) in another container, at least one peptide chosen from
a peptide of formula $$a_1\text{-}X_1\text{-RAPRSP-}X_2\text{-}a_2 \text{ (SEQ ID NO: 5)} \quad (I)$$

where
- $a_1$ may be H or may represent a function or a chemical group chosen from a thiol, alcohol, aminoxy, primary amine or secondary amine function, an aminocarboxyl group, a biotinyl group and an acetyl group,
- $X_1$ represents a peptide sequence of 0 to 3 amino acids, which may or may not be derived from the natural sequence of proBNP(1-108),
- $X_2$ represents a peptide sequence of 0 to 7 amino acids, which may or may not be derived from the natural sequence of proBNP(1-108),
- $a_2$ may represent an OH function, an $NH_2$ function or an alkoxyl group;

a peptide of formula $$X\text{-}Y_{70}\text{TLRAPR}_{76}S_{77}\text{PKMVQGSG}_{85}\text{-Z (SEQ ID NO: 4)} \quad (II)$$

where X may be H or may represent either an acetyl group, or 1 to 3 amino acids not belonging to the sequence of proBNP(1-108), and where Z may represent an OH function, or 1 to 3 amino acids not belonging to the sequence of proBNP(1-108);

a peptide of formula $$X\text{-}Y_{70}\text{TLRAPR}_{76}S_{77}\text{PKMVQGS}_{84}\text{-Z (SEQ ID NO: 108)} \quad (III)$$

where X may be H or may represent either an acetyl group, or 1 to 3 amino acids not belonging to the sequence of proBNP(1-108), and where Z may represent an OH function, or 1 to 3 amino acids not belonging to the sequence of proBNP(1-108);

a peptide comprising a sequence derived from the sequence X-Y$_{70}$TLRAPR$_{76}$S$_{77}$PKMVQGSG$_{85}$-Z (SEQ ID NO: 4) (II) or from the sequence X-Y$_{70}$TLRAPR$_{76}$S$_{77}$PKMVQGS$_{84}$-Z (SEQ ID NO: 108) (III) by substitution of one or more among the amino acids Y$_{70}$, T$_{71}$, L$_{72}$, K$_{79}$, M$_{80}$, V$_{81}$, Q$_{82}$, G$_{83}$, S$_{84}$ and G$_{85}$, with it being possible for X to be H or to represent either an acetyl group, or 1 to 3 amino acids not belonging to the sequence of proBNP(1-108), and where Z may be an OH function, or 1 to 3 amino acids not belonging to the sequence of proBNP(1-108);

the peptide having the sequence Y$_{70}$TLRAPR$_{76}$S$_{77}$PKMVQGSG$_{85}$ (SEQ ID NO: 4);

the peptide having the sequence Y$_{70}$TLRAPR$_{76}$S$_{77}$PKMVQGS$_{84}$ (SEQ ID NO: 108);

the peptide having the sequence C-Y-T-L-R-A-P-R-S-P-K-M-V-Q-G-S-G (C13P30: SEQ ID NO: 16);

the peptide having the sequence C-Y-T-L-R-A-P-R-S-P-K-M-V-Q-G-S (CN32: SEQ ID NO: 109).

15. A peptide of formula:

a$_1$-X$_1$-RAPRSP-X$_2$-a$_2$ (SEQ ID NO: 5)  (I)

where a$_1$ may be H or may represent a function or a chemical group chosen from a thiol, alcohol, aminoxy, primary amine or secondary amine function, an aminocarboxyl group, a biotinyl group or an acetyl group, X$_1$ represents a peptide sequence of 0 to 3 amino acids, which may or may not be derived from the natural sequence of proBNP(1-108), X$_2$ represents a peptide sequence of 0 to 7 amino acids, which may or may not be derived from the natural sequence of proBNP(1-108), a$_2$ may represent an OH function, an NH$_2$ function, or an alkoxyl group.

16. A peptide of formula

X-Y$_{70}$TLRAPR$_{76}$S$_{77}$PKMVQGSG$_{85}$-Z (SEQ ID NO: 4)  (II)

where X may be H or may represent either an acetyl group, or 1 to 3 amino acids not belonging to the sequence of proBNP (1-108), and where Z may represent an OH function, or 1 to 3 amino acids not belonging to the sequence of proBNP(1-108).

17. The peptide as claimed in claim 16, having the sequence Y$_{70}$TLRAPR$_{76}$S$_{77}$PKMVQGSG$_{85}$ (SEQ ID NO: 4).

18. A peptide of formula:

X-Y$_{70}$TLRAPR$_{76}$S$_{77}$PKMVQGS$_{84}$-Z (SEQ ID NO: 108)  (III)

where X may be H or may represent either an acetyl group, or 1 to 3 amino acids not belonging to the sequence of proBNP (1-108), and where Z may represent an OH function, or 1 to 3 amino acids not belonging to the sequence of proBNP(1-108).

19. The peptide as claimed in claim 18, having the sequence Y$_{70}$TLRAPR$_{76}$S$_{77}$PKMVQGS$_{84}$ (SEQ ID NO: 108).

20. A peptide comprising a sequence derived from the sequence X-Y$_{70}$TLRAPR$_{76}$S$_{77}$PKMVQGSG$_{85}$-Z (SEQ ID NO: 4) (II) or from the sequence X-Y$_{70}$TLRAPR$_{76}$S$_{77}$PKMVQGS$_{84}$-Z (SEQ ID No. 108) (III) by substitution of one or more among the amino acids Y$_{70}$, T$_{71}$, L$_{72}$, K$_{79}$, M$_{80}$, V$_{81}$, Q$_{82}$, G$_{83}$, S$_{84}$ and G$_{85}$, with it being possible for X to be H or to represent either an acetyl group, or 1 to 3 amino acids not belonging to the sequence of proBNP(1-108), and where Z may be an OH function, or 1 to 3 amino acids not belonging to the sequence of proBNP(1-108).

21. The peptide as claimed in claim 15, having a sequence chosen from the group consisting of the following sequences

| | |
|---|---|
| SEQ ID NO: 16: | C-Y-T-L-R-A-P-R-S-P-K-M-V-Q-G-S-G (peptide C13P30) |
| SEQ ID NO: 109: | C-Y-T-L-R-A-P-R-S-P-K-M-V-Q-G-S (peptide CN32) |
| SEQ ID NO: 6: | C-G-R-A-P-R-S-P |
| SEQ ID NO: 7: | Acetyl-C-G-R-A-P-R-S-P |
| SEQ ID NO: 8: | C-G-R-A-P-R-S-P-K |
| SEQ ID NO: 9: | Acetyl-C-G-R-A-P-R-S-P-K |
| SEQ ID NO: 10: | C-G-R-A-P-R-S-P-K-M-V |
| SEQ ID NO: 11: | C-G-R-A-P-R-S-P-K-M-V-Q-G-S-G |
| SEQ ID NO: 12: | R-A-P-R-S-P-G-C |
| SEQ ID NO: 13: | Acetyl-R-A-P-R-S-P-G-C |
| SEQ ID NO: 110: | C-Y-T-L-R-A-P-R-S-P-K |
| SEQ ID NO: 111: | C-Y-T-L-R-A-P-R-S-P-K-M-V |
| SEQ ID NO: 112: | C-Y-T-L-R-A-P-R-S-P-K-M-V-Q |
| SEQ ID NO: 113: | C-Y-T-L-R-A-P-R-S-P-K-M-V-Q-G |
| SEQ ID NO: 19: | C-Y-T-L-R-A-P-R-S-P-K-M-V-Q-G-S-bA |
| SEQ ID NO: 20: | C-Y-T-L-R-A-P-R-S-P-K-M-V-Q-A-T-bA |
| SEQ ID NO: 114: | Acetyl-C-T-L-R-A-P-R-S-P-K-M-V-Q |
| SEQ ID NO: 115: | C-T-L-R-A-P-R-S-P-K-M-V-Q-G |
| SEQ ID NO: 116: | C-T-L-R-A-P-R-S-P-K-M-V-Q-G-S |
| SEQ ID NO: 117: | C-T-L-R-A-P-R-S-P-K-M-V-Q-G-S-G |
| SEQ ID NO: 118: | C-L-R-A-P-R-S-P-K-M-V |
| SEQ ID NO: 119: | C-L-R-A-P-R-S-P-K-M-V-Q |
| SEQ ID NO: 120: | L-R-A-P-R-S-P-K-M-V-Q-C |
| SEQ ID NO: 121: | C-L-R-A-P-R-S-P-K-M-V-Q-G-S |
| SEQ ID NO: 122: | C-L-R-A-P-R-S-P-K-M-V-Q-G-S-G. |

22. A method for obtaining anti-proBNP(1-108) antibodies that specifically recognize the sequence Y$_{70}$TLRAPR$_{76}$S$_{77}$PKMVQGSG$_{85}$, (SEQ ID NO: 4) the sequence Y$_{70}$TLRAPR$_{76}$S$_{77}$PKMVQGS$_{84}$ (SEQ ID NO: 108) and/or the sequence RAPR$_{76}$S$_{77}$P (SEQ ID NO: 5) of proBNP(1-108) with the substantial exclusion of the BNP(1-76) and BNP(77-108) peptides, and that have the ability to specifically recognize circulating proBNP(1-108) in human serum or plasma samples, in which method an animal is immunized with a peptide as defined in claim 15, and, optionally, the antiserum obtained is depleted using the BNP(77-108) peptide and/or the BNP(1-76) peptide.

23. A method for obtaining a hybridoma that secretes an anti-proBNP(1-108) antibody that specifically recognizes the sequence Y$_{70}$TLRAPR$_{76}$S$_{77}$PKMVQGSG85 (SEQ ID NO: 4), the sequence Y$_{70}$TLRAPR$_{76\ S77}$PKMVQGS84 (SEQ ID NO: 108) and/or the sequence RAPR$_{76}$S$_{77}$P (SEQ ID NO: 5) of proBNP(1-108) with the substantial exclusion of the BNP (1-76) and BNP(77-108) peptides, and that has the ability to specifically recognize circulating proBNP(1-108) in human serum or plasma samples, in which method an animal is immunized with a peptide as defined in claim 15, followed by removal of immunoglobulin-secreting lymphocytes from this animal, and said lymphocytes are fused with myeloma cells so as to obtain at least one immunoglobulin-secreting hybridoma.

24. An anti-proBNP(1-108) antibody, characterized in that it is obtained by a method as claimed in claim 22.

25. The anti-proBNP(1-108) antibody as claimed in claim 24, which specifically recognizes the sequence $Y_{70}TLRAPR_{76}S_{77}PKMVQGSG_{85}$ (SEQ ID NO: 4) or the sequence $Y_{70}TLRAPR_{76}S_{77}PKMVQGS_{84}$ (SEQ ID NO: 108) of proBNP(1-108).

26. A hybridoma which can be produced by the method as claimed in claim 23, wherein the antibody secreted by the hybridoma specifically recognizes the sequence $Y_{70}TLRAPR_{76}S_{77}PKMVQGSG85$ (SEQ ID NO: 4), the sequence $Y_{70}TLRAPR_{76}S_{77}PKMVQGS84$ (SEQ ID NO: 108) and/or the sequence $RAPR_{76}S_{77}P$ (SEQ ID NO. 5) of proBNP(1-108) with the substantial exclusion of the BNP(1-76) and BNP(77-108) peptides.

27. An anti-proBNP(1-108) monoclonal antibody secreted by a hybridoma as claimed in claim 26.

28. The anti-proBNP(1-108) monoclonal antibody as claimed in claim 27, secreted by the hybridoma 3D4 deposited with the CNCM under the No. CNCM I-3073.

29. A method of in vitro diagnosis of heart failure in a human subject, comprising bringing a biological sample of the human subject into contact with an anti-proBNP(1-108) antibody as defined in claim 24 and detecting the proBNP(1-108) in the sample, whereby, if the proBNP(1-108) concentration in the biological sample is higher than that of normal individuals, then the human subject is diagnosed as having heart failure.

30. A method of in vitro diagnosis of heart failure in a human subject, comprising:
 a) bringing a biological sample of the human subject into contact with an anti-proBNP(1-108) antibody as defined in claim 24,
 b) incubating the mixture under conditions that allow the formation of antigen-antibody complexes, and
 c) revealing the antigen-antibody complexes formed, optionally using a labeled detection antibody capable of binding specifically to the proBNP(1-108) present in the primary complex, or using a labeled detection antigen capable of binding to the antibody directed against said proBNP(1-108) present in the primary complex, and
 d) correlating the amount of antigen-antibody complexes revealed with the clinical condition of the human subject, wherein if the amount of antigen-antibody complexes is higher than that of normal individuals then the human subject is diagnosed as having heart failure.

31. A kit for detecting proBNP(1-108) in a biological sample, containing at least one antibody as defined in claim 24.

32. A kit for detecting proBNP(1-108) in a biological sample, containing, as standard and/or control, at least one peptide as defined in claim 15.

33. A kit for detecting proBNP(1-108) in a biological sample, containing:
 in a container, at least one antibody as defined in claim 24;
 in another container, at least one peptide of formula:

$a_1$-$X_1$-RAPRSP-$X_2$-$a_2$ (SEQ ID NO: 5)  (I)

where
 $a_1$ may be H or may represent a function or a chemical group chosen from a thiol, alcohol, aminoxy, primary amine or secondary amine function, an aminocarboxyl group, a biotinyl group or an acetyl group,
 $X_1$ represents a peptide sequence of 0 to 3 amino acids, which may or may not be derived from the natural sequence of proBNP(1-108),
 $X_2$ represents a peptide sequence of 0 to 7 amino acids, which may or may not be derived from the natural sequence of proBNP(1-108),
 $a_2$ may represent an OH function, an $NH_2$ function, or an alkoxyl group.

* * * * *